United States Patent
Lampe et al.

(10) Patent No.: US 8,642,592 B2
(45) Date of Patent: Feb. 4, 2014

(54) OXO-HETEROCYCLICALLY SUBSTITUTED ALKYL CARBOXYLIC ACIDS AND USE THEREOF

(75) Inventors: Thomas Lampe, Düsseldorf (DE); Michael Hahn, Langenfeld (DE); Johannes-Peter Stasch, Solingen (DE); Karl-Heinz Schlemmer, Wuppertal (DE); Frank Wunder, Wuppertal (DE); Stefan Heitmeier, Wülfrath (DE); Nils Griebenow, Dormagen (DE); Sherif El Sheikh, Essen (DE); Volkhart Min-Jian Li, Velbert (DE); Eva-Maria Becker, Wuppertal (DE); Friederike Stoll, Düsseldorf (DE); Andreas Knorr, Erkrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 2 days.

(21) Appl. No.: 13/201,924

(22) PCT Filed: Feb. 24, 2010

(86) PCT No.: PCT/EP2010/001124
§ 371 (c)(1),
(2), (4) Date: Oct. 6, 2011

(87) PCT Pub. No.: WO2010/102717
PCT Pub. Date: Sep. 16, 2010

(65) Prior Publication Data
US 2012/0028971 A1    Feb. 2, 2012

(30) Foreign Application Priority Data

Mar. 9, 2009 (DE) .......................... 10 2009 012 314

(51) Int. Cl.
| | | |
|---|---|---|
| C07D 209/46 | (2006.01) | |
| C07D 237/14 | (2006.01) | |
| C07D 273/04 | (2006.01) | |
| A61K 31/4035 | (2006.01) | |
| A61K 31/50 | (2006.01) | |
| A61K 31/5395 | (2006.01) | |
| A61P 9/00 | (2006.01) | |

(52) U.S. Cl.
USPC ........................................ 514/229.2; 544/68

(58) Field of Classification Search
USPC .......................................... 544/68; 514/229.2
See application file for complete search history.

(56) References Cited

U.S. PATENT DOCUMENTS

| | | | |
|---|---|---|---|
| 5,041,453 A | 8/1991 | Huang et al. | |
| 5,693,650 A | 12/1997 | Müller et al. | |
| 5,811,429 A | 9/1998 | Connell et al. | |
| 5,935,984 A | 8/1999 | Goldmann et al. | |
| 6,667,334 B1 | 12/2003 | Neises et al. | |
| 6,835,752 B2 | 12/2004 | Tani et al. | |
| 6,884,821 B1 | 4/2005 | Shinoda et al. | |
| 7,244,861 B2 | 7/2007 | Matsuura et al. | |
| 7,368,578 B2 | 5/2008 | Momose et al. | |
| 7,371,777 B2 | 5/2008 | Clark et al. | |
| 2011/0034450 A1* | 2/2011 | Hahn et al. | 514/229.2 |
| 2011/0130445 A1* | 6/2011 | Lampe et al. | 514/449 |
| 2012/0172448 A1* | 7/2012 | Lampe et al. | 514/563 |
| 2013/0079412 A1* | 3/2013 | Hahn et al. | 514/563 |

FOREIGN PATENT DOCUMENTS

| | | |
|---|---|---|
| EP | 0608709 A1 | 8/1994 |
| EP | 1229010 A1 | 8/2002 |
| EP | 1285908 A1 | 2/2003 |
| WO | 96/30036 A1 | 10/1996 |
| WO | 00/64888 A1 | 11/2000 |

OTHER PUBLICATIONS

Evgenov, et al.:"NO-Independent Stimulators and Activators of Soluble Guanylate Cyclase: Discovery and Theraputic Potential," Nature Reviews, Sep. 2006, 5(9): 755-768.
Stasch, et al.:"NO-and Haem-independent Activation of Soluble Guanylyl Cyclase: Molecular Basis and Cardiovascular Implications of a New Pharmacological Principle," British Journal of Pharmacology, 2002, 136:773-783.
Stasch, et al.:"Targeting the Heme-Oxidized Nitric Oxide Receptor for Selective Vasodilation of Diseased Blood Vessels," J. Clin. Invest., Sep. 2006, 116(9): 2552-2561.

* cited by examiner

*Primary Examiner* — Bruck Kifle
(74) *Attorney, Agent, or Firm* — Karen B. King

(57) ABSTRACT

The present application relates to novel alkylcarboxylic acids having an oxo-substituted azaheterocyclic partial structure, to processes for their preparation, to their use for the treatment and/or prevention of diseases, and to their use for producing medicaments for the treatment and/or prevention of diseases, especially for the treatment and/or prevention of cardiovascular disorders.

10 Claims, No Drawings

OXO-HETEROCYCLICALLY SUBSTITUTED ALKYL CARBOXYLIC ACIDS AND USE THEREOF

The present application relates to novel alkylcarboxylic acids having an oxo-substituted azaheterocyclic partial structure, to processes for their preparation, to their use for the treatment and/or prevention of diseases, and to their use for producing medicaments for the treatment and/or prevention of diseases, especially for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. Carbon monoxide (CO) is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment [O. V. Evgenov et al., Nature Rev. Drug Disc. 5 (2006), 755]. Substances which directly stimulate soluble guanylate cyclase, i.e. without previous release of NO, have been identified in recent years. The indazole derivative YC-1 was the first NO-independent but heme-dependent sGC stimulator described [Evgenov et al., ibid.]. Based on YC-1, further substances were discovered which are more potent than YC-1 and show no relevant inhibition of phosphodiesterases (PDE). This led to the identification of the pyrazolopyridine derivatives BAY 41-2272, BAY 41-8543 and BAY 63-2521. Together with the recently published structurally different substances CMF-1571 and A-350619, these compounds form the new class of the sGC stimulators [Evgenov et al., ibid.]. A common characteristic of this substance class is an NO—independent and selective activation of the heme-containing sGC. In addition, the sGC stimulators in combination with NO have a synergistic effect on sGC activation based on a stabilization of the nitrosyl-heme complex. The exact binding site of the sGC stimulators at the sGC is still being debated. If the heme group is removed from the soluble guanylate cyclase, the enzyme still has a detectable catalytic basal activity, i.e. cGMP is still being formed. The remaining catalytic basal activity of the heme-free enzyme cannot be stimulated by any of the stimulators mentioned above [Evgenov et al., ibid.].

In addition, NO— and heme-independent sGC activators, with BAY 58-2667 as prototype of this class, have been identified. Common characteristics of these substances are that in combination with NO they only have an additive effect on enzyme activation, and that the activation of the oxidized or heme-free enzyme is markedly higher than that of the heme-containing enzyme [Evgenov et al., ibid.; J. P. Stasch et al., Br. J. Pharmacol. 136 (2002), 773; J. P. Stasch et al., J. Clin. Invest. 116 (2006), 2552]. Spectroscopic studies show that BAY 58-2667 displaces the oxidized heme group which, as a result of the weakening of the iron-histidine bond, is attached only weakly to the sGC. It has also been shown that the characteristic sGC heme binding motif Tyr-x-Ser-x-Arg is absolutely essential both for the interaction of the negatively charged propionic acids of the heme group and for the action of BAY 58-2667. Against this background, it is assumed that the binding site of BAY 58-2667 at the sGC is identical to the binding site of the heme group [J. P. Stasch et al., J. Clin. Invest. 116 (2006), 2552].

The compounds described in the present invention are now likewise capable of activating the heme-free form of soluble guanylate cyclase. This is also confirmed by the fact that these novel activators firstly have no synergistic action with NO at the heme-containing enzyme and that secondly their action cannot be blocked by the heme-dependent inhibitor of soluble guanylate cyclase, 1H-1,2,4-oxadiazolo[4,3-a]quinoxalin-1-one (ODQ), but is even potentiated by this inhibitor [cf. O. V. Evgenov et al., Nature Rev. Drug Disc. 5 (2006), 755; J. P. Stasch et al., J. Clin. Invest. 116 (2006), 2552].

It was thus an object of the present invention to provide novel compounds which act as activators of soluble guanylate cyclase in the manner described above and can be used as such in particular for the treatment and prevention of cardiovascular disorders.

Structurally, the compounds of the present invention are distinguished by a terminal alkyl-carboxylic acid grouping which is attached, in the manner shown below, to an oxo-substituted azaheterocycle as head group.

EP 0 719 763-A1, EP 0 779 279-A1 and EP 0 802 192-A1 described various phenylacetamide derivatives having an azaheterocyclic partial structure as apolipoprotein B inhibitors for the treatment of atherosclerosis and coronary heart disease, and EP 0 608 709-A1 discloses 2-oxochinolinylmethyl-substituted phenylacetamides as angiotensin II antagonists for the treatment of arterial hypertension and atherosclerosis. EP 0 842 943-A2, EP 0 842 944-A2, EP 0 842 945-A2, EP 0 918 059-A1 and WO 99/60015-A1 claim inter alia oxoheterocyclically substituted alkylcarboxylic acids as VLA-4 antagonists and inhibitors of leukocyte adhesion. Furthermore, WO 01/57002-A1 described certain fused azole derivatives as hypoglycemically active agents.

The present invention provides compounds of the general formula (I)

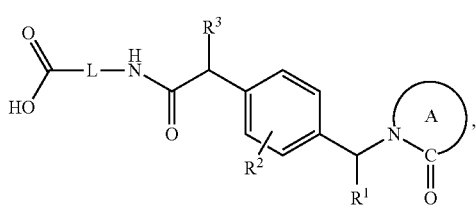

in which ring A represents a 5- to 7-membered saturated or partially unsaturated oxo-substituted azaheterocycle attached via nitrogen,
  which (i) may contain one or two further heteroatoms from the group consisting of N, O and S as ring members,
  which (ii) is substituted by a radical selected from the group consisting of fluorine, chlorine, $(C_1-C_6)$-alkyl, trifluoromethyl, $(C_3-C_7)$-cycloalkyl, 4- to 7-membered heterocyclyl and phenyl or is benzo-fused,
    where the phenyl substituent and the fused phenyl ring for their part may be substituted up to two times by identical or different radicals selected from the group consisting of halogen, cyano, $(C_1-C_4)$-alkyl, $(C_2-C_4)$-alkenyl, trifluoromethyl, $(C_1-C_4)$-alkoxy and trifluoromethoxy,
  and
  which (iii) may additionally be substituted up to two times by identical or different further radicals selected from the group consisting of fluorine, chlorine, $(C_1-C_6)$-alkyl, trifluoromethyl, oxo, $(C_3-C_7)$-cycloalkyl, 4- to 7-membered heterocyclyl and phenyl,
    where phenyl for its part may be substituted up to two times by identical or different radicals selected from the group consisting of halogen, cyano, $(C_1-C_4)$-alkyl, $(C_2-C_4)$-alkenyl, trifluoromethyl, $(C_1-C_4)$-alkoxy and trifluoromethoxy,
$R^1$ represents hydrogen, $(C_1-C_4)$-alkyl or cyclopropyl,
$R^2$ represents hydrogen, halogen, cyano, $(C_1-C_4)$-alkyl or trifluoromethyl,
$R^3$ represents $(C_3-C_6)$-alkyl or $(C_3-C_6)$-alkenyl, each of which may be substituted by cyano, $(C_1-C_4)$-alkoxy or trifluoromethoxy and up to six times by fluorine,
  or
  represents $(C_3-C_7)$-cycloalkyl or $(C_3-C_7)$-cycloalkenyl, each of which may be substituted up to two times by identical or different radicals from the group consisting of $(C_1-C_4)$-alkyl, trifluoromethyl and $(C_1-C_4)$-alkoxy and also up to four times by fluorine,
  or
  represents oxetanyl, tetrahydrofuranyl or tetrahydropyranyl,
and
L represents straight-chain $(C_3-C_7)$-alkanediyl or $(C_3-C_7)$-alkenediyl, each of which may be substituted up to four times by identical or different radicals $R^4$ where
  $R^4$ represents fluorine, trifluoromethyl or $(C_1-C_4)$-alkyl
  or
  two radicals $R^4$ attached to the same carbon atom are linked to each other and together with this carbon atom form a $(C_3-C_6)$-cycloalkane-1,1-diyl ring,
or a salt, solvate or solvate of a salt thereof.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

The compounds according to the invention can exist in stereoisomeric forms (enantiomers, diastereomers), depending on their structure. The invention therefore includes the enantiomers or diastereomers and their particular mixtures. The stereoisomerically uniform constituents can be isolated from such mixtures of enantiomers and/or diastereomers in a known manner.

Where the compounds according to the invention can occur in tautomeric forms, the present invention includes all the tautomeric forms.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid, and benzoic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

The present invention comprises in particular hydrolyzable ester derivatives of the carboxylic acids of the formula (I) according to the invention. These are to be understood as meaning esters which can be hydrolyzed to the free carboxylic acids, as the compounds that are mainly active biologically, in physiological media, under the conditions of the biological tests described later and in particular in vivo by enzymatic or chemical routes. $(C_1-C_4)$-alkyl esters, in which the alkyl group can be straight-chain or branched, are preferred as such esters. Particular preference is given to methyl, ethyl or tert-butyl esters.

In the context of the present invention, the substituents have the following meaning, unless specified otherwise:

$(C_1-C_6)$-Alkyl and $(C_1-C_4)$-alkyl in the context of the invention represent a straight-chain or branched alkyl radical having 1 to 6 or, respectively, 1 to 4 carbon atoms. A straight-chain or branched alkyl radical having 1 to 4 carbon atoms is preferred. The following may be mentioned by way of example and by way of preference: methyl, ethyl, n-propyl, isopropyl, n-butyl, iso-butyl, sec-butyl, tert-butyl, n-pentyl, 2-pentyl, 3-pentyl, n-hexyl, 2-hexyl and 3-hexyl.

$(C_3-C_6)$-Alkyl in the context of the invention represents a straight-chain or branched alkyl radical having 3 to 6 carbon atoms. A straight-chain or branched alkyl radical having 3 to 5 carbon atoms is preferred. There may be mentioned by way of example and preferably: n-propyl, isopropyl, n-butyl, isobutyl, sec-butyl, tert-butyl, n-pentyl, 2-pentyl, 3-pentyl, n-hexyl, 2-hexyl and 3-hexyl.

$(C_3-C_6)$-Alkenyl and $(C_2-C_4)$-alkenyl in the context of the invention represent a straight-chain or branched alkenyl radical having a double bond and 3 to 6 and 2 to 4 carbon atoms, respectively. A straight-chain or branched alkenyl radical having 3 to 5 carbon atoms or a straight-chain alkenyl radical having 2 or 3 carbon atoms is preferred. The following may be mentioned by way of example and by way of preference: vinyl, allyl, isopropenyl, n-but-2-en-1-yl, 2-methylprop-2-en-1-yl and n-but-3-en-1-yl.

$(C_3-C_7)$-Alkanediyl and $(C_3-C_6)$-alkanediyl in the context of the invention represent a straight-chain α,ω-divalent alkyl radical having 3 to 7 and 3 to 6 carbon atoms, respectively. The following may be mentioned by way of example and by way of preference: propane-1,3-diyl (1,3-propylene), butane-1,4-diyl (1,4-butylene), pentane-1,5-diyl (1,5-pentylene), hexane-1,6-diyl (1,6-hexylene) and heptane-1,7-diyl (1,7-heptylene).

$(C_3-C_7)$-Alkenediyl and $(C_3-C_6)$-alkenediyl in the context of the invention represent a straight-chain α,ω-divalent alkyl radical having 3 to 7 and 3 to 6 carbon atoms, respectively, and a double bond.

The following may be mentioned by way of example and by way of preference: propene-1,3-diyl, but-2-ene-1,4-diyl, pent-2-ene-1,5-diyl, hex-2-ene-1,6-diyl, hex-3-ene-1,6-diyl, hept-2-ene-1,7-diyl and hept-3-ene-1,7-diyl.

$(C_1-C_4)$-Alkoxy in the context of the invention represents a straight-chain or branched alkoxy radical having 1 to 4 carbon atoms. The following may be mentioned by way of example and by way of preference: methoxy, ethoxy, n-propoxy, isopropoxy, n-butoxy and tert-butoxy.

$(C_3-C_7)$-Cycloalkyl and $(C_3-C_6)$-cycloalkyl in the context of the invention represent a monocyclic saturated cycloalkyl group having 3 to 7 and 3 to 6 carbon atoms, respectively. A cycloalkyl radical having 3 to 6 carbon atoms is preferred. The following may be mentioned by way of example and by way of preference: cyclopropyl, cyclobutyl, cyclopentyl, cyclohexyl and cycloheptyl.

$(C_3-C_7)$-Cycloalkenyl and $(C_4-C_6)$-cycloalkenyl in the context of the invention represent a mono-cyclic cycloalkyl group having 3 to 7 and 4 to 6 ring carbon atoms, respectively, and a ring double bond. A cycloalkenyl radical having 4 to 6, particularly preferably 5 or 6, carbon atoms is preferred. The following may be mentioned by way of example and by way of preference: cyclopropenyl, cyclobutenyl, cyclopentenyl, cyclohexenyl and cycloheptenyl.

$(C_3-C_6)$-Cycloalkane-1,1-diyl in the context of the invention represents a 1,1-divalent monocyclic saturated cycloalkyl group having 3 to 6 carbon atoms. The following may be mentioned by way of example and by way of preference: cyclopropane-1,1-diyl, cyclobutane-1,1-diyl, cyclopentane-1,1-diyl and cyclohexane-1,1-diyl.

4- to 7-membered heterocyclyl and 4- to 6-membered heterocyclyl in the context of the invention represent a monocyclic saturated heterocycle having a total of 4 to 7 and 4 to 6 ring atoms, respectively, which contains one or two ring heteroatoms from the group consisting of N, O and S and is attached via a ring carbon atom or, if appropriate, via a ring nitrogen atom. Preference is given to 4- to 6-membered heterocyclyl having one or two ring heteroatoms from the group consisting of N and O. The following may be mentioned by way of example: azetidinyl, oxetanyl, pyrrolidinyl, pyrazolidinyl, tetrahydrofuranyl, piperidinyl, piperazinyl, tetrahydropyranyl, morpho-linyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

Halogen in the context of the invention includes fluorine, chlorine, bromine and iodine. Chlorine, fluorine and bromine are preferred, with fluorine and chlorine being particularly preferred.

An oxo substituent in the context of the invention represents an oxygen atom, which is bonded to a carbon atom via a double bond.

If radicals in the compounds according to the invention are substituted, the radicals can be mono- or polysubstituted, unless specified otherwise. In the context of the present invention, for all the radicals which occur several times, the meanings thereof are independent of each other. Substitution by one or by two or three identical or different substituents is preferred. Substitution by one or by two substituents is particularly preferred.

The present invention in particular provides compounds of the formula (I) in which ring A represents an oxo-substituted azaheterocycle of the formula

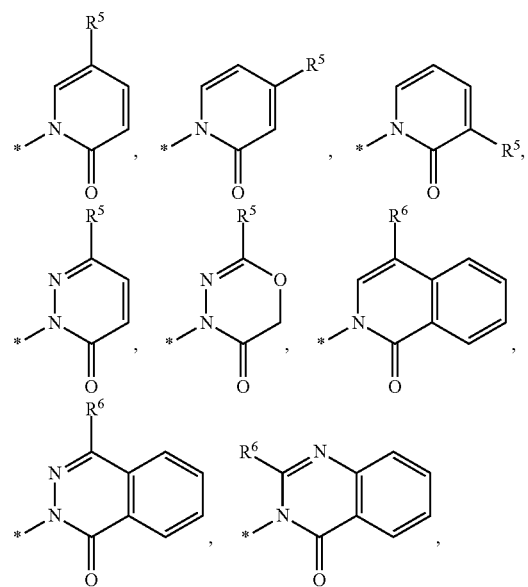

-continued

[chemical structures]

in which
* denotes the point of attachment to the remainder of the molecule,
$R^5$ represents chlorine, $(C_1-C_6)$-alkyl, trifluoromethyl, $(C_3-C_6)$-cycloalkyl, 4- to 6-membered heterocyclyl or phenyl, where phenyl for its part may be substituted up to two times by identical or different radicals selected from the group consisting of fluorine, chlorine, bromine, cyano, $(C_1-C_4)$-alkyl, vinyl, trifluoromethyl, $(C_1-C_4)$-alkoxy and trifluoromethoxy,
$R^6$ represents hydrogen or has the meaning of $R^5$ given above
and
$R^{7A}$ and $R^{7B}$ independently of one another represent hydrogen, fluorine or chlorine,
or a salt, solvate or solvate of a salt thereof.

In the context of the present invention, preference is given to compounds of the formula (I) in which
ring A represents an oxo-substituted azaheterocycle of the formula

[chemical structures]

in which
* denotes the point of attachment to the remainder of the molecule,
$R^5$ represents chlorine, $(C_1-C_6)$-alkyl, trifluoromethyl, $(C_3-C_6)$-cycloalkyl or phenyl, where phenyl for its part may be substituted up to two times by identical or different radicals selected from the group consisting of fluorine, chlorine, cyano, $(C_1-C_4)$-alkyl, trifluoromethyl, $(C_1-C_4)$-alkoxy and trifluoromethoxy,
$R^6$ represents hydrogen or has the meaning of $R^5$ given above
and
$R^{7A}$ and $R^{7B}$ independently of one another represent hydrogen, fluorine or chlorine,
$R^1$ represents hydrogen or $(C_1-C_4)$-alkyl,
$R^2$ represents hydrogen, fluorine, chlorine or trifluoromethyl,
$R^3$ represents $(C_3-C_6)$-alkyl or $(C_3-C_6)$-alkenyl, each of which may be substituted by cyano, methoxy, ethoxy or trifluoromethoxy and up to six times by fluorine,
or
represents $(C_3-C_6)$-cycloalkyl or $(C_4-C_6)$-cycloalkenyl, each of which may be substituted up to two times by identical or different radicals from the group consisting of methyl, ethyl and trifluoromethyl and also up to four times by fluorine,
or
represents oxetanyl,
and
L represents straight-chain $(C_3-C_6)$-alkanediyl or $(C_3-C_6)$-alkenediyl, each of which may be substituted up to four times by identical or different radicals $R^4$ where
$R^4$ represents fluorine, trifluoromethyl, methyl or ethyl
or
two radicals $R^4$ attached to the same carbon atom are linked to each other and together with this carbon atom form a cyclopropane-1,1-diyl or cyclobutane-1,1-diyl ring,
or a salt, solvate or solvate of a salt thereof.

In the context of the present invention, particular preference is given to compounds of the formula (I) in which
ring A represents an oxo-substituted azaheterocycle of the formula

[chemical structures]

in which
* denotes the point of attachment to the remainder of the molecule,
$R^5$ represents chlorine, trifluoromethyl or phenyl, where phenyl for its part may be substituted up to two times by identical or different radicals selected from the group consisting of fluorine, chlorine, methyl and trifluoromethyl, and R$^{7A}$ and R$^{7B}$ independently of one another represent hydrogen or fluorine, R$^1$ represents hydrogen, R$^2$ represents hydrogen, R$^3$ represents propan-2-yl, butan-2-yl, pentan-2-yl, 3,3,3-trifluoropropan-1-yl, 1,1,1-trifluoropropan-2-yl, 1,1,1-trifluorobutan-2-yl, 4,4,4-trifluorobutan-2-yl, 4,4,4-trifluoro-2-methylbutan-1-yl, cyclopentyl or 3,3-difluorocyclopentyl, and L represents straight-chain (C$_3$-C$_6$)-alkanediyl or (C$_3$-C$_6$)-alkenediyl, each of which may be substituted up to four times by identical or different radicals R$^4$ where R$^4$ represents methyl or two radicals R$^4$ attached to the same carbon atom are linked to each other and together with this carbon atom form a cyclopropane-1,1-diyl ring, or a salt, solvate or solvate of a salt thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds of the formula (I) according to the invention, characterized in that initially either

[A] a compound of the formula (II)

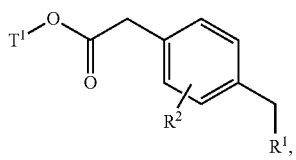

(II)

in which R$^1$ and R$^2$ have the meanings given above and T$^1$ represents (C$_1$-C$_4$)-alkyl, is converted in an inert solvent in the presence of a base with a compound of the formula (III)

R$^3$—X    (III), in which R$^3$ has the meaning given above and

X represents a leaving group such as, for example, halogen, mesylate, tosylate or triflate, into a compound of the formula (IV)

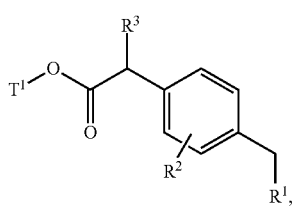

(IV)

in which R$^1$, R$^2$, R$^3$ and T$^1$ each have the meanings given above, or

[B] a compound of the formula (V)

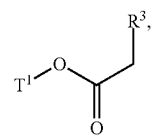

(V)

in which R$^3$ and T' have the meanings given above is, in an inert solvent, after deprotonation with a base, reacted with a compound of the formula (VI)

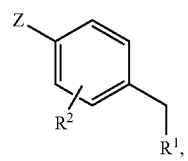

(VI)

in which R$^1$ and R$^2$ have the meanings given above and

Z represents chlorine, bromine or iodine, in the presence of a suitable palladium catalyst, likewise to give a compound of the formula (IV)

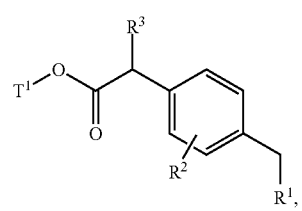

(IV)

in which R$^1$, R$^2$, R$^3$ and T$^1$ each have the meanings given above, the compound of the formula (IV) is then brominated in an inert solvent with elemental bromine or with N-bromosuccinimide to give a compound of the formula (VII)

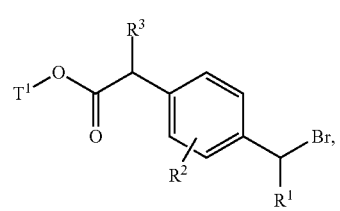

(VII)

in which R$^1$, R$^2$, R$^3$ and T$^1$ each have the meanings given above, and then reacted in an inert solvent in the presence of a base with a compound of the formula (VIII)

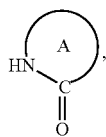
(VIII)

in which ring A represents an oxo-substituted azaheterocycle, as defined above,
to give a compound of the formula (IX)

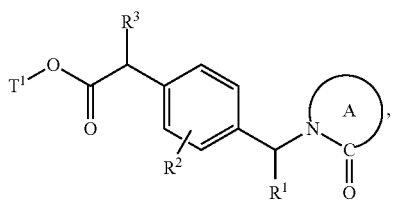
(IX)

in which ring A, $R^1$, $R^2$, $R^3$ and $T^1$ each have the meanings given above,
the ester radical $T^1$ in (IX) is then removed under basic or acidic conditions, the resulting carboxylic acid of the formula (X)

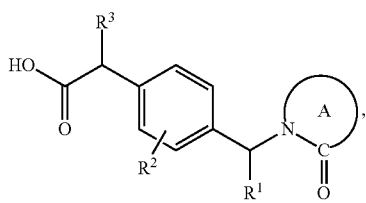
(X)

in which ring A, $R^1$, $R^2$ and $R^3$ each have the meanings given above,
is then coupled in an inert solvent in the presence of a condensing agent or via the intermediate of the corresponding carbonyl chloride in the presence of a base with an amine of the formula (XI)

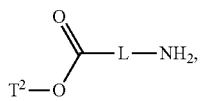
(XI)

in which L has the meaning given above
and
$T^2$ represents $(C_1-C_4)$-alkyl,
to give a compound of the formula (XII)

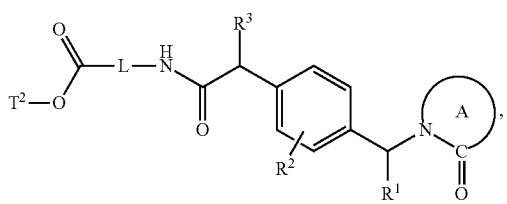
(XII)

in which ring A, $R^1$, $R^2$, $R^3$, L and $T^2$ each have the meanings given above, and the ester radical $T^2$ in (XII) is then removed by further basic or acidic solvolysis to give the carboxylic acid of the formula (I)
and the compounds of the formula (I) are separated where appropriate by methods known to the skilled person into their enantiomers and/or diastereomers, and/or where appropriate reacted with the appropriate (i) solvents and/or (ii) bases or acids to give the solvates, salts and/or solvates of the salts thereof.

In the reaction sequence described above, it may be expedient where appropriate to reverse the order of individual transformations. Thus, it is possible, for example, to convert the compound of the formula (VII-A) [$T^1$ in (VII)=tert-butyl]

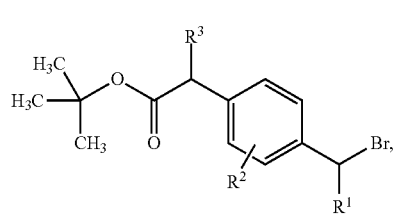
(VII-A)

in which $R^1$, $R^2$ and $R^3$ have the meanings given above,
initially by treatment with an acid into a carboxylic acid of the formula (XIII)

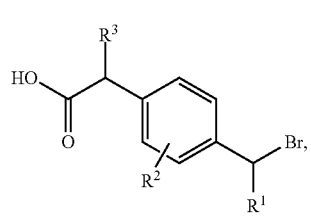
(XIII)

in which $R^1$, $R^2$ and $R^3$ have the meanings given above,
and then to couple this compound in an inert solvent in the presence of a condensing agent or via the intermediate of the corresponding carbonyl chloride in the presence of a base with an amine of the formula (XI)

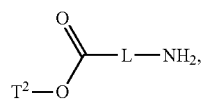
(XI)

in which L has the meaning given above
and
$T^2$ represents $(C_1-C_4)$-alkyl,
to give a compound of the formula (XIV)

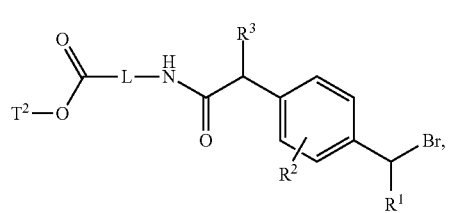
(XIV)

in which $R^1$, $R^2$, $R^3$, L and $T^2$ each have the meanings given above, which is then reacted in an inert solvent in the presence of a base with a compound of the formula (VIII)

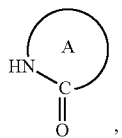
(VIII)

in which ring A represents an oxo-substituted azaheterocycle, as described above,
to give the compound of the formula (XII)

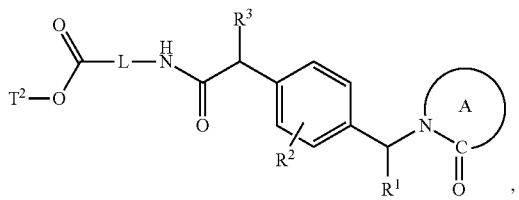
(XII)

in which ring A, $R^1$, $R^2$, $R^3$, L and $T^2$ each have the meanings given above,
and converted by removal of the ester radical $T^2$ in (XII) into the carboxylic acid of the formula (I).

Separation of the compounds of the invention into the corresponding enantiomers and/or diastereomers can take place where appropriate, depending on expediency, even at the stage of the compounds (IX), (X) or (XII), which are then reacted further in separated form in accordance with the above described process sequences. Such a fractionation of the stereoisomers can be carried out by conventional methods known to the skilled person; chromatographic methods or separation via diastereomeric salts are preferably used.

Inert solvents for the process step (II)+(III)→(IV) are, for example, ethers such as diethyl ether, methyl tert-butyl ether, dioxane, tetrahydrofuran, glycol dimethyl ether or diethylene glycol dimethyl ether, hydrocarbons such as benzene, toluene, xylene, hexane, cyclohexane or mineral oil fractions, or dipolar aprotic solvents such as dimethylformamide (DMF), dimethyl sulfoxide (DMSO), N,N'-dimethylpropyleneurea (DMPU) or N-methylpyrrolidinone (NMP). It is also possible to use mixtures of the solvents mentioned. Preference is given to using tetrahydrofuran, dimethylformamide or mixtures of these.

Suitable bases for the process step (II)+(III)→(IV) are customary strong inorganic or organic bases. These include in particular alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, or amides such as lithium bis(trimethylsilyl)amide, sodium bis(trimethylsilyl)amide or potassium bis(trimethylsilyl)-amide or lithium diisopropylamide. Preference is given to using potassium tert-butoxide, sodium hydride or lithium diisopropylamide.

The reaction (II)+(III)→(IV) is generally carried out in a temperature range of from −100° C. to +30° C., preferably at from −78° C. to 0° C.

The ester arylation in process step (V)+(VI)→(IV) is preferably carried out in toluene or toluene/tetrahydrofuran mixtures in a temperature range of from +20° C. to +100° C. A base particularly suitable for the deprotonation in this reaction is lithium bis(trimethylsilyl)amide. Suitable palladium catalysts are, for example, palladium(II) acetate or tris(dibenzylideneacetone)-dipalladium in combination with electron-rich, sterically demanding phosphine ligands such as 2-dicyclohexylphosphino-2'-(N,N-dimethylamino)biphenyl or 2-di-tert-butylphosphino-2'-(N,N-dimethylamino)biphenyl [cf., for example, W. A. Moradi, S. L. Buchwald, J. Am. Chem. Soc. 123, 7996-8002 (2001)].

The bromination in process step (IV)→(VII) is preferably carried out in a halogenated hydrocarbon as solvent, in particular in dichloromethane or carbon tetrachloride, in a temperature range of from +40° C. to +100° C. Suitable brominating agents are elemental bromine in the presence of light and also in particular N-bromosuccinimide (NBS) with addition of α,α'-azobis(iso-butyronitrile) (AIBN) or dibenzoyl peroxide as initiator [cf., for example, R. R. Kurtz, D. J. Houser, J. Org. Chem. 46, 202 (1981); Z.-J. Yao et al., Tetrahedron 55, 2865 (1999)].

Inert solvents for the process steps (VII)+(VIII)→(IX) and (XIV)+(VIII)→(XII) are, for example, ethers such as diethyl ether, methyl tert-butyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, chlorobenzene or chlorotoluene, or other solvents such as dimethylformamide (DMF), dimethyl sulfoxide (DMSO), N,N'-dimethylpropyleneurea (DMPU), N-methylpyrroli-dinone (NMP), acetonitrile or pyridine. It is also possible to use mixtures of the solvents mentioned. Preference is given to using tetrahydrofuran, dimethylformamide or mixtures of these.

Suitable bases for these reactions are the customary inorganic or organic bases. These include in particular alkali metal hydroxides such as, for example, lithium hydroxide, sodium hydroxide or potassium hydroxide, alkali metal carbonates such as lithium carbonate, sodium carbonate, potassium carbonate or cesium carbonate, alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, or amides such as lithium bis(trimethylsilyl)amide, sodium bis(trimethylsilyl)amide or potassium bis(trimethyl-silyl)amide or lithium diisopropylamide. Preference is given to using cesium carbonate or sodium hydride.

The reactions (VII)+(VIII)→(IX) and (XIV)+(VIII)→(XII) are generally carried out in a temperature range of from −20° C. to +120° C., preferably in the range from 0° C. to +80° C.

The removal of the ester group $T^1$ or $T^2$ in the process steps (IX)→(X), (XII)→(I) and (VII-A)→(XIII) is carried out by customary methods by treating the esters in inert solvents with acids or bases, where in the latter case the salts initially formed are converted by treatment with acid into the free carboxylic acids. In the case of the tert-butyl esters, the ester hydrolysis is preferably carried out using acids.

Suitable inert solvents for these reactions are water or the organic solvents customary for an ester hydrolysis. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichloromethane, dimethylformamide or dimethyl sulfoxide. It is also possible to use mixtures of the solvents mentioned. In the case of a basic ester hydrolysis, preference is given to using mixtures of water with dioxane, tetrahydrofuran, methanol and/or ethanol. In the case of the reaction with trifluoroacetic acid, preference is given to using dichloromethane, and in the case of the reaction with hydrogen chloride, preference is given to using tetrahydrofuran, diethyl ether, dioxane or water.

Suitable bases are the customary inorganic bases. These include in particular alkali metal or alkaline earth metal hydroxides such as, for example, lithium hydroxide, sodium hydroxide, potassium hydroxide or barium hydroxide, or alkali metal or alkaline earth metal carbonates such as sodium carbonate, potassium carbonate or calcium carbonate. Preference is given to lithium hydroxide, sodium hydroxide or potassium hydroxide.

Suitable acids for the ester hydrolysis are in general sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, if appropriate with addition of water. Preference is given to hydrogen chloride or trifluoroacetic acid in the case of the tert-butyl esters and hydrochloric acid in the case of the methyl esters.

The ester hydrolysis is generally carried out in a temperature range of from −20° C. to +100° C., preferably at from 0° C. to +60° C.

Inert solvents for the process steps (X)+(XI)→(XII) and (XIII)+(XI)→(XIV) [amide coupling] are, for example, ethers such as diethyl ether, tert-butyl methyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, acetonitrile, ethyl acetate, pyridine, dimethyl sulfoxide (DMSO), dimethylformamide (DMF), N,N'-dimethylpropyleneurea (DMPU) or N-methylpyrrolidinone (NMP). It is also possible to use mixtures of the solvents mentioned. Preference is given to dichloromethane, tetrahydrofuran, dimethylformamide or mixtures of these solvents.

Suitable condensing agents for these coupling reactions are, for example, carbodiimides such as N,N'-diethyl-, N,N'-dipropyl-, N,N'-diisopropyl-, N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride, diethyl cyanophosphonate, bis(2-oxo-3-oxazolidinyl)phosphoryl chloride, benzotriazol-1-yloxy-tris(dimethylamino)phosphonium hexafluorophosphate, benzotriazol-1-yloxy-tris(pyrrolidi-no)phosphonium hexafluorophosphate (PyBOP), O-(benzotriazol-1-yl)-N,N,N',N'-tetramethyl-uronium tetrafluoroborate (TBTU), O-(benzotriazol-1-yl)-N,N,N'N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), if appropriate in combination with further auxiliaries such as 1-hydroxybenzotriazole (HOBt) or N-hydroxysuccinimide (HOSu), and as bases alkali metal carbonates, for example sodium carbonate or potassium carbonate, or organic bases such as triethylamine, N-methylmorpholine, N-methyl-piperidine, N,N-diisopropylethylamine, pyridine or 4-N,N-dimethylaminopyridine. Preference is given to using O-(7-azabenzotriazol-1-yl)-N,N,N',N'-tetramethyluronium hexafluorophosphate (HATU) or O-(benzotriazol-1-yl)-N,N,N',N'-tetramethyluronium tetrafluoroborate (TBTU), in each case in combination with pyridine or N,N-diisopropylethylamine, or N-(3-dimethylaminoisopropyl)-N'-ethylcarbodiimide hydrochloride (EDC) in combination with 1-hydroxybenzotriazole (HOBt) and triethylamine The couplings (X)+(XI)→(XII) and (XIII)+(XI)→(XIV) are generally carried out in a temperature range of from 0° C. to +60° C., preferably at from +10° C. to +40° C.

When a carbonyl chloride corresponding to the compound (X) or (XIII) is used, the coupling with the amine component (XI) is carried out in the presence of a customary organic auxiliary base such as triethylamine, N-methylmorpholine, N-methylpiperidine, N,N-diisopropylethylamine, pyridine, 4-N,N-dimethylaminopyridine, 1,8-diazabicyclo[5.4.0]undec-7-ene (DBU) or 1,5-diazabicyclo-[4.3.0]non-5-ene (DBN). Preference is given to using triethylamine or N,N-diisopropylethylamine.

The reaction of the amine (XI) with the carbonyl chloride is generally carried out in a temperature range of from −20° C. to +60° C., preferably in the range from 0° C. to +40° C.

For their part, the preparation of the carbonyl chlorides is carried out in a customary manner by treating the carboxylic acids (X) or (XIII) with thionyl chloride.

The reactions mentioned can be carried out at atmospheric, at elevated or at reduced pressure (for example from 0.5 to 5 bar). In general, they are in each case carried out at atmospheric pressure.

The compounds of the formulae (II), (III), (V), (VI), (VIII) and (XI) are commercially available, described as such in the literature or can be prepared analogously to customary processes known from the literature [for compounds of the formula (XI) see also Synthesis Schemes 3-5 below].

The preparation of the compounds of the invention can be illustrated in an exemplary manner by the following reaction schemes:

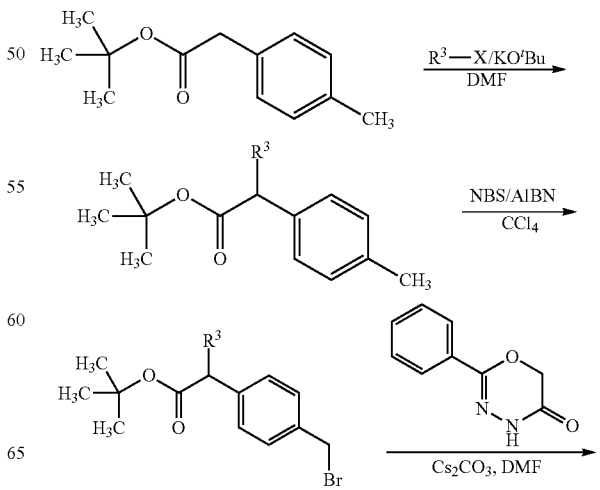

17
-continued
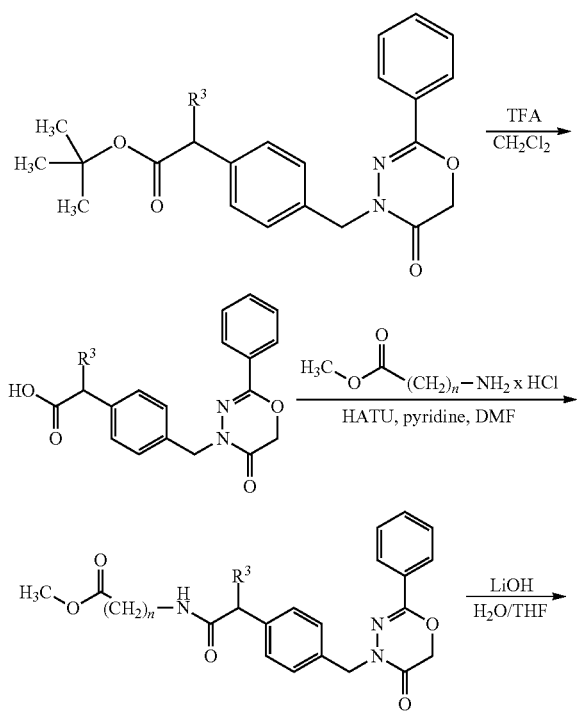
Scheme 2
18
-continued
Scheme 3
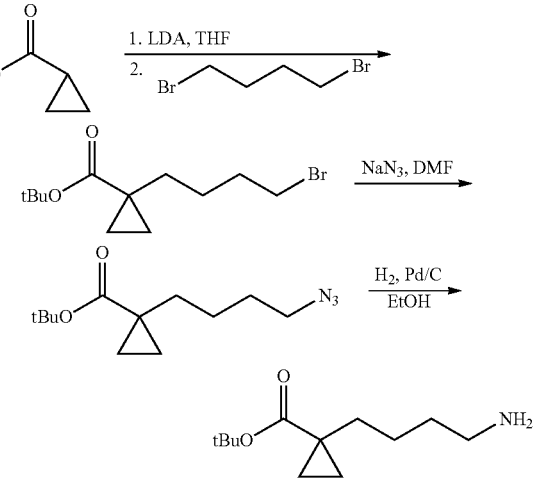
Scheme 4
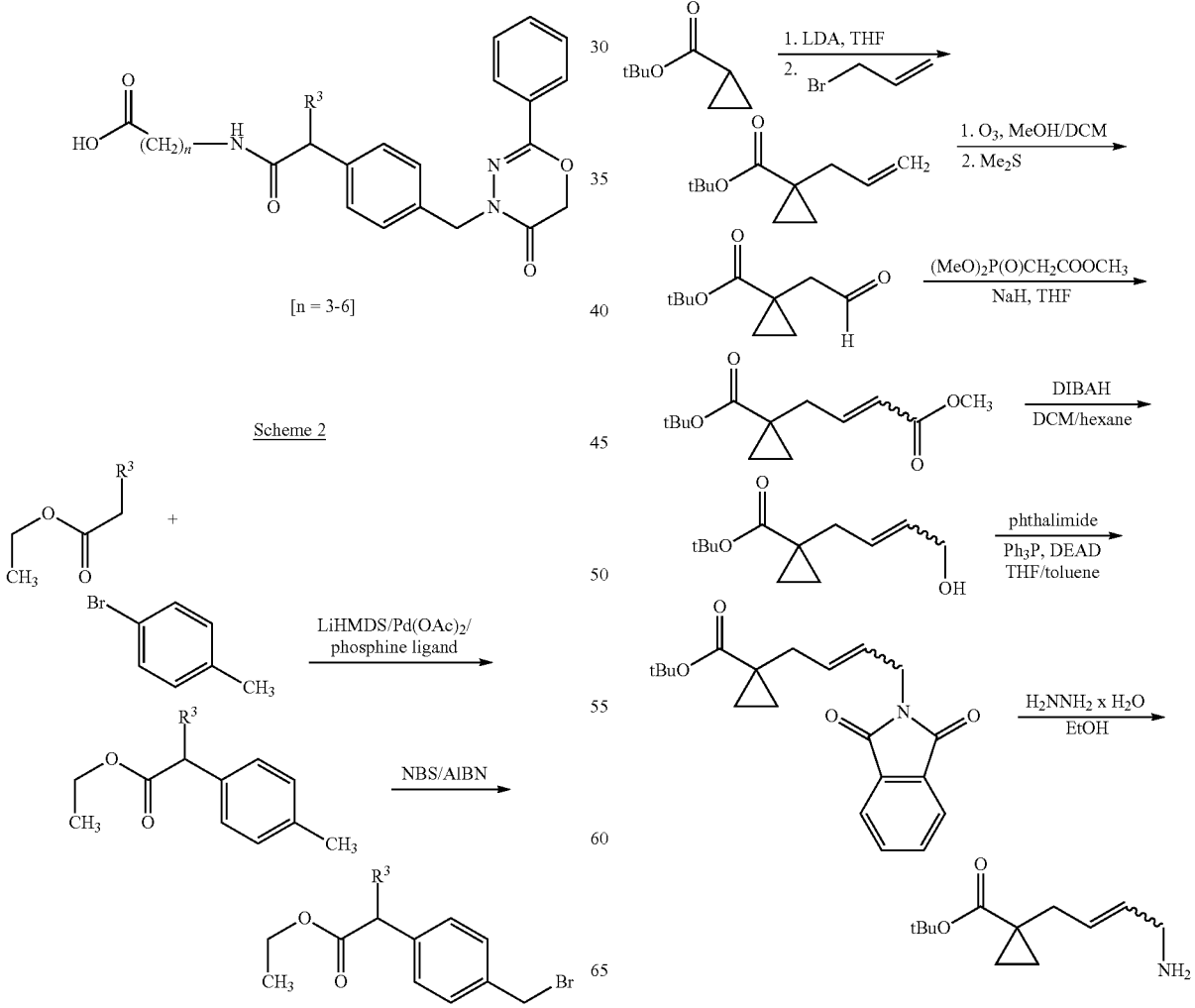

Scheme 5

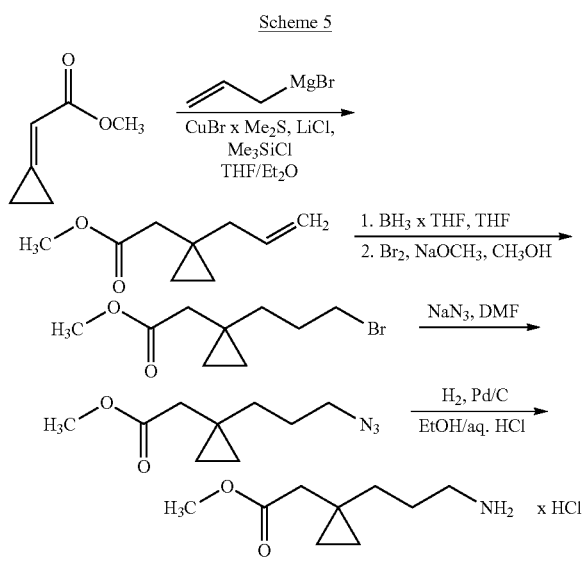

The compounds according to the invention have valuable pharmacological properties and can be used for the prevention and treatment of disorders in humans and animals.

The compounds according to the invention are potent activators of soluble guanylate cyclase. They lead to vasorelaxation, inhibition of platelet aggregation and lowering of blood pressure and increase of coronary blood flow. These effects are mediated via direct heme-independent activation of soluble guanylate cyclase and an increase of intracellular cGMP.

The compounds according to the invention can therefore be employed in medicaments for the treatment of cardiovascular disorders such as, for example, for the treatment of high blood pressure and heart failure, stable and unstable angina pectoris, pulmonary hypertension, renal hypertension, peripheral and cardiac vascular disorders, arrhythmias, for the treatment of thromboembolic disorders and ischemias such as myocardial infarction, stroke, transistory and ischemic attacks, disturbances of peripheral blood flow, prevention of restenoses as after thrombolysis therapies, percutaneous transluminal angioplasties (PTAs), percutaneous transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, and incontinence, osteoporosis, glaucoma, and gastroparesis.

The compounds according to the invention can additionally be used for the treatment of primary and secondary Raynaud's phenomenon, of microcirculation impairments, claudication, peripheral and autonomic neuropathies, diabetic microangiopathies, diabetic retinopathy, diabetic ulcers on the extremities, CREST syndrome, erythematosis, onychomycosis and rheumatic disorders.

In addition, the compounds according to the invention can be used for preventing ischemia- and/or reperfusion-related damage to organs or tissues and also as additives for perfusion and preservation solutions of organs, organ parts, tissues or tissue parts of human or animal origin in particular for surgical interventions or in the field of transplantation medicine.

The compounds according to the invention are furthermore suitable for the treatment of respiratory distress syndromes and chronic obstructive airway disorders (COPD), of acute and chronic renal failure and for promoting wound healing.

The compounds described in the present invention also represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions (Apoplexia cerebri) such as stroke, cerebral ischemias and craniocerebral trauma. The compounds according to the invention can likewise be employed for controlling states of pain.

In addition, the compounds according to the invention have an anti-inflammatory effect and can therefore be employed as anti-inflammatory agents.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to the use of the compounds according to the invention in a method for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prevention of the aforementioned disorders. Examples of suitable combination active ingredients which may be preferably mentioned are:
  organic nitrates and NO donors such as, for example, sodium nitroprusside, nitroglycerin, isosorbide mononitrate, isosorbide dinitrate, molsidomine or SIN-1, and inhaled NO;
  compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;

NO-independent but heme-dependent stimulators of guanylate cyclase, such as, in particular, the compounds described in WO 00/06568, WO 00/06569, WO 02/42301 and WO 03/095451;

agents having antithrombotic activity, for example and preferably from the group of platelet aggregation inhibitors, of anticoagulants or of profibrinolytic substances;

active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or active ingredients which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidin or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide.

Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein (a) antagonists.

In a preferred embodiment of the invention, the compounds according to the invention are administered in combination with a CETP inhibitor such as, for example and preferably, torcetrapib (CP-529 414), JJT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin, or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, Cholesta-Gel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonary, nasal, sublingual, lingual, buccal, rectal, dermal, transdermal, conjunctival, otic routes or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions or spray, tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral and intravenous administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations and Acronyms abs. absolute
Ac acetyl
AIBN 2,2'-azobis(2-methylpropionitrile)
aq. aqueous, aqueous solution
ATP adenosine 5'-triphosphate
Brij® polyethylene glycol dodecyl ether BSA bovine serum albumin
Bu butyl
c concentration
CI chemical ionization (in MS)
d day(s)
DBU 1,8-diazabicyclo[5.4.0]undec-7-ene
DCI direct chemical ionization (in MS)
DCM dichloromethane
de diastereomeric excess
DEAD diethyl azodicarboxylate
DIBAH diisobutylaluminum hydride
DIEA diisopropylethylamine
DMF dimethylformamide
DMSO dimethyl sulfoxide
DTT dithiothreitol
EDC N'-(3-dimethylaminopropyl)-N-ethylcarbodiimide hydrochloride
ee enantiomeric excess
EI electron impact ionization (in MS)
ent enantiomerically pure, enantiomer
eq. equivalent(s)
ESI electrospray ionization (in MS)
Et ethyl
Ex. example
GC gas chromatography
GTP guanosine 5'-triphosphate
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high pressure, high performance liquid chromatography
$^i$Pr isopropyl
KO$^t$Bu potassium tert-butoxide
LC-MS liquid chromatography-coupled mass spectrometry
LDA lithium diisopropylamide
LiHDMS lithium hexamethyldisilazide [lithium bis(trimethylsilyl)amide]
Me methyl
min minute(s)
MS mass spectroscopy
NBS N-bromosuccinimide
NMR nuclear magnetic resonance spectrometry
Pd/C palladium on activated carbon
PDC pyridinium dichromate
Ph phenyl
Pr propyl
rac racemic, racemate
$R_f$ retention index (in TLC)
RP reversed phase (in HPLC)
RT room temperature
$R_t$ retention time (in HPLC)
$^t$Bu tert-butyl
TBTU O-(benzotriazol-1-3H)—N,N,N',N'-tetramethyluronium tetrafluoroborate
TCTU O-(1H-6-chlorobenzotriazol-1-yl)-1,1,3,3-tetramethyluronium tetrafluoroborate
TEA triethanolamine
TFA trifluoroacetic acid
THF tetrahydrofuran
TLC thin-layer chromatography
UV ultraviolet spectroscopy GC-MS and LC-MS Methods:
Method 1 (GC-MS)
Instrument: Micromass GCT, GC 6890; column: Restek RTX-35, 15 m×200 μm×0.33 μm; constant helium flow rate: 0.88 ml/min; oven: 70° C.; inlet: 250° C.; gradient: 70° C., 30° C./min→310° C. (maintain for 3 min)
Method 2 (LC-MS)
MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.
Method 3 (LC-MS)
Instrument: Micromass Quattro Premier with Waters HPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient 0.0 min 90% A→0.1 min 90% A→1.5 min 10% A→2.2 min 10% A; flow rate: 0.33 ml/min; oven: 50° C.; UV detection: 210 nm.
Method 4 (LC-MS)
MS instrument type: Micromass ZQ; HPLC instrument type: HP 1100 Series; UV DAD; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 5 (LC-MS)
Instrument: Waters Acquity SQD HPLC System; column: Waters Acquity HPLC HSS T3 1.8μ, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.
Method 6 (LC-MS)
MS instrument type: Waters Micromass Quattro Micro; HPLC instrument type: Agilent 1100 Series; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.
Starting Materials and Intermediates:

Example 1A tert-Butyl Cyclopropanecarboxylate

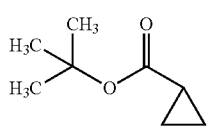

50.99 g (454.4 mmol) of potassium tert-butoxide were dissolved in 454 ml of abs. THF and cooled to 0° C. The solution was stirred vigorously, and 50 g (478.3 mmol) of cyclopropanecarbonyl chloride were added dropwise such that the reaction temperature did not exceed 50° C. (cooling required). After the addition has ended, the resultant suspension was stirred for another 30 min. After cooling, the reaction mixture was, under reduced pressure, concentrated to about one third of the original volume and then added to 2 liters of saturated aqueous ammonium chloride solution. The pH was adjusted to 8 by addition of saturated sodium bicarbonate solution and the mixture was then extracted three times with diethyl ether. The combined organic phases were dried over magnesium sulfate and concentrated under reduced pressure without heating (cold water bath). The residue was distilled at a bath temperature of about 85° C. and 42 mbar. This gave 43.1 g (63.2% of theory) of the target compound as a clear liquid.

GC-MS (Method 1): $R_t$=1.8 min $^1$H-NMR (400 MHz, DMSO-$d_6$): δ=1.52-1.48 (m, 1H), 1.41 (s, 9H), 0.82-0.72 (m, 4H).

Example 2A

Tert-Butyl 1-(4-bromobutyl)cyclopropanecarboxylate

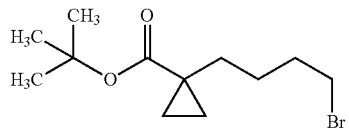

21.2 ml (52.7 mmol) of a 2.5 M solution of n-butyllithium in n-hexane were added dropwise to a solution, cooled to −78° C., of 7.4 ml (52.7 mmol) of diisopropylamine in 20 ml of abs. THF. During the addition, the reaction temperature was kept below −60° C. After 30 min of stirring at −60° C. to −70° C., this solution was added dropwise to a solution, cooled to −78° C., of 5.0 g (35.2 mmol) of tert-butyl cyclopropanecarboxylate and 15.2 g (70.3 mmol) of 1,4-dibromobutane in 20 ml of abs. THF. After the end of the addition, cooling was removed and the mixture was slowly warmed to RT with stirring. After a further 5 h of stirring at RT, the reaction mixture was added to saturated aqueous ammonium chloride solution. The mixture was extracted three times with dichloromethane. The combined organic phases were dried over magnesium sulfate and concentrated under reduced pressure. The product was purified by chromatography on silica gel (mobile phase cyclohexane/dichloromethane 50:1). This gave 4.62 g (44.6% of theory) of the target compound.

MS (DCI): m/z=294/296 (M+NH$_4$)$^+$.

GC-MS (Method 1): $R_t$=4.70 min; m/z=220 (M-C$_4$H$_8$)$^+$.

$^1$H-NMR (400 MHz, DMSO-$d_6$): δ=3.54 (t, 2H), 1.72-1.65 (m, 2H), 1.57-1.42 (m, 4H), 1.39 (s, 9H), 0.98 (m, 2H), 0.66 (m, 2H).

Example 3A

Tert-Butyl 6-bromo-2,2-dimethylhexanoate

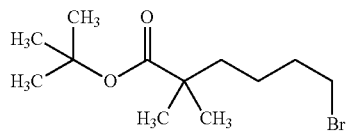

The title compound was obtained in a manner analogous to Example 2A from tert-butyl 2-methylpropanoate and 1,4-dibromobutane.

GC-MS (Method 1): $R_t$=4.25 min; m/z=205 (M-75)$^+$.

$^1$H-NMR (400 MHz, DMSO-$d_6$): δ=3.54 (t, 2H), 1.81-1.72 (m, 2H), 1.49-1.39 (m, 2H), 1.40 (s, 9H), 1.35-1.28 (m, 2H), 1.08 (s, 6H).

Example 4A

Tert-Butyl(+/−)-1-(4-bromopentyl)cyclopropanecarboxylate

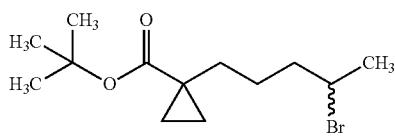 [SMILES: CC(Br)CCCC1(C(=O)OC(C)(C)C)CC1]

21.2 ml (52.7 mmol) of a 2.5 M solution of n-butyllithium in n-hexane were added dropwise to a solution, cooled to −78° C., of 7.4 ml (52.7 mmol) of diisopropylamine in 20 ml of abs. THF. During the addition, the reaction temperature was kept below −60° C. After 30 min of stirring at −60° C. to −70° C., this solution was added dropwise to a solution, cooled to −78° C., of 5.0 g (35.2 mmol) of tert-butyl cyclopropanecarboxylate and 16.2 g (70.3 mmol) of 1,4-dibromopentane in 20 ml of abs. THF. After the end of the addition, cooling was removed and the mixture was slowly warmed to RT with stirring. After a further 4 h of stirring at RT, the reaction mixture was added to saturated aqueous ammonium chloride solution. The mixture was extracted three times with dichloromethane. The combined organic phases were dried over magnesium sulfate and concentrated under reduced pressure. The product was purified by chromatography on silica gel (mobile phase gradient cyclohexane/dichloromethane 50:1 to 5:1). This gave, in two batches, in total 5.73 g (53.6% of theory) of the target compound.

MS (DCI): m/z=308/310 (M+NH$_4$)$^+$.

GC-MS (Method 1): $R_t$=4.82 min; m/z=234 (M-C$_4$H$_8$)$^+$.

$^1$H-NMR (400 MHz, DMSO-$d_6$): δ=4.29 (q, 1H), 1.78-1.71 (m, 2H), 1.67 (d, 3H), 1.65-1.43 (m, 4H), 1.39 (s, 9H), 0.98 (m, 2H), 0.67 (m, 2H).

General Procedure 1: Preparation of Azides from Aliphatic Bromides

At RT, excess sodium azide (about 4-6 eq.) is added to a solution of the appropriate bromide in DMF (about 0.2 to 1 mol/l). The suspension is stirred vigorously at 50-80° C. for 2-18 h. After cooling to RT, the reaction mixture is diluted (for example with ethyl acetate or dichloromethane) and washed successively with saturated sodium bicarbonate solution and saturated sodium chloride solution. After careful concentration under reduced pressure, the crude product may, if required, be purified by chromatography on silica gel (typical mobile phase mixture, for example, cyclohexane/ethyl acetate 100:1 to 10:1).

The following examples were prepared according to General Procedure 1:

| Example | Structure | Analytical data |
|---|---|---|
| 5A | H₃C–O–C(=O)–(CH₂)₅–N₃ (ethyl 6-azidohexanoate) | GC-MS (Method 1): R_t = 4.01 min; m/z = 157<br>MS (DCI): m/z = 203 (M + NH₄)⁺, 186 (M + H)⁺<br>¹H-NMR (400 MHz, DMSO-d₆): δ = 4.05 (q, 2H), 3.22 (t, 2H), 2.29 (t, 2H), 1.58-1.49 (m, 4H), 1.47-1.39 (m, 2H), 1.18 (t, 3H). |
| 6A | tert-butyl 1-(4-azidobutyl)cyclopropanecarboxylate | GC-MS (Method 1): R_t = 4.63 min; m/z = 154<br>MS (DCI): m/z = 240 (M + H)⁺<br>¹H-NMR (400 MHz, DMSO-d₆): δ = 3.31 (m, 2H), 1.55-1.42 (m, 6H), 1.39 (s, 9H), 0.98 (m, 2H), 0.65 (m, 2H). |
| 7A | tert-butyl 6-azido-2,2-dimethylhexanoate | ¹H-NMR (400 MHz, DMSO-d6): δ = 3.32 (t, 2H), 1.53-1.41 (m, 4H), 1.39 (s, 9H), 1.30-1.20 (m, 2H), 1.06 (s, 6H). |
| 8A | tert-butyl 1-(4-azidopentyl)cyclopropanecarboxylate | GC-MS (Method 1): R_t = 4.74 min; m/z = 154<br>MS (DCI): m/z = 254 (M + H)⁺<br>¹H-NMR (400 MHz, DMSO-d₆): δ = 3.54 (q, 1H), 1.51-1.40 (m, 6H), 1.39 (s, 9H), 1.19 (d, 3H), 0.98 (m, 2H), 0.67 (m, 2H). |

Example 9A

Ethyl(+/−)-6-azido-2-methylhexanoate

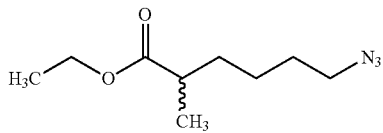

0.91 ml (2.28 mmol) of a 2.5 M solution of n-butyllithium in n-hexane was added dropwise to a solution, cooled to −78° C., of 0.32 ml (2.28 mmol) diisopropylamine in 2 ml abs. THF. During the addition, the reaction temperature was kept below −60° C. After 30 min of stirring at −60° C. to −70° C., this solution was added dropwise to a solution, cooled to −78° C., of 352 mg (1.9 mmol) of ethyl 6-azidohexanoate in 2 ml of abs. THF. After the end of the addition, the mixture was warmed to −20 C and stirred for another 20 min, and 0.18 ml (2.85 mmol) of methyl iodide were then added dropwise. After the end of the addition, the mixture was slowly warmed to RT and stirred for a further 2 h. The reaction mixture was then added to saturated aqueous ammonium chloride solution. The mixture was extracted three times with dichloromethane, and the combined organic phases were dried over magnesium sulfate and concentrated under reduced pressure. The product was purified by chromatography on silica gel (mobile phase cyclohexane/dichloromethane 60:1). This gave 96.4 mg (25.5% of theory) of the target compound.

MS (DCI): m/z=200 (M+H)⁺.

GC-MS (Method 1): R_t=4.05 min.

¹H-NMR (400 MHz, DMSO-d₆): δ=4.05 (q, 2H), 3.31 (t, 2H), 2.45-2.39 (m, 1H), 1.58-1.49 (m, 4H), 1.34-1.28 (m, 2H), 1.19 (t, 3H), 1.07 (d, 3H).

Example 10A

Tert-Butyl 1-[4-(1,3-dioxo-1,3-dihydro-2H-isoindol-2-yl)butyl]cyclopropanecarboxylate

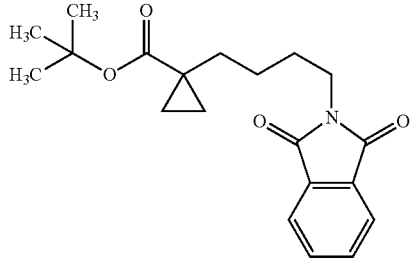 [SMILES: CC(C)(C)OC(=O)C1(CCCCN2C(=O)c3ccccc3C2=O)CC1]

Under argon, 4.2 g (15.15 mmol) of tert-butyl 1-(4-bromobutyl)cyclopropanecarboxylate were initially charged in 50 ml of DMF, 3.34 g (22.72 mmol) of phthalimide and 4.19 g (30.3 mmol) of potassium carbonate were added and the mixture was stirred at 90° C. for 2 h. The reaction mixture was then filtered, and the filtrate was diluted with water and extracted three times with ethyl acetate. The combined organic phases were dried over magnesium sulfate and concentrated under reduced pressure. The product was purified by chromatography on silica gel (mobile phase cyclohexane/ ethyl acetate 10:1). This gave 4.23 g (81.3% of theory) of the target compound.

LC-MS (Method 2): R_t=2.46 min; m/z=342 (M−H)⁻.

$^1$H-NMR (400 MHz, DMSO-$d_6$): δ=7.86 (m, 4H), 3.57 (t, 2H), 1.56 (m, 2H), 1.40 (m, 4H), 1.27 (s, 9H), 0.94 (q, 2H), 0.64 (q, 2H).

Example 11A

Tert-Butyl 6-oxoheptanoate

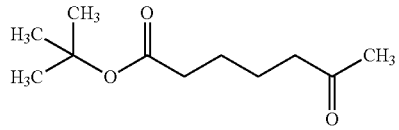

10.0 g (about 90% pure, 62.4 mmol) of 6-oxoheptanoic acid were initially charged in 71.8 ml of cyclohexane, and 20.46 g (93.6 mmol) of tert-butyl 2,2,2-trichloroacetimidate and 15 ml of dichloromethane were added. At –10° C. 0.55 ml (6.24 mmol) of trifluoromethanesulfonic acid were slowly added dropwise to the solution. The resulting suspension was stirred overnight with warming to RT. The insoluble precipitate was then removed by filtration. The filtrate was washed twice with sodium bicarbonate solution and with saturated sodium chloride solution, dried over magnesium sulfate and concentrated under reduced pressure. The residue was purified by chromatography on silica gel (mobile phase cyclohexane/ethyl acetate 5:1). On standing overnight, a solid precipitated from the product obtained in this manner. This solid was removed by filtration with suction and discarded. The target product, obtained in the form of the filtrate, was not purified any further. This gave 4.51 g (36.1% of theory) of the title compound.

GC-MS (Method 1): $R_t$=4.1 min; m/z=144 (M-$C_4H_8$)$^+$.
MS (DCI): m/z=218 (M+NH$_4$)$^+$.
$^1$H-NMR (400 MHz, DMSO-$d_6$): δ=2.46-2.42 (m, 2H), 2.20-2.15 (m, 2H), 2.08 (s, 3H), 1.47-1.40 (m, 4H), 1.41 (s, 9H).

Example 12A

Tert-Butyl(+/−)-6-aminoheptanoate

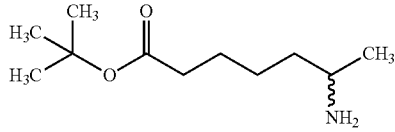

At RT, 7.70 g (99.86 mmol) of ammonium acetate and 941 mg (14.98 mmol) of sodium cyano-borohydride were added to a solution of 2.0 g (9.99 mmol) of tert-butyl 6-oxoheptanoate in 10 ml of methanol. The mixture was stirred at RT overnight and then added to water. Using 10% strength aqueous sodium hydroxide solution, the pH was adjusted to about 10, and the mixture was extracted three times with ethyl acetate. The organic phases were combined, dried over magnesium sulfate and concentrated under reduced pressure. Drying under high vacuum gave 1.95 g (about 80% pure, about 78% of theory) of the target compound.

MS (DCI): m/z=202 (M+H)$^+$.
$^1$H-NMR (500 MHz, DMSO-$d_6$): δ=2.95-2.89 (m, 1H), 2.19 (t, 2H), 1.52-1.43 (m, 2H), 1.41 (s, 9H), 1.35-1.25 (m, 4H), 1.04 (d, 3H).

General Procedure 2: Reduction of Azides to Primary Amines

Hydrogenation catalyst (for example 5% or 10% palladium on carbon) is added to a solution of the appropriate azide in ethanol or methanol (if appropriate with addition of water). The reaction mixture is stirred vigorously under an atmosphere of hydrogen at atmospheric pressure until the reaction has gone to completion and then filtered off through kieselguhr. The filter residue is washed with ethanol or methanol, the filtrates obtained are combined and carefully concentrated under reduced pressure and the residue is briefly dried under high vacuum. The amine obtained in this manner can be used without further purification for the subsequent reactions.

The following examples were prepared according to General Procedure 2:

| Example | Structure | Analytical data |
| --- | --- | --- |
| 13A | ![structure] | GC-MS (Method 1): $R_t$ = 3.63 min; m/z = 173 (M)$^+$<br>$^1$H-NMR (400 MHz, DMSO-$d_6$): δ = 4.04 (q, 2H), 3.15 (br. s, 2H), 2.39 (q, 1H), 1.57-1.21 (m, 6H), 1.19 (t, 3H), 1.05 (d, 3H). |
| 14A | ![structure] | MS (DCI): m/z = 216 (M + H)$^+$. |
| 15A | ![structure] | GC-MS (Method 1): $R_t$ = 4.31 min; m/z = 171 (M – $C_4H_8$)$^+$. |

| Example | Structure | Analytical data |
|---|---|---|
| 16A | 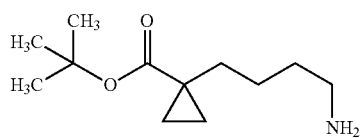 | MS (DCI): m/z = 214 (M + H)⁺. |

Example 16A

Tert-Butyl 1-(4-aminobutyl)cyclopropanecarboxylate

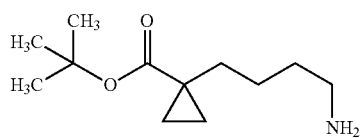

Alternative to the above process, the title compound could also be prepared from tert-butyl 1-[4-(1,3-dioxo-1,3-dihydro-2H-isoindol-2-yl)butyl]cyclopropanecarboxylate:

At RT, 0.29 g (5.8 mmol) of hydrazine hydrate was added to a solution of 1.0 g (2.91 mmol) of tert-butyl 1-[4-(1,3-dioxo-1,3-dihydro-2H-isoindol-2-yl)butyl]cyclopropanecarboxylate in 20 ml of ethanol. The mixture was stirred under reflux for 45 min. The reaction mixture was then filtered and the filtrate was concentrated at 20° C. on a rotary evaporator. The residue was taken up in dichloromethane and washed twice with saturated aqueous sodium bicarbonate solution. The organic phase was dried over magnesium sulfate and concentrated at 20° C. under reduced pressure. This gave 0.6 g (97.2% of theory) of the target compound. The substance was stored at −20° C. or directly reacted further.

GC-MS (Method 1): $R_t$=4.2 min; m/z=138.
MS (DCI): m/z=214 (M+H)⁺.
¹H-NMR (400 MHz, CDCl₃): δ=2.69 (t, 2H), 1.44 (m, 15H), 1.25 (s, 2H), 1.1 (q, 2H), 0.6 (q, 2H).

Example 17A

[3-(1,3-Dioxo-1,3-dihydro-2H-isoindol-2-yl)propyl](triphenyl)phosphonium Bromide

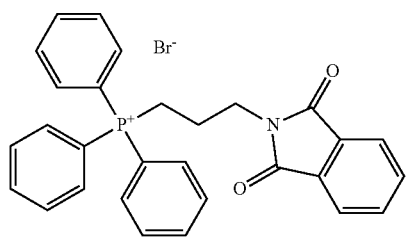 [SMILES: O=C1c2ccccc2C(=O)N1CCC[P+](c1ccccc1)(c1ccccc1)c1ccccc1 ; [Br-]]

2.50 g (9.33 mmol) of 2-(3-bromopropyl)-1H-isoindole-1,3(2H)-dione in 25 ml of xylene were degassed with argon, and 2.45 g (9.33 mmol) of triphenylphosphine were added. The mixture was stirred under reflux for 24 h and then filtered at 70° C. The filter cake was washed with a little di-ethyl ether and dried under high vacuum. This gave 3.50 g (70.8% of theory) of the title compound.

¹H-NMR (400 MHz, DMSO-d₆): δ=7.86 (m, 7H), 7.76 (m, 12H), 3.76 (t, 2H), 3.7 (m, 2H), 1.94 (m, 2H).

Example 18A

Ethyl 1-formylcyclopropanecarboxylate

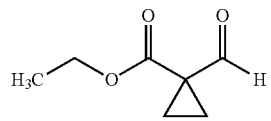

At 0° C., 5.05 g (11.9 mmol) of Dess-Martin periodane reagent were added to a solution of 1.225 g (8.5 mmol) of ethyl 1-hydroxymethylcyclopropanecarboxylate [for the preparation see, for example, T. A. Ayers, *Tetrahedron Lett.* 40 (30), 5467-5470 (1999)] in 43 ml of dichloromethane, and the mixture was then stirred at RT for 6 h. A solution of 6.7 g (42.5 mmol) of sodium thiosulfate in 60 ml of saturated aqueous sodium bicarbonate solution was then added to the reaction mixture. The mixture was stirred at RT for 20 min, and the phases were then separated. The organic phase was washed twice with water, dried over magnesium sulfate and concentrated at 20° C. under reduced pressure. This gave 1.139 g (80.0% of theory) of the target compound.

¹H-NMR (400 MHz, DMSO-d₆): δ=10.17 (s, 1H), 4.20 (q, 2H), 1.58 (q, 2H), 1.47 (q, 2H), 1.24 (t, 3H).

Example 19A

Ethyl 1-[(1E/Z)-4-(1,3-dioxo-1,3-dihydro-2H-isoindol-2-yl)but-1-en-1-yl]cyclopropanecarboxylate

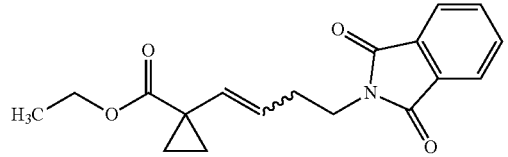 [SMILES: CCOC(=O)C1(C=CCCN2C(=O)c3ccccc3C2=O)CC1]

Under argon, 600 mg (3.377 mmol) of ethyl 1-formylcyclopropanecarboxylate and 1.79 g (3.377 mmol) of [3-(1,3-dioxo-1,3-dihydro-2H-isoindol-2-yl)propyl](triphenyl)phosphonium bromide were initially charged in 12 ml of dry DMSO, and at 6° C. a solution of 379 mg (3.377 mmol) of potassium tert-butoxide in 3 ml of DMSO was added. The mixture was stirred at 6° C. for 25 min and then warmed to RT and stirred for a further 4 h. 25 ml of water and 35 ml of ethyl acetate were then added, and the reaction mixture was extracted. The organic phase was washed twice with water and saturated sodium chloride solution, dried over magnesium sulfate and concentrated under reduced pressure. The product was purified by chromatography on silica gel (mobile phase cyclohexane/ethyl acetate 5:1). This gave 504 mg (47.6% of theory) of the title compound as an E/Z isomer mixture (about 1:2.5).

LC-MS (Method 3): $R_t$=1.24 min; m/z=314 (M+H)$^+$.

Example 20A

Ethyl 1-[(1E/Z)-4-aminobut-1-en-1-yl]cyclopropan-ecarboxylate

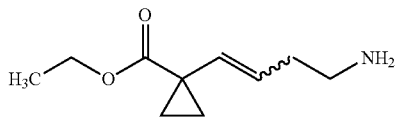

48 µl (0.99 mmol) of hydrazine hydrate were added to a solution of 255 mg (0.18 mmol) of ethyl 1-[(1E/Z)-4-(1,3-dioxo-1,3-dihydro-2H-isoindol-2-yl)but-1-en-1-yl]cyclo-propanecarboxylate in 5.1 ml of ethanol, and the mixture was stirred under reflux for 1 h. The resulting precipitate was filtered off with suction and washed with ethanol, and the filtrate was concentrated at 20° C. under reduced pressure. This gave 220 mg of the crude title compound (E/Z isomer mixture) which was used without further purification for subsequent reactions.

MS (DCI): m/z=184 (M+H)$^+$.

Example 21A

Methyl[1-(prop-2-en-1-yl)cyclopropyl]acetate

45.69 g (222.2 mmol) of copper(I) bromide/dimethyl sulfide complex and 9.42 g (222.2 mmol) of anhydrous lithium chloride were dissolved in 300 ml of THF, the mixture was cooled to −78° C. and 100 ml (200 mmol) of a 2 M solution of allylmagnesium bromide in diethyl ether were added slowly. 28.2 ml (222.2 mmol) of chlorotrimethylsilane and 11.21 g (100 mmol) of methyl cyclopropylideneacetate [CAS Registry No. 110793-87-8] were then added dropwise in succession to the reaction solution, and the mixture was stirred for about 5 min (monitored by TLC, mobile phase cyclohexane/ethyl acetate 20:1). 50 ml of an aqueous solution of ammonia/ammonium chloride (1:9) were then added, and the reaction solution was filtered through kieselguhr. The organic phase was separated off and the aqueous phase was extracted two more times with diethyl ether. The combined organic phases were then washed with saturated sodium chloride solution, dried over magnesium sulfate and concentrated under reduced pressure. The residue was dissolved in 100 ml of THF, and 222 ml (222 mmol) of a 1 M solution of tetrabutylammonium fluoride in THF were added. The reaction solution was stirred for another 10 min and then concentrated to dryness. The crude product obtained was purified chromatographically on silica gel (mobile phase cyclohexane/ethyl acetate 20:1). This gave 6.92 g (45 mmol, 45% of theory) of the title compound.

GC-MS (Method 1): $R_t$=2.48 min; m/z=155 (M+H)$^+$.

$^1$H-NMR (400 MHz, DMSO-d$_6$, δ/ppm): 5.84-5.69 (1H, m), 5.02 (2H, d), 3.58 (3H, s), 2.24 (2H, s), 2.05 (2H, d), 0.45-0.35 (4H, m).

Example 22A

Methyl[1-(3-bromopropyl)cyclopropyl]acetate

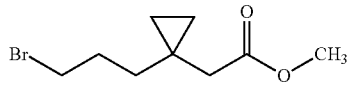

Under argon and at 0° C., 3.4 ml (3.4 mmol) of borane/THF complex solution (1 M in THF) were added dropwise to 1542 mg (10 mmol) of methyl [1-(prop-2-en-1-yl)cyclopropyl]acetate in 10 ml of anhydrous THF. After 30 min at 0° C., the reaction was stirred at RT for a further 30 min, and 22 µl (0.54 mmol) of methanol were then added. At −5° C., 0.62 ml (12 mmol) of bromine and 2971 mg (16.5 mmol) of sodium methoxide solution (30% in methanol) were then successively added dropwise to the reaction mixture. Once the reaction had reached room temperature, 10 ml of saturated sodium bicarbonate solution were added, the organic phase was separated off and the aqueous phase was extracted three more times with tert-butyl methyl ether. The combined organic phases were washed with saturated sodium chloride solution and dried over anhydrous magnesium sulfate. Removal of the solvent under reduced pressure gave 683 mg (2.9 mmol, 29% of theory) of the title compound as a yellow oil.

GC-MS (Method 1): $R_t$=4.29 min; m/z=205 (M-OCH$_3$+H)$^+$, 155 (M-Br)$^+$.

$^1$H-NMR (400 MHz, DMSO-d$_6$, δ/ppm): 3.68 (3H, s), 3.41 (2H, t), 2.24 (2H, s), 2.01-1.91 (2H, m), 1.51-1.44 (2H, m), 0.50-0.38 (4H, m).

Example 23A

Methyl[1-(3-azidopropyl)cyclopropyl]acetate

680 mg (2.89 mmol) of methyl[1-(3-bromopropyl)cyclopropyl]acetate and 1128 mg (17.35 mmol) of sodium azide in 5 ml of DMF were stirred at 60° C. for 2 h. The reaction mixture was then concentrated under reduced pressure. The residue was taken up in ethyl acetate and the solution was washed with saturated sodium chloride solution and dried over anhydrous magnesium sulfate. Removal of the solvent under reduced pressure gave 389 mg (1.97 mmol, 68% of theory) of the title compound as a yellow oil.

MS (DCI): m/z=198 (M+H)$^+$, 215 (M+NH$_4$)$^+$.

$^1$H-NMR (400 MHz, DMSO-d$_6$, δ/ppm): 3.59 (3H, s), 3.30 (2H, t), 2.26 (2H, s), 1.64-1.53 (2H, m), 1.36-1.29 (2H, m), 0.43-0.30 (4H, m).

Example 24A

Methyl[1-(3-aminopropyl)cyclopropyl]acetate hydrochloride

At room temperature, a mixture of 389 mg (1.97 mmol) of methyl[1-(3-azidopropyl)cyclopropyl]acetate, 40 mg of 10% palladium on carbon and 1.97 ml (1.97 mmol) of 1 M hydrochloric acid in 10 ml of ethanol were hydrogenated under atmospheric pressure overnight. After the reaction had ended, the mixture was filtered and the filtrate was concentrated to dryness. This gave 313 mg (1.51 mmol, 76% of theory) of the title compound as a colorless oil.

MS (DCI): m/z=172 (M+H)$^+$.

$^1$H-NMR (400 MHz, DMSO-d$_6$, δ/ppm): 3.60 (3H, s), 2.79-2.66 (2H, m), 2.26 (2H, s), 1.68-1.55 (2H, m), 1.39-1.27 (2H, m), 0.45-0.28 (4H, m).

Example 25A

Tert-Butyl 1-(prop-2-en-1-yl)cyclopropanecarboxylate

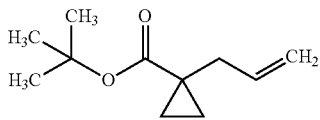

9.9 ml (70.32 mmol) of diisopropylamine were initially charged in 35 ml of THF, 28.1 ml (70.32 mmol) of a 2.5 M solution of n-butyllithium in n-hexane were added at −40° C. and the mixture was stirred for 30 min. The reaction mixture was then cooled to −78° C., and a solution of 10 g (70.32 mmol) of tert-butyl cyclopropanecarboxylate in 5 ml of THF was added dropwise. The mixture was stirred at −78° C. for 4 h, and a solution of 5.8 ml (66.81 mmol) of allyl bromide in 5 ml of THF was then added dropwise. The reaction mixture was slowly warmed to RT overnight, and aqueous ammonium chloride solution was then added carefully. The mixture was extracted three times with methyl tert-butyl ether. The combined organic phases were dried over sodium sulfate and concentrated under reduced pressure. This gave 10.7 g (83.5% of theory) of the target compound.

GC-MS (Method 1): R$_t$=2.5 min; m/z=126 (M-C$_4$H$_8$)$^+$.

$^1$H-NMR (400 MHz, DMSO-d$_6$): δ=5.82 (m, 1H), 4.98 (d, 2H), 2.21 (d, 2H), 1.37 (s, 9H), 0.99 (q, 2H), 0.69 (q, 2H).

Example 26A

Tert-Butyl 1-(2-oxoethyl)cyclopropanecarboxylate

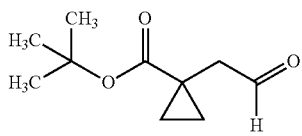

4.0 g (21.9 mmol) of tert-butyl 1-(prop-2-en-1-yl)cyclopropanecarboxylate were dissolved in 70 ml of methanol and 30 ml of dichloromethane. At −78° C., ozone in a stream of O$_2$ was passed through the reaction solution for 45 min using an ozone generator. Once the color of the solution had changed to light blue, the reaction solution was flushed with pure oxygen until the color had disappeared again. 6.5 ml (88.9 mmol) of dimethyl sulfide were then added, and the reaction solution was slowly warmed to RT. The mixture was concentrated on a rotary evaporator and the residue was purified by chromatography on silica gel (mobile phase gradient cyclohexane/ethyl acetate 50:1, 30:1, 20:1, 10:1). This gave 1.87 g (44.1% of theory) of the target compound.

GC-MS (Method 1): R$_t$=3.3 min; m/z=184 (M)$^+$.

Example 27A

Tert-Butyl Cis/trans-1-[4-methoxy-4-oxobut-2-en-1-yl]cyclopropanecarboxylate

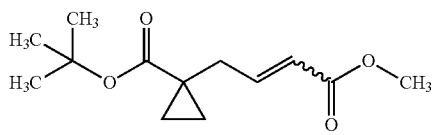 [SMILES: COC(=O)C=CCC1(C(=O)OC(C)(C)C)CC1]

0.425 g (10.63 mmol) of sodium hydride were initially charged in 40 ml of THF, and 1.6 ml (11.11 mmol) of trimethyl phosphonoacetate were added at 0° C. The mixture was stirred at 0° C. for 1 h, 1.78 g (9.66 mmol) of tert-butyl 1-(2-oxoethyl)cyclopropanecarboxylate were then added and the reaction mixture was slowly warmed to RT. The mixture was stirred at RT for another 2 h, water was then added and the mixture was extracted three times with dichloromethane. The combined organic phases were washed with saturated sodium chloride solution, dried over magnesium sulfate and concentrated under reduced pressure. The residue was purified by chromatography on silica gel (mobile phase gradient dichloromethane/ethyl acetate 100:0→100:0.1). This gave 1.32 g (56.7% of theory) of the title compound (significant excess of trans isomer).

GC-MS (Method 1): R$_t$=4.57 min, m/z=184 (M-C$_4$H$_8$)$^+$ cis isomer; R$_t$=4.82 min, m/z=184 (M-C$_4$H$_8$)$^+$ trans isomer.

$^1$H-NMR (400 MHz, DMSO-d$_6$): δ=6.91 (dt, 1H), 6.88 (d, 1H), 3.65 (s, 3H), 2.37 (d, 2H), 1.36 (s, 9H), 1.05 (q, 2H), 0.77 (q, 2H).

Example 28A

Tert-Butyl Cis/trans-1-[4-hydroxybut-2-en-1-yl]cyclopropanecarboxylate

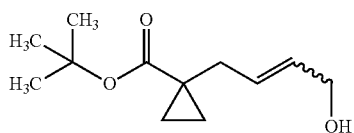

At −90° C., 9.7 ml (9.86 mmol) of diisobutylaluminum hydride, as a 1 M solution in hexane, were slowly added dropwise to a solution of 1.185 g (4.93 mmol) of tert-butyl cis/trans-1-[4-methoxy-4-oxobut-2-en-1-yl]cyclopropanecarboxylate in 15 ml of dichloromethane. The mixture was stirred at −90° C. for 2 h, and about 10 ml of 20% strength aqueous potassium tartrate solution were then added dropwise to the cold mixture. The mixture was then diluted with water and dichloromethane and, after phase separation, the organic phase was extracted repeatedly with water and dried over sodium sulfate. The organic phase was concentrated under reduced pressure and the residue was purified by chromatography on silica gel (mobile phase gradient cyclohexane/ethyl acetate 10:1, 8:1, 4:1, 2:1). This gave 0.279 g (26.7% of theory) of the target compound (significant excess of trans isomer).

$^1$H-NMR (400 MHz, DMSO-$d_6$): δ=5.55 (m, 2H), 3.88 (t, 2H), 2.18 (d, 2H), 1.37 (s, 9H), 0.97 (q, 2H), 0.68 (q, 2H).

Example 29A

Tert-Butyl Cis/trans-1-[4-(1,3-dioxo-1,3-dihydro-2H-isoindol-2-yl)but-2-en-1-yl]cyclopropane-carboxylate

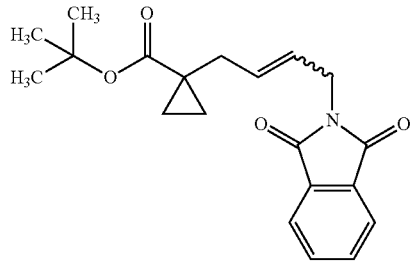 [SMILES: CC(C)(C)OC(=O)C1(CC=CCN2C(=O)c3ccccc3C2=O)CC1]

302.6 mg (1.43 mmol) of tert-butyl cis/trans-1-[4-hydroxybut-2-en-1-yl]cyclopropanecarboxylate were dissolved in 2 ml of THF, and 251.7 mg (1.71 mmol) of phthalimide and 411.3 mg (1.57 mmol) of triphenylphosphine were added. The reaction mixture was cooled to −10° C., and 713.7 mg (1.639 mmol) of a 40% strength solution of diethyl azodicarboxylate in toluene were slowly added dropwise. The mixture was then warmed to RT and stirred for another 1.5 h. The reaction mixture was then added to water and extracted with dichloromethane. The organic phase was dried over sodium sulfate and concentrated under reduced pressure. The residue was purified by chromatography on silica gel (mobile phase gradient cyclohexane/ethyl acetate 6:1, 4:1, 2:1). This gave 121 mg (24.8% of theory) of the target compound (significant excess of trans isomer).

LC-MS (Method 2): $R_t$=2.35 min; m/z=364 (M+Na)$^+$.

$^1$H-NMR (400 MHz, DMSO-$d_6$): δ=7.89 (m, 4H), 5.61 (m, 1H), 5.51 (m, 1H), 4.14 (d, 2H), 2.14 (d, 2H), 1.24 (s, 9H), 0.94 (q, 2H), 0.66 (q, 2H).

Example 30A

Tert-Butyl Cis/trans-1-[4-aminobut-2-en-1-yl]cyclopropanecarboxylate

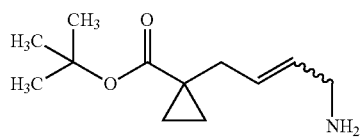

At RT, 34 μl (0.703 mmol) of hydrazine hydrate were added to a solution of 120 mg (0.351 mmol) of tert-butyl cis/trans-1-[4-(1,3-dioxo-1,3-dihydro-2H-isoindol-2-yl)but-2-en-1-yl]cyclo-propanecarboxylate in 2.4 ml of ethanol. The mixture was stirred under reflux for 20 min. The reaction mixture was then filtered and the filtrate was concentrated at 20° C. on a rotary evaporator. The residue was taken up in dichloromethane and washed twice with saturated aqueous sodium bicarbonate solution. The organic phase was dried over magnesium sulfate and, at 20° C., concentrated under reduced pressure. This gave 81.2 mg of slightly impure crude product (about 109% of theory; significant excess of trans isomer). The substance was stored in a freezer until use in subsequent reactions.

MS (DCI): m/z=212 (M+H)$^+$.

$^1$H-NMR (400 MHz, CDCl$_3$): δ=8.06 (q, 1H), 7.82 (q, 1H), 5.51 (m, 2H), 3.11 (d, 2H), 2.17 (m, 2H), 1.37 (s, 9H), 0.97 (q, 2H), 0.67 (q, 2H).

Example 31A

Tert-Butyl 5,5,5-trifluoro-2-(4-methylphenyl)pentanoate

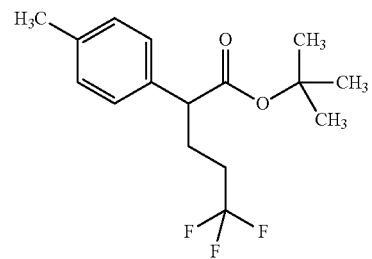 [SMILES: Cc1ccc(C(CCC(F)(F)F)C(=O)OC(C)(C)C)cc1]

With exclusion of oxygen, 0.88 ml (6.3 mmol) of diisopropylamine were initially charged in 20 ml of THF, the mixture was cooled to −78° C. and 2.52 ml (6.3 mmol) of a 2.5 M solution of n-butyl-lithium in hexane were added slowly. The reaction solution was then warmed to −10° C. and stirred at this temperature for 10 min. The reaction solution was then once more cooled to −78° C., and 1 g (4.85 mmol) of tert-butyl (4-methylphenyl)acetate, dissolved in 10 ml of THF, was added slowly. The reaction solution was then slowly warmed to −30° C. and then once more cooled to −78° C. Once this temperature had been reached, 0.62 ml (5.82 mmol) of 3-bromo-1,1,1-trifluoropropane was slowly added dropwise. After the addition had ended, the solution was slowly warmed to room temperature and stirred overnight. The reaction was checked by TLC (mobile phase cyclohexane/ethyl acetate 10:1), after which saturated ammonium chloride solution was added and the mixture was taken up in ethyl acetate. The aqueous phase was extracted twice with ethyl acetate. The combined organic phases were dried over sodium sulfate. After filtration, the solvent was removed under reduced pressure. The crude product was purified chromatographically on silica gel (mobile phase cyclohexane/ethyl acetate 10:1). This gave 542 mg (1.79 mmol, 37% of theory) of a yellowish oil.

GC-MS (Method 1): $R_t$=4.41 min; m/z=246 (M-C$_4$H$_9$+H)$^+$.

Example 32A

Tert-Butyl 3-methyl-2-(4-methylphenyl)pentanoate

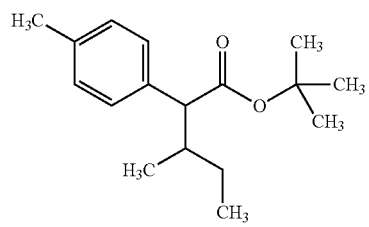 [SMILES: CCC(C)C(C(=O)OC(C)(C)C)c1ccc(C)cc1]

Under argon, 19.58 g (174.5 mmol) of potassium tert-butoxide were initially charged in 200 ml of DMF, the mixture was cooled to 0° C., 30 g (145.4 mmol) of tert-butyl (4-methylphenyl)acetate, dissolved in 50 ml of DMF, were added slowly and the mixture was then stirred at 0° C. for 30 min. 18.95 ml (174.5 mmol) of 2-bromobutane were then slowly added drowise, and the solution was stirred at 0° C. for 4 h. 200 ml of water and 200 ml of diethyl ether were then added to the reaction solution. The aqueous phase was extracted twice with diethyl ether. The combined organic phases were dried over magnesium sulfate. After filtration, the solvent was removed under reduced pressure. The crude product was purified chromatographically on silica gel (mobile phase cyclohexane/ethyl acetate 20:1). This gave 15.5 g (59.1 mmol, 40.6% of theory) of a colorless liquid.

$^1$H-NMR (400 MHz, DMSO-$d_6$, δ/ppm): 7.17 (2H, d), 7.11 (2H, d), 3.11 (1H, d), 2.27 (3H, s), 2.04-1.90 (1H, m), 1.55-1.42 (1H, m), 1.35 (9H, s), 1.24-1.10 (1H, m), 0.99-0.86 (3H, m), 0.77-0.51 (3H, m).

GC-MS (Method 1): $R_t$=5.04 min; m/z=206 (M-$C_4H_9$+H)$^+$.

The compound listed in the table below was obtained in an analogous manner:

4-bromotoluene, dissolved in 50 ml of toluene, were then added dropwise, and the reaction solution was warmed first to room temperature and then to 80° C. The mixture was stirred at this temperature for 2 h and then cooled to room temperature and stirred overnight. After the reaction had ended (monitored by TLC, mobile phase cyclohexane/dichloromethane 2:1), the reaction mixture was filtered through kieselguhr, the residue was washed repeatedly with ethyl acetate and dichloromethane and the combined filtrates were concentrated under reduced pressure. The crude product obtained was purified chromatographically on silica gel (mobile phase petroleum ether/dichloromethane 4:1→3:1). This gave 3.91 g (14.3 mmol, 48.8% of theory) of the title compound as colorless liquid.

$^1$H-NMR (400 MHz, DMSO-$d_6$, δ/ppm): 7.26 (2H, d), 7.20-7.12 (2H, m), 4.17-3.95 (2H, m), 3.74 (0.25H, d), 3.66 (0.75H, d), 3.35-3.07 (1H, m), 2.29 (2.25H, s), 2.28 (0.75H, s), 1.17 (0.75H, d), 1.11 (3H, t), 0.76 (2.25H, d) (diastereomer mixture).

GC-MS (Method 1): $R_t$=4.20 min, m/z=275 (M+H)$^+$ (diastereomer 1); $R_t$=4.23 min, m/z=275 (M+H)$^+$ (diastereomer 2).

| Example | Name/Structure | Analytical data |
|---|---|---|
| 33A | tert-butyl cyclopentyl(4-methylphenyl)acetate 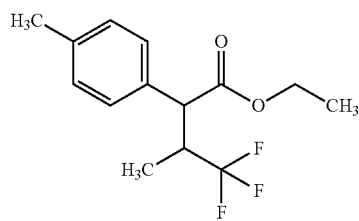 [SMILES: CCOC(=O)C(c1ccc(C)cc1)C(C)C(F)(F)F] | $^1$H-NMR (400 MHz, DMSO-$d_6$, δ/ppm): 7.19 (2H, d), 7.11 (2H, d), 3.12 (1H, d), 2.45-2.29 (1H, m), 2.27 (3H, s), 1.89-1.71 (1H, m), 1.67-1.45 (3H, m), 1.44-1.15 (3H, m), 1.36 (9H, s), 1.02-0.84 (1H, m). MS (DCI): m/z = 292 (M + NH$_4$)$^+$; GC-MS (Method 1): $R_t$ = 5.89 min; m/z = 218 (M − $C_4H_9$ + H)$^+$. |

Example 34A

Ethyl 4,4,4-trifluoro-3-methyl-2-(4-methylphenyl)butanoate

Under argon, 196.9 mg (0.88 mmol) of palladium(II) acetate and 724.8 mg (1.84 mmol) of 2-di-cyclohexylphosphino-2'-(N,N-dimethylamino)biphenyl were initially charged in 50 ml of anhydrous toluene. 43.8 ml (43.8 mmol) of a 1 M solution of lithium hexamethyldisilazide in THF were then added slowly, and the reaction solution was stirred at room temperature for 10 min. The reaction solution was then cooled to −10° C., 7 g (38.0 mmol) of ethyl 4,4,4-trifluoro-3-methyl-butanoate were added slowly and the mixture was stirred at −10° C. for 10 min. 5 g (29.2 mmol) of

Example 35A

Tert-Butyl 2-[4-(bromomethyl)phenyl]-5,5,5-trifluoropentanoate

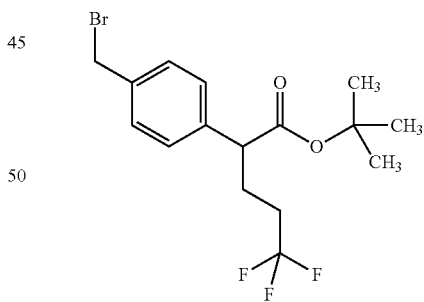

540 mg (1.79 mmol) of tert-butyl 5,5,5-trifluoro-2-(4-methylphenyl)pentanoate, 333.8 mg (1.78 mmol) of N-bromosuccinimide and 14.7 mg (0.09 mmol) of 2,2'-azobis-2-methylpropionitrile in 10 ml of carbon tetrachloride were stirred under reflux for 2 h. After the reaction had gone to completion, the succinimide was filtered off and the filter residue was washed with dichloromethane. The filtrate was concentrated under reduced pressure. The crude product was purified chromatographically on silica gel (mobile phase cyclohexane/ethyl acetate 10:1). This gave 659 mg (1.72 mmol, 97% of theory) of a yellowish oil.

GC-MS (Method 1): $R_t$=5.91 min; m/z=301 (M-Br)$^+$.

Example 36A

Tert-Butyl 2-[4-(bromomethyl)phenyl]-3-methylpentanoate

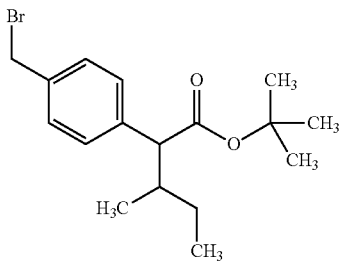 [SMILES: CCC(C)C(C(=O)OC(C)(C)C)c1ccc(CBr)cc1]

15 g (59.1 mmol) of tert-butyl 3-methyl-2-(4-methylphenyl)pentanoate, 11 g (62 mmol) of N-bromosuccinimide and 97 mg (0.59 mmol) of 2,2'-azobis-2-methylpropionitrile in 150 ml of dichloromethane were stirred under reflux for 2 h. After the reaction had gone to completion, the solvent was removed under reduced pressure. The crude product was purified chromatographically on silica gel (mobile phase cyclohexane/ethyl acetate 20:1). This gave 16.22 g (47.5 mmol, 80% of theory) of a colorless oil.

GC-MS (Method 1): $R_t$=6.41 min; m/z=261 (M-Br)$^+$.
MS (DCI): m/z=358/360 (M+NH$_4$)$^+$.

The compound listed in the table below was obtained in an analogous manner:

| Example | Name/Structure | Analytical data |
|---|---|---|
| 37A | tert-butyl [4-(bromomethyl)phenyl](cyclopentyl)-acetate 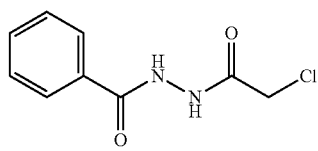 | $^1$H-NMR (400 MHz, DMSO-d$_6$, δ/ppm): 7.39 (2H, d), 7.30 (2H, d), 4.68 (2H, s), 3.21 (1H, d), 2.45-2.31 (1H, m), 1.89-1.74 (1H, m), 1.69-1.45 (3H, m), 1.44-1.16 (3H, m), 1.35 (9H, s), 1.02-0.88 (1H, m). MS (DCI): m/z = 370/372 (M + NH$_4$)$^+$. |

Example 38A

Ethyl 2-[4-(bromomethyl)phenyl]-4,4,4-trifluoro-3-methylbutanoate

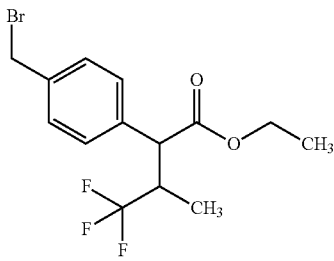 [SMILES: CCOC(=O)C(c1ccc(CBr)cc1)C(C)C(F)(F)F]

2.25 g (8.2 mmol) of ethyl 4,4,4-trifluoro-3-methyl-2-(4-methylphenyl)butanoate, 1.53 g (8.6 mmol) of N-bromosuccinimide and 67 mg (0.41 mmol) of 2,2'-azobis-(2-methylpropionitrile) in 36 ml of trichloromethane were stirred under reflux overnight. After the reaction had gone to completion, the succinimide was filtered off and the filter residue was washed with dichloromethane. The filtrate was concentrated under reduced pressure. The crude product was purified chromatographically on silica gel (mobile phase cyclohexane/ethyl acetate 40:1). This gave 2.667 g (7.5 mmol, 92% of theory) of a yellowish oil.

GC-MS (Method 1): $R_t$=5.72 min, m/z=373 (M-Br)$^+$ (diastereomer 1); $R_t$=5.74 min, m/z=373 (M-Br)$^+$ (diastereomer 2).

Example 39A

N'-(2-Chloroacetyl)benzenecarbohydrazide

A suspension of 500 g (3.67 mol) of benzenecarbohydrazide in 3.75 liters of THF was heated to reflux, whereupon the benzenecarbohydrazide dissolved. 497.7 g (4.41 mol) of chloroacetyl chloride, dissolved in 125 ml of THF, were added dropwise to this solution, and the solution was stirred under reflux for another 30 min. After the reaction had gone to completion, (monitored by TLC, mobile phase dichloromethane/methanol 9:1), 22.5 liters of water and 10 liters of ethyl acetate were added and the mixture was adjusted to pH 7 with solid sodium bicarbonate. The aqueous phase was extracted once with 2.5 liters of ethyl acetate. The combined organic phases were dried and the solution was then concentrated to dryness under reduced pressure. The white solid obtained was dissolved in a 1:1 mixture of dichloromethane and methanol and applied to 3 kg of silica gel. Using two portions of silica gel (8 kg each), the product was chromatographed using initially 50 liters of dichloromethane/ethyl acetate 7:3 and then 125 liters of dichloromethane/ethyl acetate 1:1 as mobile phase. Concentration of the product fractions gave 424 g (1.99 mol, 54% of theory) of the title compound as a white solid.

$^1$H-NMR (400 MHz, DMSO-d$_6$, δ/ppm): 10.56-10.32 (2H, broad), 7.88 (2H, d), 7.58 (1H, t), 7.50 (2H, t), 4.21 (2H, s).

MS (DCI): m/z=213 (M+H)+, 230 (M+NH4)+.

Example 40A

2-Phenyl-4H-1,3,4-oxadiazin-5(6H)-one

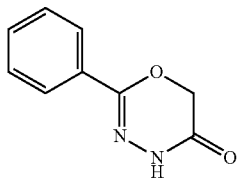 [SMILES: O=C1COC(c2ccccc2)=NN1]

812 g (3.82 mol) of N'-(2-chloroacetyl)benzenecarbohydrazide were dissolved in 13 liters of dry DMF, and 384.95 g (4.58 mol) of sodium bicarbonate were added. The reaction solution was then heated to 100° C. and stirred at this temperature overnight. After the reaction had gone to completion (monitored by TLC, mobile phase dichloromethane/ethyl acetate 9:1), the reaction solution was cooled to room temperature, poured into 65 liters of water and extracted three times with in each case 17.5 liters of ethyl acetate. The combined organic phases were washed with 13.8 liters of saturated aqueous sodium bicarbonate solution, dried and concentrated to dryness under reduced pressure. The solid obtained was dissolved in a 9:1 mixture of dichloromethane and methanol and applied to 17 kg of silica gel. Using two portions of silica gel (8 kg each), the product was chromatographed using 260 liters of dichloromethane/ethyl acetate 9:1 as mobile phase. The combined product fractions were concentrated, and the resulting solid was triturated with 3 liters of diethyl ether. Filtration gave 247 g (1.40 mol, 35% of theory) of the title compound as a white solid.

$^1$H-NMR (400 MHz, DMSO-$d_6$, δ/ppm): 11.04 (1H, s), 7.78 (2H, d), 7.53-7.41 (3H, m), 4.79 (2H, s).
MS (DCI): m/z=177 (M+H)+.

Example 41A

6-Phenylpyridazin-3 (2H)-one

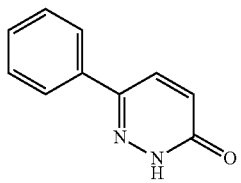 [SMILES: O=c1ccc(-c2ccccc2)n[nH]1]

19.6 g (162.95 mmol) of 1-phenylethanone and 5 g (54.32 mmol) of oxoacetic acid monohydrate were stirred at 100° C. for 2 hours. The reaction solution was then cooled to 40° C., and 20 ml of water and 4 ml of ammonia were added. The mixture was then extracted twice with 50 ml of dichloromethane. 2.64 ml (53.32 mmol) of hydrazine monohydrate were then added to the aqueous phase, and the mixture was stirred at 100° C. for 2 hours. After the reaction, the reaction solution was cooled to room temperature. The precipitated crystals were filtered off with suction, washed with water and dried in a vacuum drying cabinet at 50° C. overnight. This gave 4.3 g (24.97 mmol, 15% of theory) of the title compound as colorless crystals.

LC-MS (Method 4): $R_t$=1.39 min; m/z=173 (M+H)+.
$^1$H-NMR (400 MHz, DMSO-$d_6$, δ/ppm): 13.2 (s, 1H), 8.04 (d, 1H), 7.86 (d, 2H), 7.53-7.41 (m, 3H), 7.00 (d, 1H).

Example 42A

Tert-Butyl Cyclopentyl{4-[(5-oxo-2-phenyl-5,6-dihydro-4H-1,3,4-oxadiazin-4-yl)methyl]phenyl}-acetate

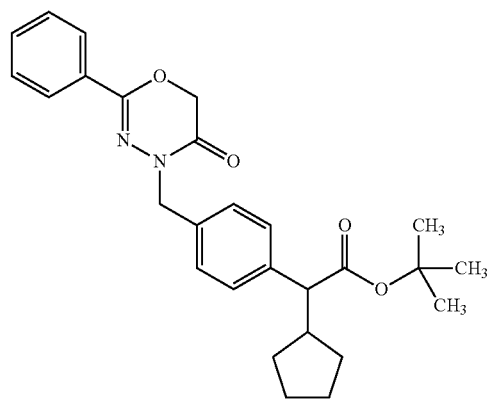 [SMILES: CC(C)(C)OC(=O)C(c1ccc(CN2N=C(c3ccccc3)OCC2=O)cc1)C1CCCC1]

Preparation Method 1:

9.9 g (28.0 mmol) of tert-butyl [4-(bromomethyl)phenyl](cyclopentyl)acetate, 5.92 g (33.6 mmol) of 2-phenyl-4H-1,3,4-oxadiazin-5(6H)-one and 13.70 g (42.03 mmol) of cesium carbonate in 100 ml of DMF were stirred at 60° C. for 12 h. After cooling, the mixture was added to ice-water and extracted with diethyl ether. The organic phase was dried over magnesium sulfate and concentrated to dryness under reduced pressure. The crude product was purified chromatographically on silica gel (mobile phase cyclohexane/ethyl acetate 20:1). This gave 6.6 g (14.7 mmol, 52% of theory) of the title compound.

Preparation Method 2:

8.16 g (23.1 mmol) of tert-butyl [4-(bromomethyl)phenyl](cyclopentyl)acetate, 3.7 g (21 mmol) of 2-phenyl-4H-1,3,4-oxadiazin-5(6H)-one and 7.53 g (23.1 mmol) of cesium carbonate in 147 ml of DMF were stirred at room temperature for 12 h. The reaction solution was then stirred with saturated aqueous sodium bicarbonate solution and extracted twice with ethyl acetate. The combined organic phases were dried over magnesium sulfate and evaporated to dryness under reduced pressure. The crude product obtained was purified chromatographically on silica gel (mobile phase cyclohexane/ethyl acetate 5:1). This gave 6.51 g (14.5 mmol, 69% of theory) of the title compound.

$^1$H-NMR (400 MHz, DMSO-$d_6$, δ/ppm): 7.76 (2H, d), 7.55-7.42 (3H, m), 7.31 (4H, s), 4.94 (2H, s), 4.87 (2H, s), 3.19 (1H, d), 2.45-2.31 (1H, m), 1.88-1.74 (1H, m), 1.69-1.46 (3H, m), 1.45-1.15 (3H, m), 1.34 (9H, s), 1.03-0.89 (1H, m).

LC-MS (Method 4): $R_t$=3.27 min; m/z=449 (M+H)+.

The compounds listed in the table below were obtained in an analogous manner:

| Example | Name/Structure | Analytical data |
| --- | --- | --- |
| 43A | tert-butyl 5,5,5-trifluoro-2-{4-[(5-oxo-2-phenyl-5,6-dihydro-4H-1,3,4-oxadiazin-4-yl)methyl]phenyl}-pentanoate | LC-MS (Method 2): $R_t$ = 2.69 min; m/z = 477 $(M + H)^+$. |
| 44A | tert-butyl 3-methyl-2-{4-[(5-oxo-2-phenyl-5,6-dihydro-4H-1,3,4-oxadiazin-4-yl)methyl]phenyl}-pentanoate | LC-MS (Method 4): $R_t$ = 3.24 min; m/z = 437 $(M + H)^+$. |
| 45A | tert-butyl cyclopentyl{4-[(6-oxo-3-phenylpyridazin-1(6H)-yl)methyl]phenyl}acetate | LC-MS (Method 3): $R_t$ = 1.68 min; m/z = 467 $(M + Na)^+$.<br>$^1$H-NMR (400 MHz, DMSO-$d_6$, δ/ppm): 8.08 (1H, d), 7.91-7.85 (2H, m), 7.53-7.42 (3H, m), 7.30 (4H, s), 7.09 (1H, d), 5.21 (2H, s), 3.18 (1H, d), 2.44-2.30 (1H, m), 1.85-1.74 (1H, m), 1.65-1.45 (3H, m), 1.44-1.35 (1H, m), 1.34 (9H, s), 1.30-1.15 (2H, m), 1.00-0.88 (1H, m). |

| Example | Name/Structure | Analytical data |
|---|---|---|
| 46A | ethyl 4,4,4-trifluoro-3-methyl-2-{4-[(5-oxo-2-phenyl-5,6-dihydro-4H-1,3,4-oxadiazin-4-yl)-methyl]phenyl}butanoate 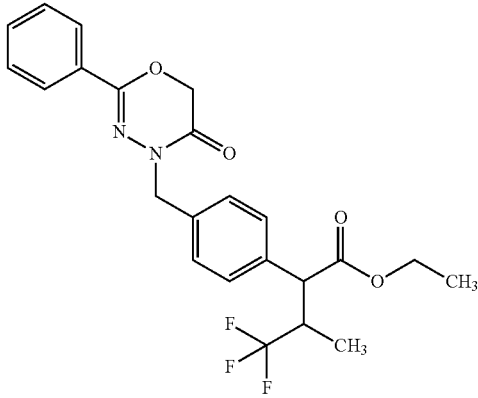 [SMILES: CCOC(=O)C(c1ccc(CN2N=C(c3ccccc3)OCC2=O)cc1)C(C)C(F)(F)F] | GC-MS (Method 1): R$_t$ = 9.98 min; m/z = 449 (M + H)$^+$. |

Example 47A and Example 48A

Tert-Butyl Cyclopentyl{4-[(6-oxo-3-phenylpyridazin-1(6H)-yl)methyl]phenyl}acetate (Enantiomers 1 and 2)

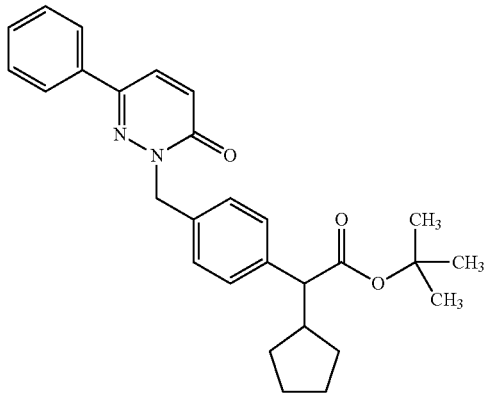 [SMILES: CC(C)(C)OC(=O)C(c1ccc(Cn2nc(-c3ccccc3)ccc2=O)cc1)C1CCCC1]

7.42 g (16.69 mmol) of the racemic tert-butyl cyclopentyl{4-[(6-oxo-3-phenylpyridazin-1(6H)-yl)-methyl]phenyl}acetate (Example 45A) were separated by preparative HPLC on a chiral phase into the enantiomers [column: Daicel Chiralpak AS-H, 5 μm, 250 mm×20 mm; mobile phase: isohexane/isopropanol 75:25 (v/v); flow rate: 15 ml/min; UV detection: 220 nm; temperature: 30° C.]:

Example 47A

Enantiomer 1

Yield: 4.1 g

R$_t$ 5.28 min; purity >99%; >99% ee

[column: Daicel Chiralpak AS-H, 5 μm, 250 mm×4.6 mm; mobile phase: isohexane/isopropanol 75:25 (v/v); flow rate: 1 ml/min; UV detection: 220 nm; temperature: 40° C.].

Example 48A

Enantiomer 2

Yield: 2.8 g

R$_t$ 5.84 min; purity >98%; >96% ee

[column: Daicel Chiralpak AS-H, 5 μm, 250 mm×4.6 mm; mobile phase: isohexane/isopropanol 75:25 (v/v); flow rate: 1 ml/min; UV detection: 220 nm; temperature: 40° C.].

Example 49A

Rac-Cyclopentyl{4-[(5-oxo-2-phenyl-5,6-dihydro-4H-1,3,4-oxadiazin-4-yl)methyl]phenyl}acetic Acid

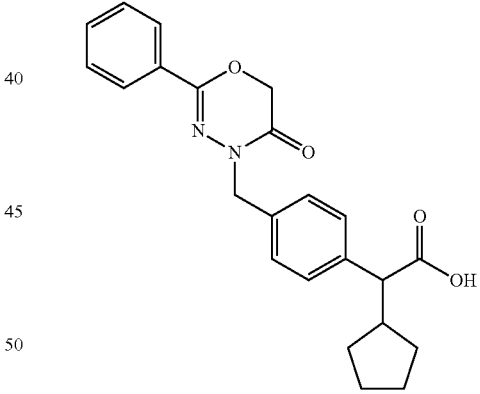

At room temperature, 22.67 ml (294.3 mmol) of trifluoroacetic acid were added slowly to a solution of 6.6 g (14.7 mmol) of tert-butyl cyclopentyl{4-[(5-oxo-2-phenyl-5,6-dihydro-4H-1,3,4-oxadiazin-4-yl)methyl]phenyl}acetate in 90 ml of dichloromethane, and the mixture was stirred overnight. The solvent was then removed under reduced pressure and the residue was taken up in 100 ml of ethyl acetate and extracted with 50 ml of water. The organic phase was dried over magnesium sulfate. After filtration, the solvent was removed under reduced pressure. This gave 4.8 g (12.23 mmol, 83% of theory) of a colorless solid.

$^1$H-NMR (400 MHz, DMSO-d$_6$, δ/ppm): 12.35-12.15 (1H, br. s), 7.78 (2H, d), 7.54-7.40 (3H, m), 7.29 (4H, s), 4.91 (2H, s), 4.83 (2H, s), 3.22 (1H, d), 2.48-2.35 (1H, m), 1.89-1.76 (1H, m), 1.68-1.46 (3H, m), 1.45-1.32 (1H, m), 1.32-1.14 (2H, m), 1.01-0.89 (1H, m).

LC-MS (Method 4): R$_t$=2.75 min; m/z=393 (M+H)$^+$.

The compounds listed in the table below were obtained in an analogous manner:

| Example | Name/Structure | Analytical data |
|---|---|---|
| 50A | 5,5,5-trifluoro-2-{4-[(5-oxo-2-phenyl-5,6-dihydro-4H-1,3,4-oxadiazin-4-yl)methyl]phenyl}pentanoic acid | $^1$H-NMR (400 MHz, DMSO-$d_6$, δ/ppm): 13.0-12.0 (1H, br. s), 7.77 (2H, d), 7.55-7.41 (3H, m), 7.35 (2H, d), 7.26 (2H, d), 4.92 (2H, s), 4.87 (2H, s), 3.67-3.53 (1H, m), 2.31-1.95 (3H, m), 1.89-1.74 (1H, m). LC-MS (Method 4): $R_t$ = 2.47 min; m/z = 421 $(M + H)^+$. |
| 51A | 3-methyl-2-{4-[(5-oxo-2-phenyl-5,6-dihydro-4H-1,3,4-oxadiazin-4-yl)methyl]phenyl}pentanoic acid | LC-MS (Method 2): $R_t$ = 2.15 min; m/z = 381 $(M + H)^+$. |
| 52A | cyclopentyl{4-[(6-oxo-3-phenylpyridazin-1(6H)-yl)-methyl]phenyl}acetic acid (enantiomer 1) | LC-MS (Method 2): $R_t$ = 2.11 min; m/z = 389 $(M + H)^+$. $[α]_D^{20}$ = +37.3°, c = 0.315, methanol. $^1$H-NMR (400 MHz, DMSO-$d_6$): δ = 12.15-12.31 (br. s, 1H), 8.09 (d, 1H), 7.89 (d, 2H), 7.43-7.53 (m, 3H), 7.25-7.34 (m, 4H), 7.09 (d, 1H), 5.30 (s, 2H), 3.21 (d, 1H), 2.34-2.47 (m, 1H), 1.75-1.89 (m, 1H), 1.32-1.66 (m, 4H), 1.15-1.31 (m, 2H), 0.87-0.99 (m, 1H). |

| Example | Name/Structure | Analytical data |
|---|---|---|
| 53A | cyclopentyl{4-[(6-oxo-3-phenylpyridazin-1(6H)-yl)-methyl]phenyl}acetic acid (enantiomer 2) 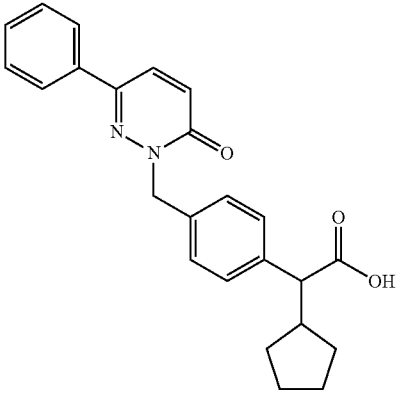 [SMILES: O=C(O)C(c1ccc(Cn2nc(-c3ccccc3)ccc2=O)cc1)C1CCCC1] | LC-MS (Method 2): $R_t$ = 2.11 min; m/z = 389 $(M + H)^+$. $[\alpha]_D^{20}$ = −21.0°, c = 0.265, methanol. |

Example 54A and Example 55A ent-Cyclopentyl{4-[(5-oxo-2-phenyl-5,6-dihydro-4H-1,3,4-oxadiazin-4-yl)methyl]phenyl}acetic Acid (Enantiomers 1 and 2)

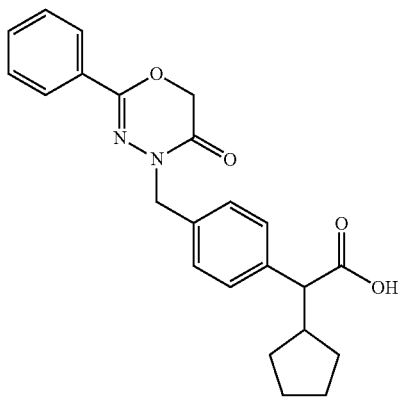 [SMILES: O=C(O)C(c1ccc(CN2N=C(c3ccccc3)OCC2=O)cc1)C1CCCC1]

75 g (191.1 mmol) of racemic cyclopentyl{4-[(5-oxo-2-phenyl-5,6-dihydro-4H-1,3,4-oxadiazin-4-yl)methyl]phenyl}acetic acid (Example 49A) were separated into the enantiomers by preparative HPLC on a chiral phase [column: chiral silica gel phase based on the selector poly(N-methacryloyl-L-isoleucine-3-pentylamide), 430 mm×40 mm; mobile phase: isohexane/ethyl acetate 1:1 (v/v); flow rate: 50 ml/min; temperature: 24° C.; UV detection: 270 nm]:

Example 54A

Enantiomer 1

Yield: 35 g
LC-MS (Method 4): $R_t$=2.75 min; m/z=393 (M+H)$^+$
$R_t$ 5.73 min; purity >99%; >99% ee
[column: chiral silica gel phase based on the selector poly(N-methacryloyl-L-isoleucine-3-pentylamide), 250 mm×4.6 mm; mobile phase: isohexane/ethyl acetate 1:1 (v/v); flow rate: 2 ml/min; temperature: 24° C.; UV detection: 270 nm].

Example 55A

Enantiomer 2

Yield: 32 g
$^1$H-NMR (400 MHz, DMSO-d$_6$, δ/ppm): 12.35-12.15 (1H, broad s), 7.78 (2H, d), 7.54-7.40 (3H, m), 7.29 (4H, s), 4.91 (2H, s), 4.83 (2H, s), 3.22 (1H, d), 2.48-2.35 (1H, m), 1.89-1.76 (1H, m), 1.68-1.46 (3H, m), 1.45-1.32 (1H, m), 1.32-1.14 (2H, m), 1.01-0.89 (1H, m).
LC-MS (Method 4): $R_t$=2.75 min; m/z=393 (M+H)$^+$
$R_t$ 6.86 min; purity >99%; >99% ee
[column: chiral silica gel phase based on the selector poly(N-methacryloyl-L-isoleucine-3-pentylamide), 250 mm×4.6 mm; mobile phase: isohexane/ethyl acetate 1:1 (v/v); flow rate: 2 ml/min; temperature: 24° C.; UV detection: 270 nm].
$[\alpha]_D^{20}$=+37.6°, c=0.445, methanol.

Examples 56A-59A

3-Methyl-2-{4-[(5-oxo-2-phenyl-5,6-dihydro-4H-1,3,4-oxadiazin-4-yl)methyl]phenyl}pentanoic Acid (Isomers 1-4)

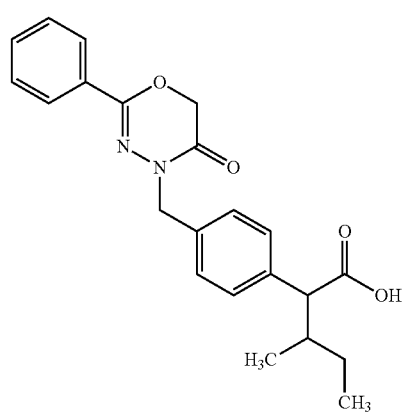 [SMILES: CCC(C)C(C(=O)O)c1ccc(CN2N=C(c3ccccc3)OCC2=O)cc1]

11.8 g (31.02 mmol) of the isomer mixture of 3-methyl-2-{4-[(5-oxo-2-phenyl-5,6-dihydro-4H-1,3,4-oxadiazin-4-yl)methyl]phenyl}pentanoic acid (Example 51A) were initially separated into the diastereomers by preparative HPLC on a chiral phase [column: chiral silica gel phase based on the selector poly(N-methacryloyl-D-valine-3-pentylamide), 500 mm×75 mm; mobile phase: iso-hexane/ethyl acetate 30:70 (v/v); flow rate: 200 ml/min; UV detection: 290 nm; temperature: 25° C.]. This gave 4.11 g and 5.2 g, respectively, of the two diastereomers.

Separation of Diastereomer 1:

4.11 g of diastereomer 1 were separated into the enantiomers (isomers 1 and 2) by preparative HPLC on a chiral phase [column: Daicel Chiralpak AD-H, 5 µm, 250 mm×20 mm; mobile phase: isohexane/isopropanol 95:5 (v/v); flow rate: 25 ml/min; UV detection: 230 nm; temperature: 24° C.]:

Example 56A

Isomer 1

Yield: 865 mg
$R_t$ 7.36 min; purity >91%; >93% ee
[column: Daicel Chiralpak AD-H, 5 µm, 250 mm×4 mm; mobile phase: isohexane/isopropanol 80:20 (v/v); flow rate: 1 ml/min; UV detection: 230 nm; temperature: 25° C.].
LC-MS (Method 2): $R_t$=2.16 min; m/z=381 (M+H)$^+$.

Example 57A

Isomer 2

Yield: 1662 mg
$R_t$ 7.91 min; purity >99%; >97% ee
[column: Daicel Chiralpak AD-H, 5 µm, 250 mm×4 mm; mobile phase: isohexane/isopropanol 80:20 (v/v); flow rate: 1 ml/min; UV detection: 230 nm; temperature: 25° C.].
LC-MS (Method 4): $R_t$=2.53 min; m/z=381 (M+H)$^+$.
$^1$H-NMR (400 MHz, DMSO-d$_6$, δ/ppm): 12.35-12.15 (1H, br. s), 7.78 (2H, d), 7.54-7.40 (3H, m), 7.31 (4H, q), 4.92 (2H, s), 4.86 (2H, s), 3.19 (1H, d), 2.09-1.95 (1H, m), 1.59-1.43 (1H, m), 1.25-1.09 (1H, m), 0.89 (3H, t), 0.58 (3H, d).
$[α]_D^{20}$=+21.7°, c=0.525, methanol.

Separation of Diastereomer 2:

5.2 g of diastereomer 2 were separated into the enantiomers (isomers 3 and 4) by preparative HPLC on a chiral phase [column: Daicel Chiralcel OJ-H, 5 µm, 250 mm×20 mm; mobile phase: isohexane/isopropanol 95:5 (v/v); flow rate: 25 ml/min; UV detection: 230 nm; temperature: 24° C.]:

Example 58A

Isomer 3

Yield: 2970 mg
$R_t$ 7.21 min; purity >94%; >99% ee
[column: Daicel Chiralcel OJ-H, 5 µm, 250 mm×4 mm; mobile phase: isohexane/isopropanol 80:20 (v/v); flow rate: 1 ml/min; UV detection: 230 nm; temperature: 25° C.].
LC-MS (Method 4): $R_t$=2.53 min; m/z=381 (M+H)$^+$.

Example 59A

Isomer 4

Yield: 1350 mg
$R_t$ 7.77 min; purity >90%; >84% ee
[column: Daicel Chiralcel OJ-H, 5 µm, 250 mm×4 mm; mobile phase: isohexane/isopropanol 80:20 (v/v); flow rate: 1 ml/min; UV detection: 230 nm; temperature: 25° C.].
LC-MS (Method 2): $R_t$=2.17 min; m/z=381 (M+H)$^+$.

Example 60A 4,4,4-Trifluoro-3-methyl-2-{4-[(5-oxo-2-phenyl-5,6-dihydro-4H-1,3,4-oxadiazin-4-yl)methyl]phenyl}butanoic Acid

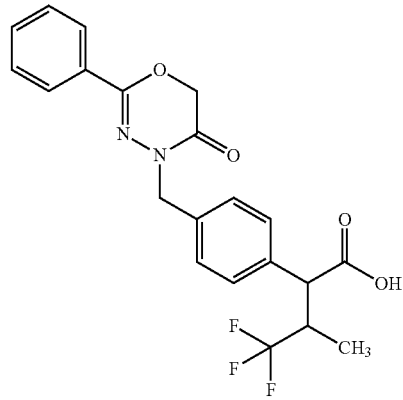 [SMILES: CC(C(C(=O)O)c1ccc(CN2N=C(c3ccccc3)OCC2=O)cc1)C(F)(F)F]

11.4 ml (11.4 mmol) of 1 N aqueous sodium hydroxide solution were added to a solution of 1283 mg (2.86 mmol) of ethyl 4,4,4-trifluoro-3-methyl-2-{4-[(5-oxo-2-phenyl-5,6-dihydro-4H-1,3,4-oxadiazin-4-yl)methyl]phenyl}butanoate in 10 ml of dioxane, and the mixture was stirred at 80° C. overnight. After the reaction had gone to completion, the dioxane was removed under reduced pressure and the solution that remained was diluted with water and then adjusted to pH 2 with 1 M hydrochloric acid. The precipitated solid was filtered off, washed with water and dried under reduced pressure at 45° C. overnight. This gave 1058 mg (2.52 mmol, 88% of theory) of the title compound as an isomer mixture.

LC-MS (Method 5): $R_t$=1.12 min, m/z=421 (M+H)$^+$ (diastereomer 1); $R_t$=1.13 min, m/z=421 (M+H)$^+$ (diastereomer 2).

Examples 61A-64A 4,4,4-Trifluoro-3-methyl-2-{4-[(5-oxo-2-phenyl-5,6-dihydro-4H-1,3,4-oxadiazin-4-yl)methyl]phenyl}butanoic Acid (Isomers 1-4)

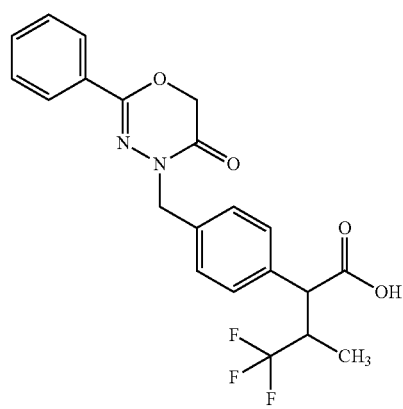 [SMILES: CC(C(C(=O)O)c1ccc(CN2N=C(c3ccccc3)OCC2=O)cc1)C(F)(F)F]

630 mg (1.50 mmol) of the isomer mixture of 4,4,4-trifluoro-3-methyl-2-{4-[(5-oxo-2-phenyl-5,6-dihydro-4H-1,3,4-oxadiazin-4-yl)methyl]phenyl}butanoic acid were separated into the isomers by preparative HPLC on a chiral phase [column: Daicel Chiralpak AD-H, 5 μm, 250 mm×20 mm; mobile phase: isohexane/(isopropanol+0.2% trifluoroacetic acid+1% water) 75:25 (v/v); flow rate: 15 ml/min; UV detection: 220 nm; temperature: 30° C.]:

Example 61A

Isomer 1

Yield: 26 mg $R_t$ 6.17 min; purity >99%; >99% ee
[column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 25° C.].

Example 62A

Isomer 2

Yield: 35 mg $R_t$ 6.57 min; purity >98%; >99% ee
[column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 25° C.].

Example 63A

Isomer 3

Yield: 236 mg $R_t$ 8.03 min; purity >99%; >99% ee
[column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 25° C.].

LC-MS (Method 5): $R_t$=1.12 min; m/z=421 (M+H)$^+$.

$^1$H-NMR (400 MHz, DMSO-d$_6$, δ/ppm): 12.60-12.81 (1H, br. s), 7.78 (2H, d), 7.41-7.53 (3H, m), 7.37 (4H, s), 4.93 (2H, s), 4.89 (2H, s), 3.61 (1H, d), 3.18-3.32 (1H, m), 0.77 (3H, d).

$[α]_D^{20}$=+45.6°, c=0.565, methanol.

Example 64A

Isomer 4

Yield: 247 mg $R_t$ 9.17 min; purity >99%; >98% ee [column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 25° C.].

$[α]_D^{20}$=−45.8°, c=0.305, methanol.

Example 65A

Tert-Butyl(+/−)-cyclopentyl{4-[(1-oxo-1,3-dihydro-2H-isoindol-2-yl)methyl]phenyl}acetate

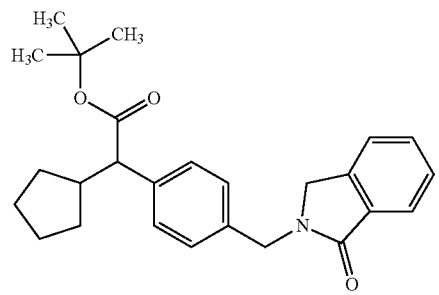 [SMILES: CC(C)(C)OC(=O)C(c1ccc(CN2Cc3ccccc3C2=O)cc1)C1CCCC1]

At 0° C., 611.3 mg (15.3 mmol, 60%) of sodium hydride were added to 2.035 g (15.3 mmol) of 1-oxoindoline in 12 ml of DMF. The mixture was stirred for 25 min, and 6.0 g (12.7 mmol, about 75% pure) of tert-butyl(+/−)-[4-(bromomethyl)phenyl](cyclopentyl)acetate were then added at 0° C. The reaction mixture was stirred for a further 4 h while slowly warming to RT, water was then added and the mixture was extracted twice with dichloromethane. The combined organic phases were washed with saturated sodium chloride solution, dried over magnesium sulfate and concentrated. In an ultrasonic bath, the crude product was treated with diethyl ether, and the solid was filtered off with suction and dried. This gave 3.40 g (65.2% of theory) of the target compound.

LC-MS (Method 4): $R_t$=1.05 min; m/z=406 (M+H)$^+$.

$^1$H-NMR (400 MHz, DMSO-d$_6$): δ=7.73 (d, 1H), 7.63-7.48 (m, 3H), 7.31 (d, 2H), 7.22 (d, 2H), 4.71 (s, 2H), 4.39 (s, 2H), 3.18 (d, 1H), 2.47 (m, 1H), 1.82 (m, 1H), 1.65-1.36 (m, 4H), 1.35 (s, 9H), 1.30-1.20 (m, 2H), 0.95 (m, 1H).

Example 66A

Tert-Butyl(+)-cyclopentyl{4-[(1-oxo-1,3-dihydro-2H-isoindol-2-yl)methyl]phenyl}acetate

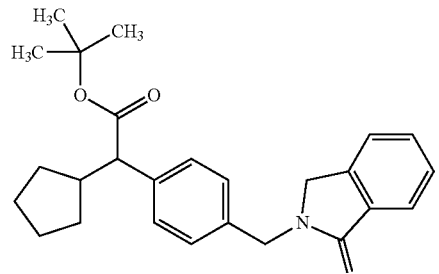

The racemate obtained in Example 65A was separated into the enantiomers by preparative HPLC on a chiral phase [column: Daicel Chiralpak IA-H, 5 μm, 250 mm×20 mm; flow rate: 15 ml/min; UV detection: 220 nm; injection volume: 0.25 ml; temperature: 30° C.; mobile phase: 20% acetonitrile/80% methyl tert-butyl ether]. 3.40 g of racemate gave 1.50 g of the (+)-enantiomer (the other enantiomer was not isolated in pure form).

LC-MS (Method 3): $R_t$=1.58 min; m/z=350 (M-$C_4H_8$+H)$^+$, 406 (M+H)$^+$.

$^1$H-NMR (400 MHz, DMSO-$d_6$): δ=7.73 (d, 1H), 7.63-7.48 (m, 3H), 7.31 (d, 2H), 7.22 (d, 2H), 4.71 (s, 2H), 4.39 (s, 2H), 3.18 (d, 1H), 2.47 (m, 1H), 1.82 (m, 1H), 1.65-1.36 (m, 4H), 1.35 (s, 9H), 1.30-1.20 (m, 2H), 0.95 (m, 1H).

$[α]_D^{20}$=+8.2°, c=0.38, chloroform.

Example 67A (+)-Cyclopentyl{4-[(1-oxo-1,3-dihydro-2H-isoindol-2-yl)methyl]phenyl}ethanoic Acid

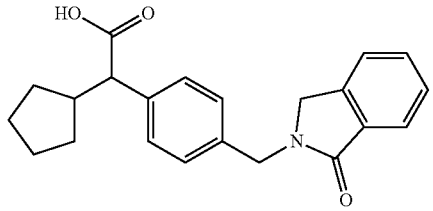 [SMILES: O=C(O)C(c1ccc(CN2Cc3ccccc3C2=O)cc1)C1CCCC1]

640 μl (7.4 mmol) of trifluoroacetic acid were added dropwise to a solution of 300 mg (0.740 mmol) of tert-butyl(+)-cyclopentyl{4-[(1-oxo-1,3-dihydro-2H-isoindol-2-yl)methyl]phenyl}-ethanoate in 1.5 ml dichloromethane. After 1 h of stirring, the reaction mixture was concentrated under reduced pressure and the residue was dried under high vacuum. This gave 267 mg (100% of theory) of the title compound.

LC-MS (Method 5): $R_t$=1.05 min; m/z=350 (M+H)$^+$.

$^1$H-NMR (400 MHz, DMSO-$d_6$): δ=7.73 (d, 1H), 7.57 (q, 2H), 7.50 (t, 1H), 7.31 (d, 2H), 7.22 (d, 2H), 4.71 (s, 2H), 4.37 (s, 2H), 3.22 (d, 1H), 2.41 (m, 1H), 1.83 (m, 1H), 1.65-1.16 (m, 6H), 0.94 (m, 1H).

Example 68A

Tert-Butyl 6-{[2-cyclopentyl-2-{4-[(5-oxo-2-phenyl-5,6-dihydro-4H-1,3,4-oxadiazin-4-yl)-methyl]phenyl}acetyl]amino}heptanoate (Diastereomer Mixture)

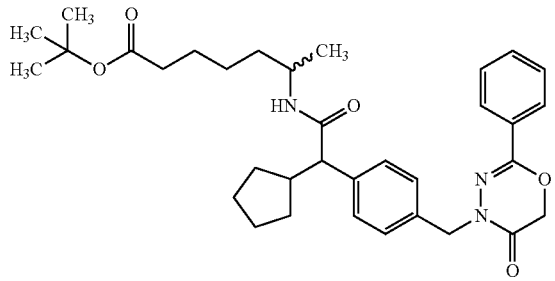 [SMILES: CC(CCCCC(=O)OC(C)(C)C)NC(=O)C(c1ccc(CN2N=C(c3ccccc3)OCC2=O)cc1)C1CCCC1]

At RT, 41.3 mg (0.306 mmol) of HOBt and 126 μl (0.764 mmol) of DIEA were added to a solution of 100 mg (0.255 mmol) of (+)-cyclopentyl{4-[(5-oxo-2-phenyl-5,6-dihydro-4H-1,3,4-oxadiazin-4-yl)methyl]phenyl}acetic acid and 76.9 mg (0.382 mmol) of tert-butyl(+/−)-6-aminoheptanoate in 0.3 ml of DMF. The resulting mixture was cooled to 0° C., after which 116.3 mg (0.306 mmol) of HATU were added. The reaction mixture was slowly warmed to RT, stirred at RT for 1 h and then diluted with ethyl acetate. The organic phase was washed with saturated sodium bicarbonate solution and with saturated sodium chloride solution, dried over sodium sulfate and concentrated under reduced pressure. The residue was purified by preparative RP-HPLC (acetonitrile/water gradient). This gave 118 mg (about 83% pure, about 67% of theory) of the target compound as a diastereomer mixture.

LC-MS (Method 3): $R_t$=1.59 min; m/z=576 (M+H)$^+$.

Example 69A

Tert-Butyl(+)-1-(4-{[2-cyclopentyl-2-{4-[(5-oxo-2-phenyl-5,6-dihydro-4H-1,3,4-oxadiazin-4-yl)methyl]phenyl}acetyl]amino}butyl)cyclopropanecarboxylate

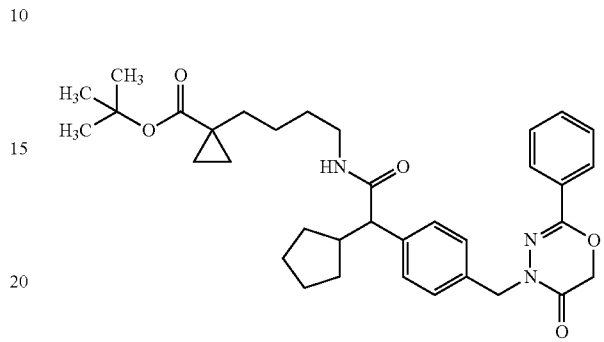

At RT, 266 μl (1.53 mmol) of DIEA were added to a solution of 545.8 mg (1.39 mmol) of (+)-cyclopentyl{4-[(5-oxo-2-phenyl-5,6-dihydro-4H-1,3,4-oxadiazin-4-yl)methyl]phenyl}acetic acid and 445 mg (about 2.09 mmol, crude material) of tert-butyl 1-(4-amino-butyl)cyclopropanecarboxylate in about 5 ml of DMF. The resulting mixture was cooled to 0° C., and four portions of altogether 687.4 mg (2.09 mmol) of HATU were then added. The reaction mixture was slowly warmed to RT, stirred at RT for 1 h and then added to water and extracted three times with ethyl acetate. The combined organic phases were dried over magnesium sulfate and concentrated under reduced pressure. The crude product was initially pre-purified by chromatography on silica gel (mobile phase gradient cyclohexane/ethyl acetate 5:1 to 3:1). Subsequent preparative RP-HPLC (acetonitrile/water gradient) gave 378 mg (46.2% of theory) of the target compound.

LC-MS (Method 2): $R_t$=2.73 min; m/z=588 (M+H)$^+$.

$^1$H-NMR (400 MHz, DMSO-$d_6$): δ=7.94 (t, 1H), 7.78 (d, 2H), 7.52-7.44 (m, 3H), 7.30 (d, 2H), 7.27 (d, 2H), 4.90 (s, 2H), 4.83 (s, 2H), 3.10 (d, 1H), 3.10-3.01 (m, 1H), 2.89-2.81 (m, 1H), 2.51-2.45 (m, 1H), 1.73-1.67 (m, 1H), 1.65-1.28 (m, 11H), 1.35 (s, 9H), 1.22-1.15 (m, 1H), 0.95 (m, 2H), 0.94-0.86 (m, 1H), 0.56 (m, 2H).

$[α]_D^{20}$=+50.4°, c=0.525, chloroform.

Example 70A

Tert-Butyl(+)-6-{[2-cyclopentyl-2-{4-[(5-oxo-2-phenyl-5,6-dihydro-4H-1,3,4-oxadiazin-4-yl)-methyl]phenyl}acetyl]amino}-2,2-dimethylhexanoate

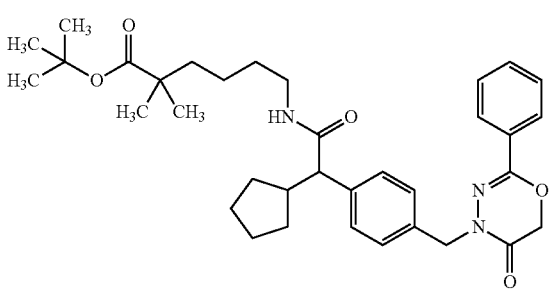 [SMILES: CC(C)(C)OC(=O)C(C)(C)CCCCNC(=O)C(c1ccc(CN2N=C(c3ccccc3)OCC2=O)cc1)C1CCCC1]

At RT, 160 μl (0.919 mmol) of DIEA were added to a solution of 328.1 mg (0.836 mmol) of (+)-cyclopentyl{4-[(5-oxo-2-phenyl-5,6-dihydro-4H-1,3,4-oxadiazin-4-yl)methyl]phenyl}acetic acid and 270 mg (about 1.25 mmol, crude material) of tert-butyl 6-amino-2,2-dimethylhexanoate in 3 ml of DMF. The resulting mixture was cooled to 0° C., and four portions of altogether 413.2 mg (1.09 mmol) of HATU were then added. The reaction mixture was slowly warmed to RT, stirred at RT for 16 h and then added to water and extracted three times with ethyl acetate. The combined organic phases were dried over sodium sulfate and concentrated under reduced pressure. Purification of the residue by preparative RP-HPLC (acetonitrile/water gradient) gave 179.8 mg (36.5% of theory) of the target compound.

LC-MS (Method 3): $R_t$=1.68 min; m/z=590 (M+H)$^+$.

$^1$H-NMR (400 MHz, DMSO-d$_6$): δ=7.94 (t, 1H), 7.79 (d, 2H), 7.51-7.42 (m, 3H), 7.31 (d, 2H), 7.27 (d, 2H), 4.90 (s, 2H), 4.85 (s, 2H), 3.11 (d, 1H), 3.10-3.01 (m, 1H), 2.88-2.80 (m, 1H), 2.51-2.45 (m, 1H), 1.75-1.68 (m, 1H), 1.60-1.07 (m, 12H), 1.36 (s, 9H), 1.22-1.15 (m, 1H), 0.98 (s, 6H), 0.92-0.85 (m, 1H).

$[α]_D^{20}$=+9.6°, c=0.570, chloroform.

Example 71A

Ethyl 6-{[2-cyclopentyl-2-{4-[(5-oxo-2-phenyl-5,6-dihydro-4H-1,3,4-oxadiazin-4-yl)methyl]-phenyl}acetyl]amino}-2-methylhexanoate (Diastereomer Mixture)

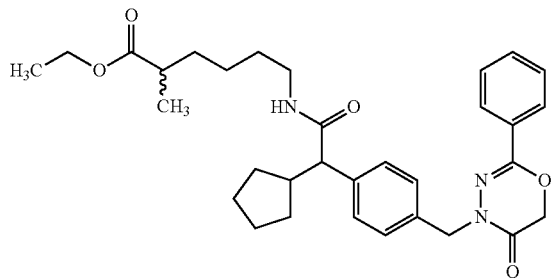 [SMILES: CCOC(=O)C(C)CCCCNC(=O)C(c1ccc(CN2N=C(c3ccccc3)OCC2=O)cc1)C1CCCC1]

At RT, 72 μl (0.415 mmol) of DIEA were added to a solution of 148 mg (0.377 mmol) of (+)-cyclopentyl{4-[(5-oxo-2-phenyl-5,6-dihydro-4H-1,3,4-oxadiazin-4-yl)methyl]phenyl}acetic acid and 98 mg (about 0.66 mmol, crude material) of ethyl 6-amino-2-methylhexanoate in 1.0 ml of DMF. The resulting mixture was cooled to 0° C., and four portions of altogether 186.4 mg (0.49 mmol) of HATU were then added. The reaction mixture was slowly warmed to RT, stirred at RT for 16 h and then added to water and extracted three times with ethyl acetate. The combined organic phases were dried over sodium sulfate and concentrated under reduced pressure. Purification of the residue by preparative RP-HPLC (acetonitrile/water gradient) gave 134.0 mg (64.9% of theory) of the target compound as a diastereomer mixture.

LC-MS (Method 3): $R_t$=1.51 min; m/z=548 (M+H)$^+$.

$^1$H-NMR (400 MHz, DMSO-d$_6$): δ=7.93 (t, 1H), 7.78 (d, 2H), 7.53-7.43 (m, 3H), 7.30 (d, 2H), 7.27 (d, 2H), 4.91 (s, 2H), 4.84 (s, 2H), 4.02 (q, 2H), 3.10 (d, 1H), 3.10-3.01 (m, 1H), 2.88-2.80 (m, 1H), 2.51-2.45 (m, 1H), 2.20 (q, 1H), 1.75-1.68 (m, 1H), 1.62-1.39 (m, 5H), 1.36-1.25 (m, 4H), 1.20-1.12 (m, including t, together 5H), 0.99 (d, 3H), 0.93-0.85 (m, 1H).

Example 72A and Example 73A

Ethyl 6-{[2-cyclopentyl-2-{4-[(5-oxo-2-phenyl-5,6-dihydro-4H-1,3,4-oxadiazin-4-yl)methyl]-phenyl}acetyl]amino}-2-methylhexanoate (Diastereomers 1 and 2)

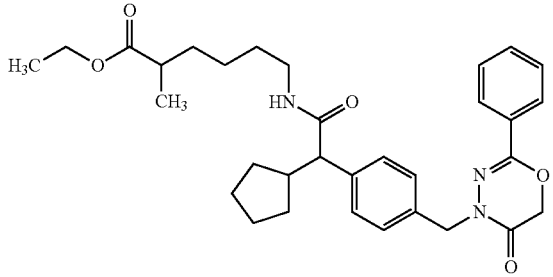 [SMILES: CCOC(=O)C(C)CCCCNC(=O)C(c1ccc(CN2N=C(c3ccccc3)OCC2=O)cc1)C1CCCC1]

The diastereomer mixture obtained above (95 mg) was separated by preparative HPLC on a chiral phase [column: Daicel Chiralpak IA, 5 μm, 250 mm×20 mm; injection volume: 3 ml; mobile phase: 90% tert-butyl methyl ether/10% methanol; flow rate: 25 ml/min; temperature: RT; detection: 260 nm]:

Example 72A

Diastereomer 1

Yield: 24 mg

LC-MS (Method 3): $R_t$=1.51 min; m/z=548 (M+H)$^+$.

$^1$H-NMR (500 MHz, CDCl$_3$): δ=7.82 (d, 2H), 7.48-7.30 (m, 7H), 5.48 (t, 1H), 4.91 (s, 2H), 4.75 (s, 2H), 4.11 (q, 2H), 3.30-3.20 (m, 1H), 3.14-3.08 (m, 1H), 2.94 (d, 1H), 2.61-2.55 (m, 1H), 2.39-2.34 (m, 1H), 1.96-1.91 (m, 1H), 1.65-1.58 (m, 2H), 1.48-1.35 (m, 4H), 1.20-1.10 (m, including t, together 5H), 1.10 (d, 3H), 0.99-0.84 (m, 2H).

$[α]_D^{20}$=+2°, c=0.280, chloroform.

Example 73A

Diastereomer 2

Yield: 23 mg

LC-MS (Method 3): $R_t$=1.51 min; m/z=548 (M+H)$^+$.

$^1$H-NMR (500 MHz, CDCl$_3$): δ=7.83 (d, 2H), 7.47-7.30 (m, 7H), 5.48 (t, 1H), 4.91 (s, 2H), 4.75 (s, 2H), 4.10 (q, 2H), 3.30-3.23 (m, 1H), 3.11-3.05 (m, 1H), 2.92 (d, 1H), 2.61-2.55 (m, 1H), 2.39-2.34 (m, 1H), 1.96-1.90 (m, 1H), 1.65-1.58 (m, 2H), 1.48-1.35 (m, 4H), 1.20-1.10 (m, including t, together 5H), 1.10 (d, 3H), 1.00-0.84 (m, 2H).

$[α]_D^{20}$=+13°, c=0.30, chloroform.

Example 74A

Tert-Butyl 1-(4-{[2-cyclopentyl-2-{4-[(5-oxo-2-phenyl-5,6-dihydro-4H-1,3,4-oxadiazin-4-yl)methyl]phenyl}acetyl]amino}pentyl)cyclopropanecarboxylate (Diastereomer Mixture)

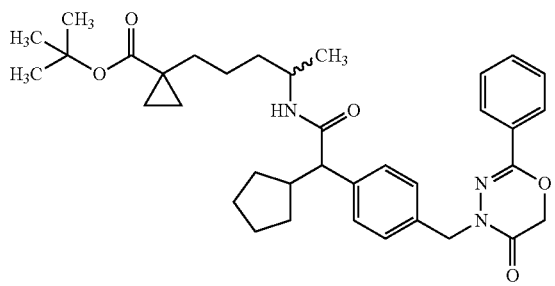 [SMILES: CC(CCCC1(C(=O)OC(C)(C)C)CC1)NC(=O)C(c1ccc(CN2N=C(c3ccccc3)OCC2=O)cc1)C1CCCC1]

At RT, 253 µl (1.45 mmol) of DIEA were added to a solution of 517.9 mg (1.32 mmol) of (+)-cyclopentyl{4-[(5-oxo-2-phenyl-5,6-dihydro-4H-1,3,4-oxadiazin-4-yl)methyl]phenyl}acetic acid and 450 mg (about 1.98 mmol, crude material) of tert-butyl 1-(4-aminopentyl)cyclo-propanecarboxylate in 2.5 ml of DMF. The resulting mixture was cooled to 0° C., and four portions of altogether 186.4 mg (0.49 mmol) of HATU were then added. The reaction mixture was slowly warmed to RT, stirred at RT for 16 h and then added to water and extracted three times with ethyl acetate. The combined organic phases were dried over magnesium sulfate and concentrated under reduced pressure. Purification of the crude product by preparative RP-HPLC (acetonitrile/water gradient) gave 540.0 mg (68.0% of theory) of the target compound as a diastereomer mixture.

LC-MS (Method 2): $R_t$=2.79 min, m/z=602 (M+H)$^+$ and $R_t$=2.83 min, m/z=602 (M+H)$^+$.

Example 75A and Example 76A

Tert-Butyl 1-(4-{[2-cyclopentyl-2-{4-[(5-oxo-2-phenyl-5,6-dihydro-4H-1,3,4-oxadiazin-4-yl)methyl]phenyl}acetyl]amino}pentyl)cyclopropanecarboxylate (Diastereomers 1 and 2)

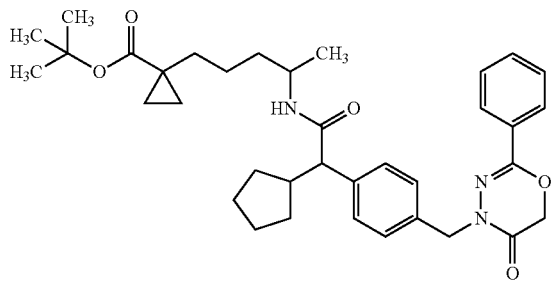 [SMILES: CC(CCCC1(C(=O)OC(C)(C)C)CC1)NC(=O)C(c1ccc(CN2N=C(c3ccccc3)OCC2=O)cc1)C1CCCC1]

The diastereomer mixture obtained above (536 mg) was separated by preparative HPLC on a chiral phase [column: Daicel Chiralpak IA, 5 µm, 250 mm×20 mm; injection volume: 2 ml; mobile phase: 90% tert-butyl methyl ether/10% methanol; flow rate: 20 ml/min; temperature: RT; detection: 260 nm]:

Example 75A

Diastereomer 1

Yield: 253 mg
LC-MS (Method 2): $R_t$=2.87 min; m/z=602 (M+H)$^+$.
$^1$H-NMR (400 MHz, DMSO-d$_6$): δ=7.80-7.75 (m, 3H), 7.54-7.43 (m, 3H), 7.30 (d, 2H), 7.26 (d, 2H), 4.91 (s, 2H), 4.84 (s, 2H), 3.67 (m, 1H), 3.09 (d, 1H), 2.52-2.43 (m, 1H), 1.76-1.68 (m, 1H), 1.63-1.56 (m, 1H), 1.55-1.28 (m, including s, together 19H), 1.27-1.17 (m, 1H), 0.98 (s, 2H), 0.97-0.85 (m, 1H), 0.88 (d, 3H), 0.62 (d, 2H).
$[α]_D^{20}$=+3.3°, c=0.550, chloroform.

Example 76A

Diastereomer 2

Yield: 273 mg
LC-MS (Method 2): $R_t$=2.82 min; m/z=602 (M+H)$^+$.
$^1$H-NMR (400 MHz, DMSO-d$_6$): δ=7.80-7.72 (m, 3H), 7.52-7.42 (m, 3H), 7.30 (d, 2H), 7.26 (d, 2H), 4.90 (s, 2H), 4.84 (s, 2H), 3.65 (m, 1H), 3.10 (d, 1H), 2.52-2.43 (m, 1H), 1.75-1.68 (m, 1H), 1.63-1.57 (m, 1H), 1.56-1.10 (m, including s, together 20H), 1.01 (d, 3H), 0.95-0.85 (m, 1H), 0.82 (d, 2H), 0.39 (dq, 2H).
$[α]_D^{20}$=+5.2°, c=0.555, chloroform.

Example 77A

Tert-Butyl(−)-1-(4-{[3-methyl-2-{4-[(5-oxo-2-phenyl-5,6-dihydro-4H-1,3,4-oxadiazin-4-yl)-methyl]phenyl}pentanoyl]amino}butyl)cyclopropanecarboxylate

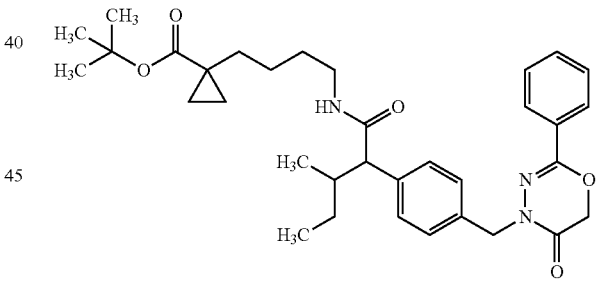

At RT, 106 µl (0.607 mmol) of DIEA were added to a solution of 210 mg (0.552 mmol) of (+)-3-methyl-2-{4-[(5-oxo-2-phenyl-5,6-dihydro-4H-1,3,4-oxadiazin-4-yl)methyl]phenyl}pentanoic acid (isomer 2) and 177 mg (0.828 mmol) of tert-butyl 1-(4-aminobutyl)cyclopropanecarboxylate in 2.0 ml of DMF. The resulting mixture was cooled to 0° C., and four portions of altogether 273 mg (0.718 mmol) of HATU were then added. The reaction mixture was slowly warmed to RT, stirred at RT for 16 h and then added to water and extracted three times with ethyl acetate. The combined organic phases were dried over sodium sulfate and concentrated under reduced pressure. Purification of the residue by preparative RP-HPLC (acetonitrile/water gradient) gave 264.0 mg (83.1% of theory) of the target compound.

LC-MS (Method 2): $R_t$=2.75 min; m/z=576 (M+H)$^+$.
$^1$H-NMR (400 MHz, DMSO-d$_6$): δ=7.94 (t, 1H), 7.77 (d, 2H), 7.49 (q, 1H), 7.44 (t, 2H), 7.27 (q, 4H), 4.90 (s, 2H), 4.83

(s, 2H), 3.04 (m, 2H), 2.83 (m, 1H), 2.05 (m, 1H), 1.46 (m, 1H), 1.39-1.23 (m, 15H), 1.08 (m, 1H), 0.90 (s, 2H), 0.86 (t, 3H), 0.53 (m, 5H).

$[\alpha]_D^{20}$=–1.4°, c=0.5, chloroform.

Example 78A

Ethyl 1-[(1E/Z)-4-{[-2-cyclopentyl-2-{4-[(5-oxo-2-phenyl-5,6-dihydro-4H-1,3,4-oxadiazin-4-yl)-methyl]phenyl}acetyl]amino}but-1-en-1-yl]cyclopropanecarboxylate

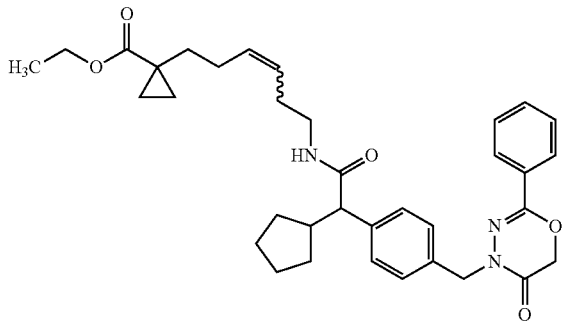 [SMILES: CCOC(=O)C1(CCC=CCCNC(=O)C(c2ccc(CN3N=C(c4ccccc4)OCC3=O)cc2)C2CCCC2)CC1]

200 mg (0.51 mmol) of (+)-cyclopentyl{4-[(5-oxo-2-phenyl-5,6-dihydro-4H-1,3,4-oxadiazin-4-yl)-methyl]phenyl}acetic acid were initially charged in 0.5 ml of DMF and 0.31 ml (3.82 mmol) of pyridine, 213.2 mg (0.561 mmol) of 1-[bis(dimethylamino)methylene]-5-chloro-3-oxy-1H-benzotriazol-1-ium tetrafluoroborate and 93.4 mg (0.51 mmol) of ethyl 1-[(1E/Z)-4-aminobut-1-en-1-yl]cyclopropanecarboxylate were added and the mixture was stirred at RT overnight. The reaction mixture was then diluted with a little acetonitrile and purified directly by preparative RP-HPLC (acetonitrile/water gradient). This gave 123 mg (41.8% of theory) of the target compound as an E/Z isomer mixture (about 1:4).

LC-MS (Method 3): $R_t$=1.51 min; m/z=558 (M+H)$^+$.

$^1$H-NMR (400 MHz, DMSO-d$_6$): δ=8.00 (t, 1H), 7.77 (d, 2H), 7.47 (m, 3H), 7.28 (q, 4H), 5.47 (m, 1H), 4.90 (s, 2H), 4.83 (s, 2H), 3.98 (m, 2H), 3.09 (d, 2H), 2.92 (m, 1H), 2.12 (m, 2H), 1.70 (m, 1H), 1.64-1.36 (m, 4H), 1.34-1.07 (m, 7H), 0.89 (m, 1H), 0.80 (d, 2H).

Example 79A

Tert-Butyl(+)-1-(4-{[2-cyclopentyl-2-{4-[(1-oxo-1,3-dihydro-2H-isoindol-2-yl)methyl]phenyl}-acetyl]amino}butyl)cyclopropanecarboxylate

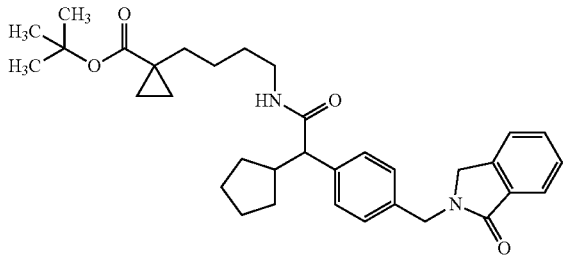 [SMILES: CC(C)(C)OC(=O)C1(CCCCNC(=O)C(c2ccc(CN3Cc4ccccc4C3=O)cc2)C2CCCC2)CC1]

At 0° C. and under argon, 390 μl (2.232 mmol) of N,N-diisopropylethylamine, 206.3 mg (0.967 mmol) of tert-butyl 1-(4-aminobutyl)cyclopropanecarboxylate and then, a little at a time, altogether 339.5 mg (0.893 mmol) of HATU were added to a solution of 260 mg (0.744 mmol) of (+)-cyclopentyl{4-[(1-oxo-1,3-dihydro-2H-isoindol-2-yl)methyl]phenyl}ethanoic acid and 120.7 mg (0.893 mmol) of 1-hydroxy-1H-benzotriazole hydrate in 2 ml of DMF. The mixture was stirred initially at 0° C. for 1 h and then at RT for 2 h. The reaction mixture was then poured into water and extracted three times with ethyl acetate. The combined organic phases were dried over magnesium sulfate and concentrated on a rotary evaporator. A little acetonitrile was added to the residue and the product was purified by preparative RP-HPLC (acetonitrile/water gradient). This gave 325 mg (80.3% of theory) of the target compound.

LC-MS (Method 2): $R_t$=2.51 min; m/z=545 (M+H)$^+$.

$^1$H-NMR (400 MHz, DMSO-d$_6$): δ=7.93 (t, 1H), 7.72 (d, 1H), 7.67 (q, 2H), 7.50 (t, 1H), 7.30 (d, 2H), 7.17 (d, 2H), 4.68 (s, 2H), 4.36 (s, 2H), 3.09 (d, 1H), 3.05 (m, 1H), 2.85 (m, 1H), 1.69 (m, 1H), 1.62-1.24 (m, 21H), 1.18 (m, 1H), 0.90 (q, 2H), 0.88 (m, 1H), 0.57 (q, 2H).

$[\alpha]_D^{20}$=+20.7°, c=0.345, chloroform.

Example 80A

Tert-Butyl Cis/trans-1-[4-{[2-cyclopentyl-2-{4-[(5-oxo-2-phenyl-5,6-dihydro-4H-1,3,4-oxadiazin-4-yl)methyl]phenyl}acetyl]amino}but-2-en-1-yl]cyclopropanecarboxylate

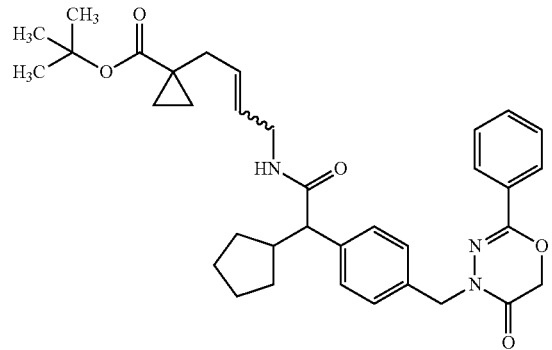 [SMILES: CC(C)(C)OC(=O)C1(CC=CCNC(=O)C(c2ccc(CN3N=C(c4ccccc4)OCC3=O)cc2)C2CCCC2)CC1]

At 0° C. and under argon, 143 μl (0.819 mmol) of N,N-diisopropylethylamine, 75.0 mg (about 0.35 mmol, crude material) of tert-butyl cis/trans-1-[(2E/Z)-4-aminobut-2-en-1-yl]cyclopropanecarboxylate and then, a little at a time, altogether 124.9 mg (0.328 mmol) of HATU were added to a solution of 107.2 mg (0.273 mmol) of (+)-cyclopentyl{4-[(5-oxo-2-phenyl-5,6-dihydro-4H-1,3,4-oxadiazin-4-yl)methyl] phenyl}ethanoic acid and 44.3 mg (0.328 mmol) of 1-hydroxy-1H-benzotriazole hydrate in 1.5 ml of DMF. The mixture was stirred initially at 0° C. for 1 h and then at RT for 2 h. The reaction mixture was then poured into water and extracted three times with ethyl acetate. The combined organic phases were dried over magnesium sulfate and concentrated under reduced pressure. A little acetonitrile was added to the residue and the product was purified by preparative RP-HPLC (acetonitrile/water gradient). This gave 121 mg (75.5% of theory) of the target compound (significant excess of trans isomer).

LC-MS (Method 3): $R_t$=1.63 min; m/z=530 (M-C$_4$H$_8$+H)$^+$.

Example 81A

Tert-Butyl Trans-1-[(2E)-4-{[2-cyclopentyl-2-{4-[(5-oxo-2-phenyl-5,6-dihydro-4H-1,3,4-oxadiazin-4-yl)methyl]phenyl}acetyl]amino}but-2-en-1-yl]cyclopropanecarboxylate

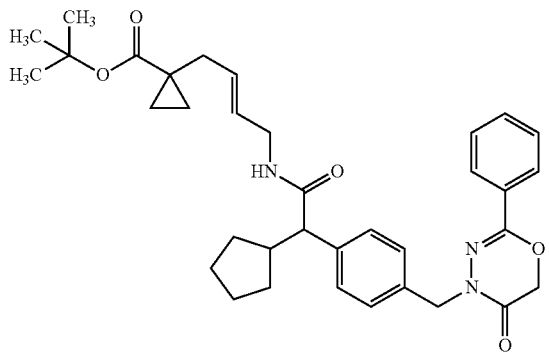 [SMILES: CC(C)(C)OC(=O)C1(C/C=C/CNC(=O)C(c2ccc(CN3N=C(c4ccccc4)OCC3=O)cc2)C2CCCC2)CC1]

The cis/trans isomer mixture obtained above (120 mg) was separated by preparative HPLC [column: Kromasil 100 C 18, 5 µm, 250 mm×20 mm; injection volume: 2 ml; mobile phase: 70% acetonitrile/30% aqueous formic acid (0.2%); flow rate: 25 ml/min; temperature: 35° C.; detection: 210 nm]:

Yield: 67 mg

LC-MS (Method 5): $R_t$=1.43 min; m/z=530 (M-C$_4$H$_8$+H)$^+$, 608 (M+Na)$^+$.

$^1$H-NMR (400 MHz, DMSO-d$_6$): δ=8.11 (t, 1H), 7.78 (d, 2H), 7.53-7.42 (m, 4H), 7.34-7.26 (m, 4H), 5.50-5.41 (m, 1H), 5.39-5.30 (m, 1H), 4.92 (s, 2H), 4.83 (s, 2H), 3.68-3.61 (m, 1H), 3.51-3.44 (m, 1H), 3.14 (d, 1H), 2.54-2.45 (m, 1H), 2.11 (d, 2H), 1.87-1.37 (m, 6H), 1.35 (s, 9H), 1.34-1.15 (m, 2H), 0.92 (m, 2H), 0.93-0.85 (m, 1H), 0.60 (m, 2H).

Example 82A

Ethyl Cis/trans-1-[4-{[2-cyclopentyl-2-{4-[(6-oxo-3-phenylpyridazin-[(6H)-yl)methyl]phenyl}-acetyl]amino}but-1-en-1-yl]cyclopropanecarboxylate

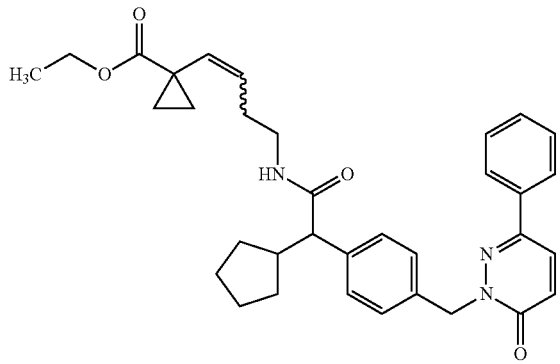 [SMILES: CCOC(=O)C1(C=CCCNC(=O)C(c2ccc(Cn3nc(-c4ccccc4)ccc3=O)cc2)C2CCCC2)CC1]

200 mg (0.515 mmol) of (+)-(2S)-cyclopentyl{4-[(6-oxo-3-phenylpyridazin-[(6H)-yl)methyl]-phenyl}ethanoic acid were dissolved in 1.2 ml of DMF, the mixture was cooled to 0° C. and 83.5 mg (0.618 mmol) of HOBt, 0.27 ml (1.55 mmol) of DIEA, 113.2 mg (about 0.618 mmol, crude material) of ethyl 1-[(1E/Z)-4-aminobut-1-en-1-yl]cyclopropanecarboxylate and a little at a time altogether 234.9 mg (0.618 mmol) of HATU were added in succession. The reaction mixture was stirred at 0° C. for 1 h and then slowly warmed to RT. The reaction mixture was then added to water and extracted repeatedly with ethyl acetate. The combined organic phases were dried over sodium sulfate and concentrated under reduced pressure. The crude product was purified by preparative RP-HPLC (acetonitrile/water gradient). This gave 160 mg (56.1% of theory) of the target compound as a cis/trans isomer mixture.

LC-MS (Method 2): $R_t$=2.41 min, m/z=554 (M+H)$^+$ and $R_t$=2.45 min, m/z=554 (M+H)$^+$.

Example 83A

Ethyl Trans-1-[(1E)-4-{[2-cyclopentyl-2-{4-[(6-oxo-3-phenylpyridazin-[(6H)-yl)methyl]phenyl}-acetyl]amino}but-1-en-1-yl]cyclopropanecarboxylate

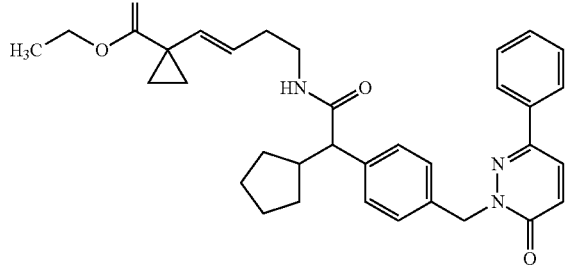

The cis/trans isomer mixture obtained above was separated by preparative HPLC [column: Kromasil 100 C 18, 5 µm, 250 mm×20 mm; injection volume: 0.5 ml; mobile phase: 75% acetonitrile/25% water; flow rate: 25 ml/min; temperature: 34.5° C.; detection: 210 nm]. 160 mg of mixture gave 11 mg of the trans isomer and 95 mg of the cis isomer (see Example 84A).

LC-MS (Method 3): $R_t$=1.46 min; m/z=554 (M+H)$^+$.

$^1$H-NMR (500 MHz, CDCl$_3$): δ=7.78 (d, 2H), 7.49-7.40 (m, 3H), 7.31 (d, 2H), 7.01 (d, 1H), 6.02 (d, 1H), 5.59 (t, 1H), 5.48 (s, 2H), 5.22 (dt, 1H), 4.11 (q, 2H), 3.28 (m, 1H), 3.14 (m, 1H), 2.95 (d, 1H), 2.58 (m, 1H), 2.13 (m, 2H), 1.92 (m, 1H), 1.55-1.38 (m, 5H), 1.35 (s, 2H), 1.24 (t, 3H), 1.24-1.18 (m, 2H), 0.99-0.87 (m, 3H).

Example 84A

Ethyl(−)-cis-1-[(1Z)-4-{[2-cyclopentyl-2-{4-[(6-oxo-3-phenylpyridazin-[(6H)-yl)methyl]phenyl}-acetyl]amino}but-1-en-1-yl]cyclopropanecarboxylate

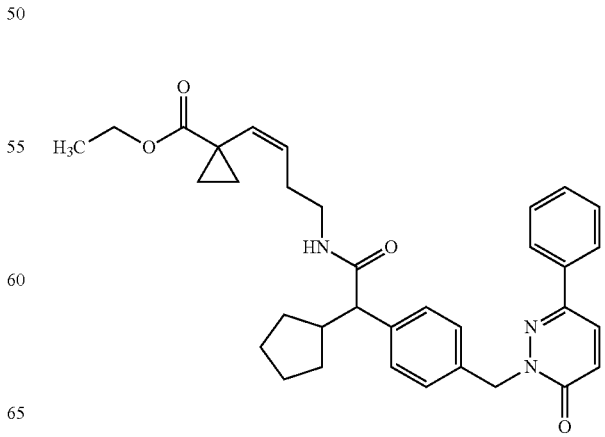

LC-MS (Method 5): $R_t$=1.31 min; m/z=554 (M+H)$^+$.

$^1$H-NMR (400 MHz, DMSO-d$_6$): δ=8.08 (d, 1H), 8.01 (t, 1H), 7.89 (d, 2H), 7.51-7.43 (m, 3H), 7.32-7.27 (m, 4H), 7.08 (d, 1H), 5.49-5.43 (m, 2H), 5.30 (s, 2H), 3.99 (q, 2H), 3.13-3.05 (m, 2H), 2.92 (m, 1H), 2.52-2.43 (m, 1H), 2.15-2.10 (m, 2H), 1.75-1.65 (m, 1H), 1.52-1.11 (m, 8H), 1.10 (t, 3H), 0.91-0.82 (m, 1H), 0.79 (m, 2H).

$[α]_D^{20}$=−21.1°, c=0.520, chloroform.

Example 85A

Methyl (1-{3-[(cyclopentyl{4-[(5-oxo-2-phenyl-5,6-dihydro-4H-1,3,4-oxadiazin-4-yl)methyl]-phenyl}acetyl)amino]propyl}cyclopropyl)acetate

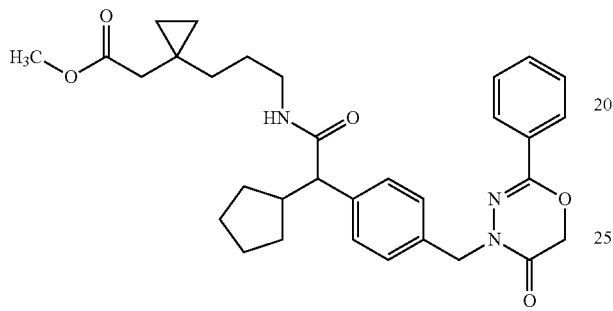

A solution of 591 mg (1.51 mmol) of cyclopentyl{4-[(5-oxo-2-phenyl-5,6-dihydro-4H-1,3,4-oxa-diazin-4-yl)methyl]phenyl}acetic acid (enantiomer 2), 376 mg (1.81 mmol) of methyl[1-(3-amino-propyl)cyclopropyl]acetate hydrochloride, 859 mg (2.26 mmol) of HATU and 1 ml of N,N-diiso-propylethylamine in 10 ml of DMF was stirred at room temperature overnight. After the reaction had ended, the mixture was poured into ice-water, the phases were separated and the aqueous phase was extracted three times with tert-butyl methyl ether. The combined organic phases were dried over sodium sulfate, and, after filtration, the solvent was removed to dryness under reduced pressure. The crude product obtained was purified by preparative RP-HPLC. This gave 233 mg (0.43 mmol, 28.5% of theory) of the title compound as a colorless oil.

LC-MS (Method 2): $R_t$=2.41 min; m/z=546 (M+H)$^+$.

Example 86A

Tert-Butyl 1-{4-[(cyclopentyl{4-[(6-oxo-3-phenylpyridazin-[(6H)-yl)methyl]phenyl}acetyl)-amino]butyl}cyclopropanecarboxylate

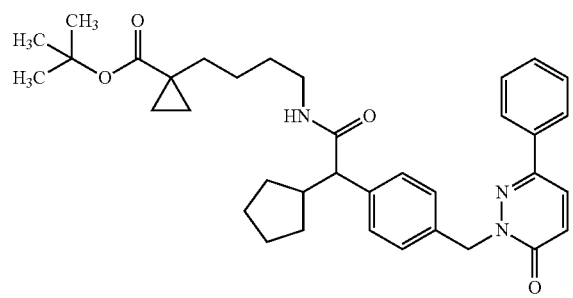 [SMILES: CC(C)(C)OC(=O)C1(CCCCNC(=O)C(c2ccc(Cn3nc(-c4ccccc4)ccc3=O)cc2)C2CCCC2)CC1]

A solution of 113 mg (0.29 mmol) of cyclopentyl{4-[(6-oxo-3-phenylpyridazin-[(6H)-yl)methyl]-phenyl}acetic acid (enantiomer 1), 75 mg (0.35 mmol) of tert-butyl 1-(4-aminobutyl)cyclo-propanecarboxylate, 167 mg (0.44 mmol) of HATU and 0.15 ml (0.88 mmol) of N,N-diisopropyl-ethylamine in 3.5 ml of DMF was stirred at room temperature overnight. After the reaction had ended, the mixture was poured into ice-water, the phases were separated and the aqueous phase was extracted three times with tert-butyl methyl ether. The combined organic phases were dried over sodium sulfate, and, after filtration, the solvent was removed to dryness under reduced pressure. This gave 197 mg of the crude title compound which was used without further purification for the subsequent reaction.

LC-MS (Method 5): $R_t$=1.42 min; m/z=584 (M+H)$^+$, 528 (M-C$_4$H$_8$+H)$^+$.

Example 87A

Methyl 7-[(cyclopentyl{4-[(5-oxo-2-phenyl-5,6-dihydro-4H-1,3,4-oxadiazin-4-yl)methyl]phenyl}-acetyl)amino]heptanoate

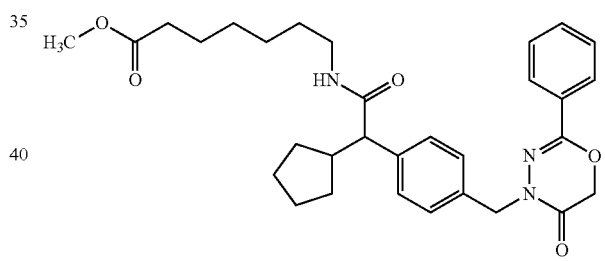

A solution of 72 mg (0.18 mmol) of cyclopentyl{4-[(5-oxo-2-phenyl-5,6-dihydro-4H-1,3,4-oxa-diazin-4-yl)methyl]phenyl}acetic acid (enantiomer 2), 30 mg (0.15 mmol) of methyl 7-amino-heptanoate hydrochloride, 87 mg (0.23 mmol) of HATU and 0.8 ml of pyridine in 3.2 ml of DMF was stirred at room temperature overnight. After the reaction had ended, the mixture was poured into ice-water, the phases were separated and the aqueous phase was extracted three times with tert-butyl methyl ether. The combined organic phases were dried over sodium sulfate, and, after filtration, the solvent was removed to dryness under reduced pressure. The crude product obtained was purified by preparative RP-HPLC. This gave 13 mg (0.02 mmol, 13% of theory) of the title compound as a colorless oil.

LC-MS (Method 4): $R_t$=2.79 min; m/z=534 (M+H)$^+$.

The compounds listed in the table below were obtained analogously to Example 85A:

| Example | Name/Structure/Starting materials | Analytical data |
| --- | --- | --- |
| 88A | methyl 4-[(cyclopentyl{4-[(5-oxo-2-phenyl-5,6-dihydro-4H-1,3,4-oxadiazin-4-yl)methyl]phenyl}-acetyl)amino]butanoate<br><br>(from cyclopentyl{4-[(5-oxo-2-phenyl-5,6-dihydro-4H-1,3,4-oxadiazin-4-yl)methyl]phenyl}acetic acid (enantiomer 2) and methyl 4-aminobutanoate hydrochloride) | LC-MS (Method 4):<br>$R_t$ = 2.62 min; m/z = 492 $(M + H)^+$. |
| 89A | methyl 5-[(cyclopentyl{4-[(5-oxo-2-phenyl-5,6-dihydro-4H-1,3,4-oxadiazin-4-yl)methyl]phenyl}-acetyl)amino]pentanoate<br><br>(from cyclopentyl{4-[(5-oxo-2-phenyl-5,6-dihydro-4H-1,3,4-oxadiazin-4-yl)methyl]phenyl}acetic acid (enantiomer 2) and methyl 5-aminopentanoate hydrochloride) | LC-MS (Method 4):<br>$R_t$ = 2.62 min; m/z = 506 $(M + H)^+$. |
| 90A | methyl 6-[(cyclopentyl{4-[(5-oxo-2-phenyl-5,6-dihydro-4H-1,3,4-oxadiazin-4-yl)methyl]phenyl}-acetyl)amino]hexanoate<br><br>(from cyclopentyl{4-[(5-oxo-2-phenyl-5,6-dihydro-4H-1,3,4-oxadiazin-4-yl)methyl]phenyl}acetic acid (enantiomer 2) and methyl 6-aminohexanoate hydrochloride) | LC-MS (Method 4):<br>$R_t$ = 2.70 min; m/z = 520 $(M + H)^+$. |

| Example | Name/Structure/Starting materials | Analytical data |
|---|---|---|
| 91A | methyl 6-[(5,5,5-trifluoro-2-{4-[(5-oxo-2-phenyl-5,6-dihydro-4H-1,3,4-oxadiazin-4-yl)methyl]phenyl}-pentanoyl)amino]hexanoate<br><br>(from 5,5,5-trifluoro-2-{4-[(5-oxo-2-phenyl-5,6-dihydro-4H-1,3,4-oxadiazin-4-yl)methyl]phenyl}-pentanoic acid and methyl 6-aminohexanoate hydrochloride) | LC-MS (Method 2):<br>$R_t$ = 2.24 min; m/z = 548 $(M + H)^+$. |
| 92A | tert-butyl 1-{4-[(4,4,4-trifluoro-3-methyl-2-{4-[(5-oxo-2-phenyl-5,6-dihydro-4H-1,3,4-oxadiazin-4-yl)methyl]-phenyl}butanoyl)amino]butyl}cyclopropanecarboxylate<br><br>(from 4,4,4-trifluoro-3-methyl-2-{4-[(5-oxo-2-phenyl-5,6-dihydro-4H-1,3,4-oxadiazin-4-yl)methyl]phenyl}-butanoic acid (isomer 3) and tert-butyl 1-(4-amino-butyl)cyclopropanecarboxylate) | LC-MS (Method 5):<br>$R_t$ = 1.39 min; m/z = 616 $(M + H)^+$.<br>$^1$H-NMR (400 MHz, DMSO-$d_6$, δ/ppm): 8.11 (1H, t), 7.77 (2H, d), 7.40-7.54 (3H, m), 7.33 (4H, s), 4.93 (2H, s), 4.88 (2H, s), 3.55 (1H, d), 3.17-3.29 (1H, m), 2.99-3.10 (1H, m), 2.76-2.88 (1H, m), 1.30-1.39 (2H, m), 1.35 (9H, s), 1.21-1.30 (4H, m), 0.87-0.96 (2H, m), 0.71 (3H, d), 0.51-0.60 (2H, m). |

Exemplary Embodiments

General Procedure 3: Cleavage of Tert-Butyl Esters to the Corresponding Carboxylic Acids

At 0° C. to RT, trifluoroacetic acid (TFA) is added dropwise to a solution of the tert-butyl ester in dichloromethane (concentration 0.1 to 1.0 mol/l additionally, optionally a drop of water) until a dichloromethane/TFA ratio of about 2:1 to 1:2 has been reached. The reaction mixture is stirred at RT for 1-18 h (if appropriate the mixture is warmed to 40° C. until complete conversion is achieved) and then concentrated under reduced pressure. The reaction product can, if required, be purified by crystallization from water/acetonitrile mixtures or by preparative RP-HPLC (mobile phase: acetonitrile/water gradient).

The following examples were prepared according to General Procedure 3:

| Example | Name/Structure/Starting material | Analytical data |
|---|---|---|
| 1 | (+)-1-(4-{[2-cyclopentyl-2-{4-[(5-oxo-2-phenyl-5,6-dihydro-4H-1,3,4-oxadiazin-4-yl)methyl]phenyl}-acetyl]amino}butyl)cyclopropanecarboxylic acid<br><br>from tert-butyl (+)-1-(4-{[2-cyclopentyl-2-{4-[(5-oxo-2-phenyl-5,6-dihydro-4H-1,3,4-oxadiazin-4-yl)-methyl]phenyl}acetyl]amino}butyl)cyclopropane-carboxylate | LC-MS (Method 2): $R_t$ = 2.15 min; m/z = 532 (M + H)$^+$.<br>$^1$H-NMR (400 MHz, DMSO-$d_6$): δ = 11.98 (s, 1H), 7.93 (t, 1H), 7.78 (d, 2H), 7.53-7.42 (m, 3H), 7.30 (d, 2H), 7.27 (d, 2H), 4.90 (s, 2H), 4.84 (s, 2H), 3.10 (d, 1H), 3.09-3.01 (m, 1H), 2.88-2.80 (m, 1H), 2.51-2.45 (m, 1H), 1.76-1.26 (m, 12H), 1.24-1.15 (m, 1H), 0.98 (d, 2H), 0.95-0.85 (m, 1H), 0.60 (d, 2H).<br>$[α]_D^{20}$ = +11.5°, c = 0.500, chloroform. |
| 2 | (+)-6-{[2-cyclopentyl-2-{4-[(5-oxo-2-phenyl-5,6-dihydro-4H-1,3,4-oxadiazin-4-yl)methyl]phenyl}-acetyl]amino}-2,2-dimethylhexanoic acid<br><br>from tert-butyl (+)-6-{[2-cyclopentyl-2-{4-[(5-oxo-2-phenyl-5,6-dihydro-4H-1,3,4-oxadiazin-4-yl)methyl]-phenyl}acetyl]amino}-2,2-dimethylhexanoate | LC-MS (Method 3): $R_t$ = 1.37 min; m/z = 534 (M + H)$^+$.<br>$^1$H-NMR (400 MHz, DMSO-$d_6$): δ = 12.00 (br. s, 1H), 7.95 (t, 1H), 7.79 (d, 2H), 7.51-7.42 (m, 3H), 7.31 (d, 2H), 7.27 (d, 2H), 4.90 (s, 2H), 4.34 (s, 2H), 3.11 (d, 1H), 3.09-3.02 (m, 1H), 2.88-2.80 (m, 1H), 2.51-2.45 (m, 1H), 1.76-1.66 (m, 1H), 1.63-1.24 (m, 10H), 1.23-1.09 (m, 4H), 1.01 (s, 6H), 0.95-0.80 (m, 2H).<br>$[α]_D^{20}$ = +15.2°, c = 0.520, chloroform. |
| 3 | 1-(4-{[2-cyclopentyl-2-{4-[(5-oxo-2-phenyl-5,6-dihydro-4H-1,3,4-oxadiazin-4-yl)methyl]phenyl}-acetyl]amino}pentyl)cyclopropanecarboxylic acid<br><br>from tert-butyl (+)-1-(4-{[2-cyclopentyl-2-{4-[(5-oxo-2-phenyl-5,6-dihydro-4H-1,3,4-oxadiazin-4-yl)methyl]phenyl}-acetyl]amino}pentyl)cyclopropanecarboxylate (diastereomer 1) | LC-MS (Method 2): $R_t$ = 2.22 min; m/z = 546 (M + H)$^+$.<br>$^1$H-NMR (400 MHz, DMSO-$d_6$): δ = 11.99 (s, 1H), 7.80-7.75 (m, 3H), 7.53-7.43 (m, 3H), 7.31 (d, 2H), 7.27 (d, 2H), 4.90 (s, 2H), 4.84 (s, 2H), 3.67 (m, 1H), 3.09 (d, 1H), 2.52-2.46 (m, 1H), 1.77-1.67 (m, 1H), 1.66-1.28 (m, 11H), 1.25-1.15 (m, 1H), 1.01 (m, 2H), 0.94-0.85 (m, 1H), 0.89 (d, 3H), 0.64 (m, 2H). |

| Example | Name/Structure/Starting material | Analytical data |
|---|---|---|
| 4 | (+)-1-(4-{[2-cyclopentyl-2-{4-[(5-oxo-2-phenyl-5,6-dihydro-4H-1,3,4-oxadiazin-4-yl)methyl]phenyl}-acetyl]amino}pentyl)cyclopropanecarboxylic acid<br><br>from tert-butyl (+)-1-(4-{[2-cyclopentyl-2-{4-[(5-oxo-2-phenyl-5,6-dihydro-4H-1,3,4-oxadiazin-4-yl)-methyl]phenyl}acetyl]amino}pentyl)cyclopropane-carboxylate (diastereomer 2) | LC-MS (Method 2): $R_t$ = 2.25 min; m/z = 546 (M + H)$^+$.<br>$^1$H-NMR (400 MHz, DMSO-$d_6$): δ = 11.92 (s, 1H), 7.80-7.74 (m, 3H), 7.53-7.43 (m, 3H), 7.31 (d, 2H), 7.28 (d, 2H), 4.90 (s, 2H), 4.84 (s, 2H), 3.65 (m, 1H), 3.09 (d, 1H), 2.52-2.46 (m, 1H), 1.75-1.65 (m, 1H), 1.62-1.10 (m, 12H), 0.99 (d, 3H), 0.94-0.85 (m, 1H), 0.87 (s, 2H), 0.59 (dq, 2H).<br>$[α]_D^{20}$ = +22.1°, c = 0.490, chloroform. |
| 5 | (+)-1-(4-{[3-methyl-2-{4-[(5-oxo-2-phenyl-5,6-dihydro-4H-1,3,4-oxadiazin-4-yl)methyl]phenyl}-pentanoyl]amino}butyl)cyclopropanecarboxylic acid<br><br>from tert-butyl (+)-1-(4-{[3-methyl-2-{4-[(5-oxo-2-phenyl-5,6-dihydro-4H-1,3,4-oxadiazin-4-yl)methyl]-phenyl}pentanoyl]amino}butyl)cyclopropane-carboxylate | LC-MS (Method 2): $R_t$ = 2.15 min; m/z = 520 (M + H)$^+$.<br>$^1$H-NMR (400 MHz, DMSO-$d_6$) δ = 7.96 (t, 1H), 7.77 (d, 2H), 7.47 (m, 3H), 7.28 (t, 4H), 4.90 (s, 2H), 4.83 (s, 2H), 3.06 (d, 2H), 2.80 (m, 1H), 2.06 (m, 1H), 1.47 (m, 1H), 1.36 (m, 2H), 1.29 (m, 4H), 1.09 (m, 1H), 0.97 (m, 2H), 0.87 (t, 3H), 0.56 (m, 5H).<br>$[α]_D^{20}$ = +5.5°, c = 0.495, chloroform. |
| 6 | (+)-1-(4-{[2-cyclopentyl-2-{4-[(1-oxo-1,3-dihydro-2H-isoindol-2-yl)methyl]phenyl}acetyl]amino}butyl)-cyclopropanecarboxylic acid<br><br>from tert-butyl (+)-1-(4-{[2-cyclopentyl-2-{4-[(1-oxo-1,3-dihydro-2H-isoindol-2-yl)methyl]phenyl}acetyl]-amino}butyl)cyclopropanecarboxylate | LC-MS (Method 3): $R_t$ = 1.21 min; m/z = 489 (M + H)$^+$.<br>$^1$H-NMR (400 MHz, DMSO-$d_6$): δ = 11.97 (s, 1H), 7.91 (t, 1H), 7.72 (d, 1H), 7.56 (m, 2H), 7.50 (t, 1H), 7.30 (d, 2H), 7.19 (d, 2H), 4.68 (s, 2H), 4.35 (s, 2H), 3.09 (d, 1H), 3.05 (m, 1H), 2.85 (m, 1H), 2.45 (m, 1H), 1.70 (m, 1H), 1.62-1.24 (m, 10H), 1.17 (m, 2H), 0.96 (d, 2H), 0.88 (m, 1H), 0.59 (d, 2H).<br>$[α]_D^{20}$ = +24.5°, c = 0.360, chloroform. |

| Example | Name/Structure/Starting material | Analytical data |
|---|---|---|
| 7 | 6-{[(2S)-2-cyclopentyl-2-{4-[(5-oxo-2-phenyl-5,6-dihydro-4H-1,3,4-oxadiazin-4-yl)methyl]phenyl}-acetyl]amino}heptanoic acid (diastereomer mixture)<br><br>![structure]<br><br>from tert-butyl 6-{[(2S)-2-cyclopentyl-2-{4-[(5-oxo-2-phenyl-5,6-dihydro-4H-1,3,4-oxadiazin-4-yl)methyl]-phenyl}acetyl]amino}heptanoate (diastereomer mixture) | LC-MS (Method 3): $R_t = 1.30$ min, m/z = 520 $(M + H)^+$ and $R_t = 1.31$ min, m/z = 520 $(M + H)^+$. |

Example 8 and Example 9

(+)-6-{[2-Cyclopentyl-2-{4-[(5-oxo-2-phenyl-5,6-dihydro-4H-1,3,4-oxadiazin-4-yl)methyl]-phenyl}acetyl]amino}heptanoic Acid (Diastereomer 1 and 2)

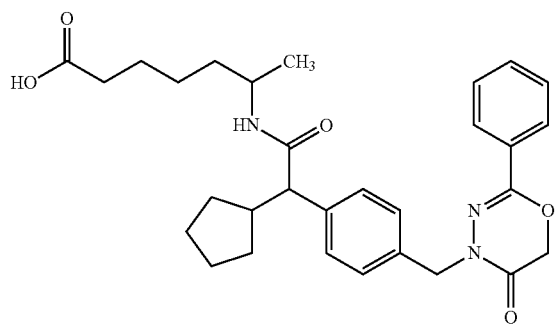 [SMILES: CC(CCCCC(=O)O)NC(=O)C(c1ccc(CN2N=C(c3ccccc3)OCC2=O)cc1)C1CCCC1]

The diastereomer mixture obtained in Example 7 (50 mg) was separated by preparative HPLC on a chiral phase [column: Daicel Chiralpak OJ-H, 5 μm, 250 mm×20 mm; injection volume: 0.6 ml; mobile phase: 70% isohexane/30% ethanol; flow rate: 20 ml/min; temperature: RT; detection: 230 nm]:

Example 8

Diastereomer 1

Yield: 21.8 mg

LC-MS (Method 3): $R_t$=1.32 min; m/z=520 $(M+H)^+$.

$^1$H-NMR (400 MHz, DMSO-$d_6$): δ=11.91 (br. s, 1H), 7.79-7.71 (m, 3H), 7.52-7.42 (m, 3H), 7.31 (d, 2H), 7.27 (d, 2H), 4.91 (s, 2H), 4.84 (s, 2H), 3.63 (m, 1H), 3.10 (d, 1H), 2.52-2.46 (m, 1H), 2.00 (t, 2H), 1.75-1.68 (m, 1H), 1.65-1.25 (m, 10H), 1.05-0.98 (m, 2H), 1.00 (d, 3H), 0.93-0.82 (m, 1H).

$[α]_D^{20}$=+13.0°, c=0.250, chloroform.

Example 9

Diastereomer 2

Yield: 22.7 mg

LC-MS (Method 4): $R_t$=2.53 min; m/z=520 $(M+H)^+$.

$^1$H-NMR (500 MHz, CDCl$_3$): δ=7.83 (d, 2H), 7.48-7.29 (m, 7H), 5.22 (br. d, 1H), 4.93 (s, 2H), 4.78 (s, 2H), 3.92 (m, 1H), 2.98 (d, 1H), 2.58-2.50 (m, 1H), 1.95-1.88 (m, 1H), 1.70-1.51 (m, 5H), 1.50-1.37 (m, 4H), 1.33-1.20 (m, 4H), 1.00 (d, 3H), 1.00-0.95 (m, 1H).

$[α]_D^{20}$=+5.0°, c=0.265, chloroform.

General Procedure 4: Hydrolysis of Methyl or Ethyl Esters to the Corresponding Carboxylic Acids At 0° C. to RT, 1.5 to 5 eq. of lithium hydroxide are added to a solution of the methyl or ethyl ester in THF, THF/methanol or THF/ethanol (concentration about 0.05 to 0.5 mol/l). The mixture is stirred for 0.5-18 h (warming to RT) and then neutralized or made slightly acidic with 1 N hydrochloric acid. If this results in the precipitation of a solid, the product can be isolated by filtration, washing with water and drying under high vacuum. Alternatively, the target compound is isolated directly from the crude product or after extractive work-up with dichloromethane or ethyl acetate by preparative RP-HPLC (mobile phase: water/acetonitrile gradient).

The following examples were prepared according to General Procedure 4:

| Example | Name/Structure/Starting material | Analytical data |
|---|---|---|
| 10 | (+)-6-{[2-cyclopentyl-2-{4-[(5-oxo-2-phenyl-5,6-dihydro-4H-1,3,4-oxadiazin-4-yl)methyl]phenyl}-acetyl]amino}-2-methylhexanoic acid (diastereomer 1)<br/>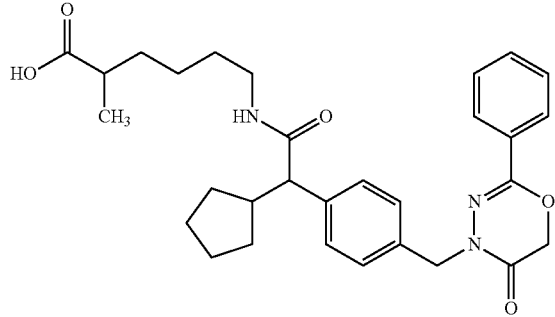 [SMILES: CC(CCCCNC(=O)C(c1ccc(CN2N=C(c3ccccc3)OCC2=O)cc1)C1CCCC1)C(=O)O]<br/>from ethyl (+)-6-{[2-cyclopentyl-2-{4-[(5-oxo-2-phenyl-5,6-dihydro-4H-1,3,4-oxadiazin-4-yl)-methyl]phenyl}acetyl]amino}-2-methylhexanoate (diastereomer 1) | LC-MS (Method 4): $R_t$ = 2.51 min; m/z = 520 (M + H)$^+$.<br/>$^1$H-NMR (400 MHz, DMSO-$d_6$): 12.00 (br. s, 1H), 7.95 (t, 1H), 7.78 (d, 2H), 7.53-7.43 (m, 3H), 7.30 (d, 2H), 7.27 (d, 2H), 4.91 (s, 2H), 4.84 (s, 2H), 3.11 (d, 1H), 3.10-3.02 (m, 1H), 2.53-2.46 (m, 1H), 2.22 (m, 2H), 1.75-1.65 (m, 1H), 1.62-1.15 (m, 12H), 0.99 (d, 3H), 0.95-0.84 (m, 1H).<br/>$[\alpha]_D^{20}$ = +11°, c = 0.405, chloroform. |
| 11 | (+)-6-{[2-cyclopentyl-2-{4-[(5-oxo-2-phenyl-5,6-dihydro-4H-1,3,4-oxadiazin-4-yl)methyl]phenyl}-acetyl]amino}-2-methylhexanoic acid (diastereomer 2)<br/>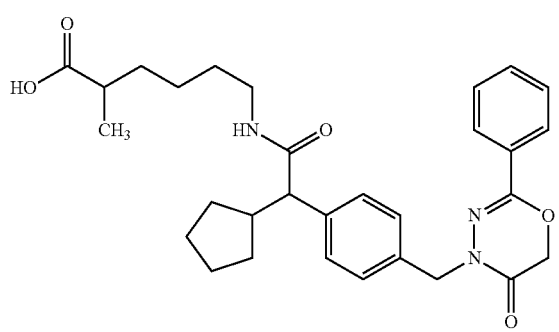 [SMILES: CC(CCCCNC(=O)C(c1ccc(CN2N=C(c3ccccc3)OCC2=O)cc1)C1CCCC1)C(=O)O]<br/>from ethyl (+)-6-{[2-cyclopentyl-2-{4-[(5-oxo-2-phenyl-5,6-dihydro-4H-1,3,4-oxadiazin-4-yl)-methyl]phenyl}acetyl]amino}-2-methylhexanoate (diastereomer 2) | LC-MS (Method 2): $R_t$ = 2.12 min; m/z = 520 (M + H)$^+$.<br/>$^1$H-NMR (500 MHz, CDCl$_3$): δ = 7.85 (d, 2H), 7.48-7.23 (m, 7H), 5.50 (br. s, 1H), 4.94 (s, 2H), 4.79 (s, 2H), 3.28-3.12 (m, 2H), 2.99 (d, 1H), 2.63-2.52 (m, 1H), 2.43-2.33 (m, 1H), 2.00-1.91 (m, 1H), 1.68-1.31 (m, 8H), 1.30-1.05 (m, 6H), 1.04-0.93 (m, 1H).<br/>$[\alpha]_D^{20}$ = +20°, c = 0.255, chloroform. |

Example 12

Cis/trans-1-[(4-{[2-Cyclopentyl-2-{4-[(5-oxo-2-phenyl-5,6-dihydro-4H-1,3,4-oxadiazin-4-yl)-methyl]phenyl}acetyl]amino}but-1-en-1-yl]cyclopropanecarboxylic Acid

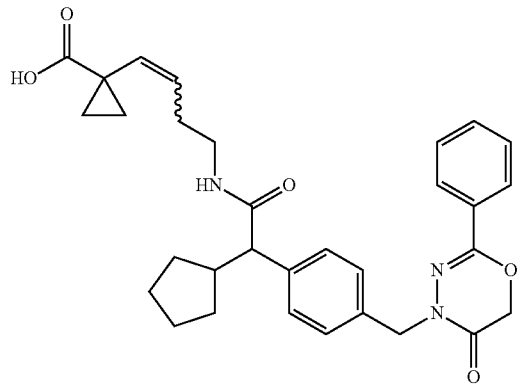 [SMILES: O=C(NCCC=CC1(C(=O)O)CC1)C(c1ccc(CN2N=C(c3ccccc3)OCC2=O)cc1)C1CCCC1]

86 mg (2.15 mmol) of sodium hydroxide were added to a solution of 120 mg (0.215 mmol) of ethyl cis/trans-1-[4-{[(+)-2-cyclopentyl-2-{4-[(5-oxo-2-phenyl-5,6-dihydro-4H-1,3,4-oxadiazin-4-yl)methyl]phenyl}acetyl]amino}but-1-en-1-yl]cyclopropanecarboxylate in 0.23 ml of THF and 0.56 ml of ethanol. The suspension was stirred at RT for 20 min and then acidified slightly with 1 N hydrochloric acid. The mixture was extracted three times with ethyl acetate. The combined organic phases were washed with saturated aqueous ammonium chloride solution, dried over magnesium sulfate and concentrated under reduced pressure. This gave 112 mg of the target compound as a cis/trans isomer mixture.

The cis/trans mixture obtained was then separated by preparative HPLC [column: Kromasil 100 C 18, 5 μm, 250 mm×20 mm; injection volume: 0.7 ml; mobile phase: 40% 0.2% strength trifluoroacetic acid/60% acetonitrile; flow rate: 25 ml/min; temperature: 40° C.; detection: 210 nm]. 112 mg of the stereoisomer mixture gave 66 mg of the cis isomer (see Example 13) and 11 mg of the trans isomer (see Example 14).

Example 13

Cis-1-[(1Z)-4-{[2-Cyclopentyl-2-{4-[(5-oxo-2-phenyl-5,6-dihydro-4H-1,3,4-oxadiazin-4-yl)-methyl]phenyl}acetyl]amino}but-1-en-1-yl]cyclopropanecarboxylic Acid

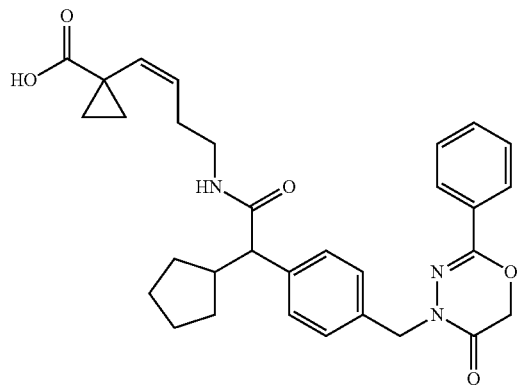 [SMILES: O=C(NCC/C=C\C1(C(=O)O)CC1)C(c1ccc(CN2N=C(c3ccccc3)OCC2=O)cc1)C1CCCC1]

LC-MS (Method 4): $R_t$=2.52 min; m/z=530 (M+H)$^+$.
$^1$H-NMR (400 MHz, DMSO-d$_6$): δ=7.98 (t, 1H), 7.77 (d, 2H), 7.46 (m, 3H), 7.28 (q, 4H), 5.50 (d, 1H), 5.40 (m, 1H), 4.90 (s, 2H), 4.82 (s, 2H), 3.09 (m, 2H), 2.90 (m, 1H), 2.47 (m, 1H), 2.15 (m, 2H), 1.69 (m, 1H), 1.62-1.34 (m, 4H), 1.28 (m, 1H), 1.22 (q, 2H), 1.16 (m, 1H), 0.88 (m, 1H), 0.77 (q, 2H).

Example 14 trans-1-[(1E)-4-{[2-Cyclopentyl-2-{4-[(5-oxo-2-phenyl-5,6-dihydro-4H-1,3,4-oxadiazin-4-yl)-methyl]phenyl}acetyl]amino}but-1-en-1-yl]cyclopropanecarboxylic Acid

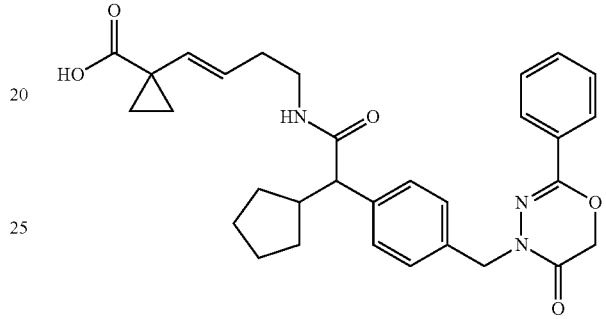

LC-MS (Method 4): $R_t$=2.50 min; m/z=530 (M+H)$^+$.
$^1$H-NMR (400 MHz, DMSO-d$_6$): δ=7.91 (t, 1H), 7.77 (d, 2H), 7.46 (m, 3H), 7.28 (q, 4H), 5.99 (d, 1H), 5.17 (m, 1H), 4.90 (s, 2H), 4.83 (s, 2H), 3.07 (m, 2H), 2.87 (m, 1H), 2.45 (m, 1H), 2.03 (q, 2H), 1.69 (m, 1H), 1.62-1.26 (m, 5H), 1.20 (d, 2H), 1.18 (m, 1H), 0.88 (m, 1H), 0.85 (q, 2H).

Example 15

(−)-trans-1-[(2E)-4-{[(2-Cyclopentyl-2-{4-[(5-oxo-2-phenyl-5,6-dihydro-4H-1,3,4-oxadiazin-4-yl)-methyl]phenyl}acetyl]amino}but-2-en-1-yl]cyclopropanecarboxylic Acid

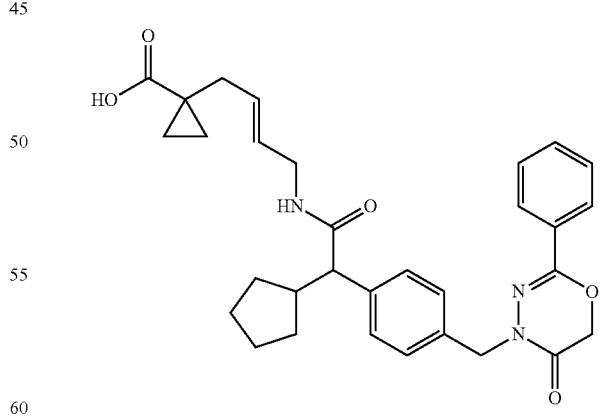

At RT, 0.12 ml of trifluoroacetic acid was added dropwise to a solution of 61 mg (0.104 mmol) of tert-butyl(−)-trans-1-[(2E)-4-{[2-cyclopentyl-2-{4-[(5-oxo-2-phenyl-5,6-dihydro-4H-1,3,4-oxadiazin-4-yl)methyl]phenyl}acetyl]amino}but-2-en-1-yl]cyclopropanecarboxylate in 0.1 ml of dichloromethane. The mixture was stirred at RT for 1 h, and another 0.12 ml of trifluoroacetic acid was then added. After a further 2 h at RT, the reaction mixture was concentrated under reduced pressure and the residue was purified by preparative RP-HPLC (acetonitrile/water gradient). This gave 42 mg (76.2% of theory) of the target compound.

LC-MS (Method 3): $R_t$=1.33 min; m/z=530 (M+H)$^+$.

$^1$H-NMR (400 MHz, DMSO-d$_6$): δ=12.08 (br. s, 1H), 8.09 (t, 1H), 7.88 (d, 2H), 7.53-7.42 (m, 3H), 7.33-7.26 (m, 4H), 5.53-5.45 (m, 1H), 5.38-5.30 (m, 1H), 4.91 (s, 2H), 4.83 (s, 2H), 3.70-3.60 (m, 1H), 3.49-3.40 (m, 1H), 3.18 (m, 1H), 2.12 (d, 2H), 1.77-1.15 (m, 7H), 0.98 (m, 2H), 0.96-0.86 (m, 1H), 0.62 (m, 2H).

$[\alpha]_D^{20}$=−1.1°, c=0.53, chloroform.

Example 16

(−)-cis-1-[(1Z)-4-{[2-Cyclopentyl-2-{4-[(6-oxo-3-phenylpyridazin-[(6H)-yl)methyl]phenyl}-acetyl]amino}but-1-en-1-yl]cyclopropanecarboxylic Acid

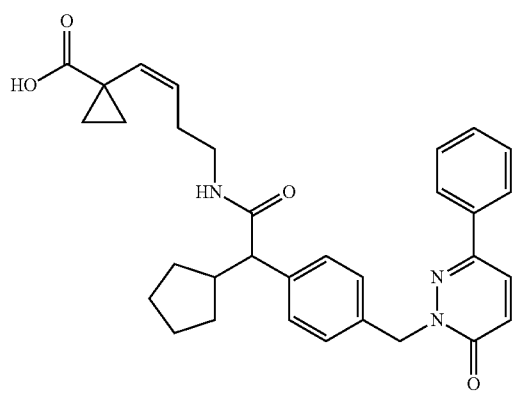 [SMILES: O=C(NCC/C=C\C1(C(=O)O)CC1)C(c1ccc(Cn2nc(-c3ccccc3)ccc2=O)cc1)C1CCCC1]

90 mg (0.163 mmol) of ethyl cis-1-[(1Z)-4-{[2-cyclopentyl-2-{4-[(6-oxo-3-phenylpyridazin-[(6H)-yl)methyl]phenyl}acetyl]amino}but-1-en-1-yl]cyclopropanecarboxylate were dissolved in a mixture of 100 µl of water, 100 µl of THF and 100 µl of methanol, and 17.1 mg (0.406 mmol) of lithium hydroxide were added at 0° C. The mixture was warmed to RT. Since no conversion was detected, a relatively large excess of sodium hydroxide was added, and the reaction mixture was stirred at RT overnight. The reaction mixture was then added to ice-water and acidified slightly with 1 N hydrochloric acid. The precipitated solid was filtered off with suction, washed repeatedly with water and dried under high vacuum. This gave 78 mg (91.3% of theory) of the target compound.

LC-MS (Method 5): $R_t$=1.13 min; m/z=526 (M+H)$^+$.

$^1$H-NMR (400 MHz, DMSO-d$_6$): δ=12.09 (s, 1H), 8.09 (d, 1H), 7.98 (t, 1H), 7.89 (m, 2H), 7.52-7.44 (m, 3H), 7.33-7.26 (m, 4H), 7.08 (d, 1H), 5.52-5.48 (m, 1H), 5.43-5.35 (m, 1H), 5.29 (s, 2H), 3.12-3.05 (m, 2H), 2.90 (m, 1H), 2.49 (m, 1H), 2.20-2.10 (m, 2H), 1.74-1.23 (m, 6H), 1.21 (m, 2H), 1.20-1.12 (m, 1H), 0.91-0.84 (m, 1H), 0.78 (m, 2H).

$[\alpha]_D^{20}$=−22.9°, c=0.520, chloroform.

Example 17

(−)-trans-1-[(1E)-4-{[2-Cyclopentyl-2-{4-[(6-oxo-3-phenylpyridazin-[(6H)-yl)methyl]phenyl}-acetyl]amino}but-1-en-1-yl]cyclopropanecarboxylic Acid

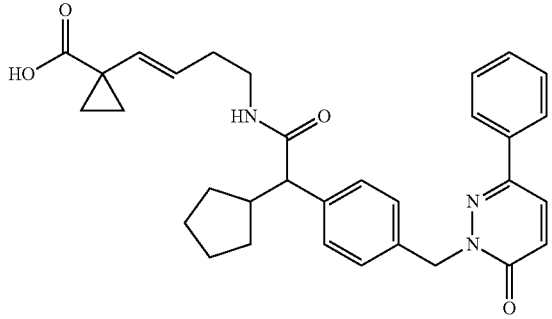 [SMILES: O=C(NCC/C=C/C1(C(=O)O)CC1)C(c1ccc(Cn2nc(-c3ccccc3)ccc2=O)cc1)C1CCCC1]

11.0 mg (0.020 mmol) of ethyl trans-1-[(1E)-4-{[2-cyclopentyl-2-{4-[(6-oxo-3-phenylpyridazin-1(6H)-yl)methyl]phenyl}acetyl]amino}but-1-en-1-yl]cyclopropanecarboxylate were dissolved in a mixture of 50 µl of water, 50 µl of THF and 50 µl of methanol, and 8 mg (0.2 mmol) of sodium hydroxide were added. The reaction mixture was stirred at RT for 3 h and then diluted with water, and the pH was adjusted to 2 using 1 N hydrochloric acid. The aqueous phase was extracted twice with ethyl acetate. The combined organic phases were dried over sodium sulfate and concentrated under reduced pressure. The residue was taken up in about 0.5 ml of 1,4-dioxane, frozen at −78° C. and lyophilized under high vacuum. This gave 9.6 mg (91.9% of theory) of the target compound.

LC-MS (Method 5): $R_t$=1.12 min; m/z=526 (M+H)$^+$.

$^1$H-NMR (400 MHz, DMSO-d$_6$): δ=12.18 (br. s, 1H), 8.07 (d, 1H), 7.95-7.88 (m, 3H), 7.53-7.44 (m, 3H), 7.34-7.27 (m, 4H), 7.09 (d, 1H), 5.99 (d, 1H), 5.29 (s, 2H), 5.18 (dt, 1H), 3.12-3.05 (m, 1H), 3.07 (d, 1H), 2.48 (m, 1H), 2.54-2.46 (m, 1H), 2.08-2.02 (m, 2H), 1.75-1.24 (m, 8H), 1.24-1.16 (m, 2H), 0.91-0.82 (m, 3H).

$[\alpha]_D^{20}$=−12.0°, c=0.235, chloroform.

Example 18

(1-{3-[(Cyclopentyl{4-[(5-oxo-2-phenyl-5,6-dihydro-4H-1,3,4-oxadiazin-4-yl)methyl]phenyl}-acetyl)amino]propyl}cyclopropyl)acetic Acid

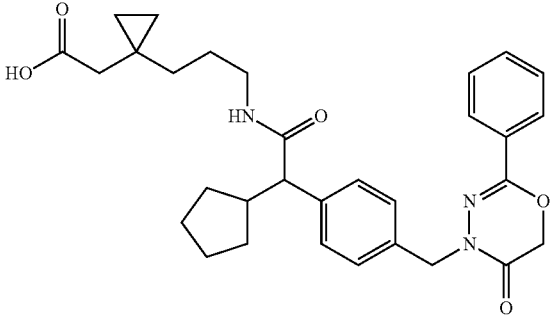 [SMILES: O=C(O)CC1(CCCNC(=O)C(c2ccc(CN3N=C(c4ccccc4)OCC3=O)cc2)C2CCCC2)CC1]

71 mg (1.69 mmol) of lithium hydroxide monohydrate were added to a solution of 230 mg (0.42 mmol) of methyl (1-{3-[(cyclopentyl{4-[(5-oxo-2-phenyl-5,6-dihydro-4H-1,3,4-oxadiazin-4-yl)methyl]phenyl}acetyl)amino]propyl}cyclopropyl)acetate in 2.8 ml of THF and 1.4 ml of water, and the mixture was stirred at RT overnight. After the reaction had gone to completion, the THF was removed under reduced pressure and the reaction solution was diluted with water and then adjusted to pH 2 with 1 M hydrochloric acid. The precipitated solid was filtered off, washed with water and dried under reduced pressure at 45° C. overnight. This gave 217 mg (0.41 mmol, 97% of theory) of the title compound as a white solid.

LC-MS (Method 2): $R_t$=2.14 min; m/z=532 (M+H)$^+$.

$^1$H-NMR (400 MHz, DMSO-d$_6$, δ/ppm): 12.20-11.80 (1H, br. s), 7.92 (1H, t), 7.77 (2H, d), 7.53-7.42 (3H, m), 7.28 (4H, q), 4.90 (2H, s), 4.83 (2H, s), 3.09 (1H, d), 3.06-2.97 (1H, m), 2.88-2.77 (1H, m), 2.56-2.44 (1H, m), 2.07 (2H, s), 1.75-1.65 (1H, m), 1.64-1.25 (7H, m), 1.23-1.10 (3H, m), 0.94-0.82 (1H, m), 0.34-0.25 (2H, m), 0.20-0.11 (2H, m).

Example 19

6-[(Cyclopentyl{4-[(5-oxo-2-phenyl-5,6-dihydro-4H-1,3,4-oxadiazin-4-yl)methyl]phenyl}acetyl)-amino]hexanoic Acid

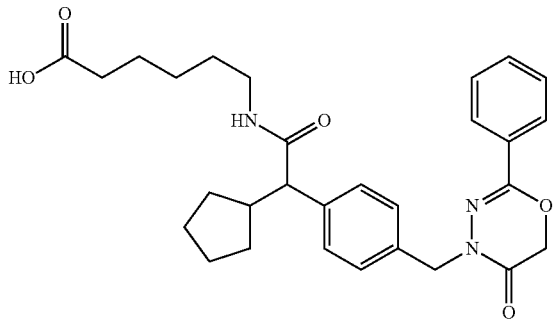 [SMILES: O=C(O)CCCCCNC(=O)C(c1ccc(CN2N=C(c3ccccc3)OCC2=O)cc1)C1CCCC1]

15 mg (0.62 mmol) of lithium hydroxide monohydrate were added to a solution of 160 mg (0.31 mmol) of methyl 6-[(cyclopentyl{4-[(5-oxo-2-phenyl-5,6-dihydro-4H-1,3,4-oxadiazin-4-yl)methyl]phenyl}acetyl)aminoThexanoate in 4 ml of THF and 4 ml of water, and the mixture was stirred at 60° C. overnight. The mixture was then adjusted to pH 4 using 1 M hydrochloric acid and extracted twice with ethyl acetate. The combined organic phases were dried over magnesium sulfate and then concentrated to dryness under reduced pressure. This gave 120 mg (0.24 mmol, 77% of theory) of the title compound as a white solid.

LC-MS (Method 3): $R_t$=1.26 min; m/z=506 (M+H)$^+$.

$^1$H-NMR (400 MHz, DMSO-d$_6$, δ/ppm): 11.96 (1H, s), 7.92 (1H, t), 7.77 (2H, d), 7.54-7.41 (3H, m), 7.28 (4H, q), 4.90 (2H, s), 4.83 (2H, s), 3.10 (1H, d), 3.07-2.99 (1H, m), 2.89-2.77 (1H, m), 2.52-2.41 (1H, m), 2.12 (2H, t), 1.76-1.65 (1H, m), 1.65-1.25 (9H, m), 1.25-1.10 (3H, m), 0.95-0.82 (1H, m).

Example 20

1-{4-[(Cyclopentyl{4-[(6-oxo-3-phenylpyridazin-[(6H)-yl)methyl]phenyl}acetyl)amino]butyl}-cyclopropanecarboxylic Acid

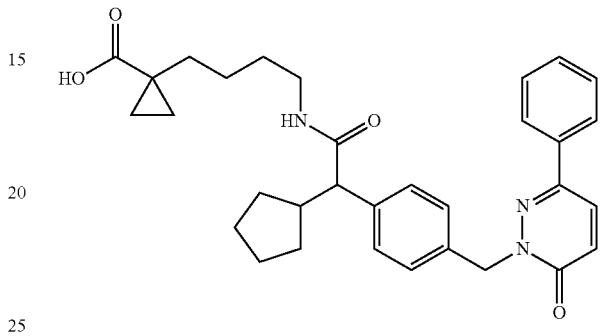

0.52 ml (6.74 mmol) of trifluoroacetic acid was added dropwise to a solution of 197 mg (0.34 mmol) of tert-butyl 1-{4-[(cyclopentyl{4-[(6-oxo-3-phenylpyridazin-[(6H)-yl)methyl]phenyl}-acetyl)amino]butyl}cyclopropanecarboxylate in 10 ml of dichloromethane, and the mixture was stirred at RT overnight. The reaction solution was then concentrated to dryness under reduced pressure. The residue was purified by preparative RP-HPLC. This gave 99 mg (0.19 mmol, 56% of theory) of the title compound.

LC-MS (Method 3): $R_t$=1.31 min; m/z=528 (M+H)$^+$.

$^1$H-NMR (400 MHz, DMSO-d$_6$, δ/ppm): 12.10-11.75 (1H, br. s), 8.07 (1H, d), 7.95-7.85 (3H, m), 7.53-7.42 (3H, m), 7.28 (4H, q), 7.08 (1H, d), 5.29 (2H, s), 3.09 (1H, d), 3.07-2.97 (1H, m), 2.89-2.76 (1H, m), 2.52-2.39 (1H, m), 1.75-1.64 (1H, m), 1.64-1.24 (11H, m), 1.21-1.10 (1H, m), 0.99-0.93 (2H, m), 0.93-0.82 (1H, m), 0.62-0.50 (2H, m).

The compounds listed in the table below were obtained in an analogous manner:

| Example | Name/Structure/Starting material | Analytical data |
| --- | --- | --- |
| 21 | 4-[(cyclopentyl{4-[(5-oxo-2-phenyl-5,6-dihydro-4H-1,3,4-oxadiazin-4-yl)methyl]phenyl}acetyl)amino]-butanoic acid 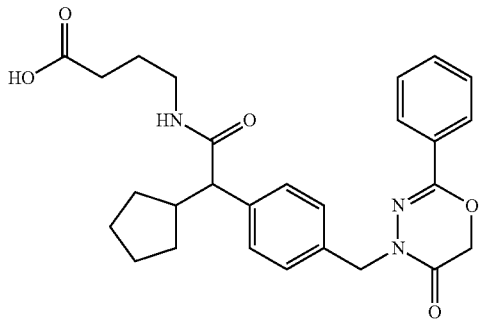 [SMILES: O=C(O)CCCNC(=O)C(c1ccc(CN2N=C(c3ccccc3)OCC2=O)cc1)C1CCCC1] (from methyl 4-[(cyclopentyl{4-[(5-oxo-2-phenyl-5,6-dihydro-4H-1,3,4-oxadiazin-4-yl)methyl]phenyl}-acetyl)amino]butanoate) | LC-MS (Method 2): $R_t$ = 1.94 min; m/z = 478 (M + H)$^+$. |

| Example | Name/Structure/Starting material | Analytical data |
|---|---|---|
| 22 | 5-[(cyclopentyl{4-[(5-oxo-2-phenyl-5,6-dihydro-4H-1,3,4-oxadiazin-4-yl)methyl]phenyl}acetyl)amino]-pentanoic acid<br>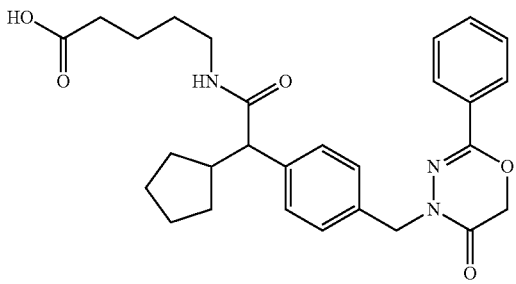 [SMILES: O=C(O)CCCCNC(=O)C(c1ccc(CN2N=C(c3ccccc3)OCC2=O)cc1)C1CCCC1]<br>(from methyl 5-[(cyclopentyl{4-[(5-oxo-2-phenyl-5,6-dihydro-4H-1,3,4-oxadiazin-4-yl)methyl]phenyl}-acetyl)amino]pentanoate) | LC-MS (Method 2): $R_t$ = 1.98 min; m/z = 492 $(M + H)^+$.<br>$^1$H-NMR (400 MHz, DMSO-$d_6$, δ/ppm): 11.97 (1H, s), 7.96 (1H, t), 7.77 (2H, d), 7.53-7.42 (3H, m), 7.28 (4H, q), 4.91 (2H, s), 4.83 (2H, s), 3.14-3.02 (2H, m), 2.88-2.77 (1H, m), 2.52-2.41 (1H, m), 2.16 (2H, t), 1.77-1.65 (1H, m), 1.65-1.25 (9H, m), 1.25-1.10 (1H, m), 0.95-0.82 (1H, m). |
| 23 | 7-[(cyclopentyl{4-[(5-oxo-2-phenyl-5,6-dihydro-4H-1,3,4-oxadiazin-4-yl)methyl]phenyl}acetyl)amino]-heptanoic acid<br>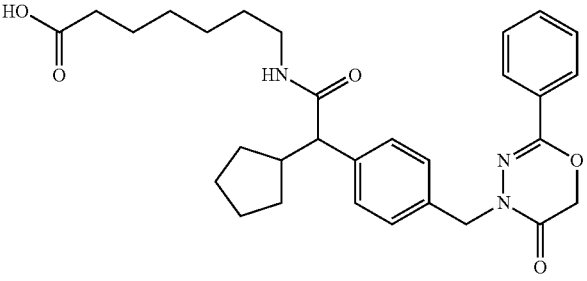 [SMILES: O=C(O)CCCCCCNC(=O)C(c1ccc(CN2N=C(c3ccccc3)OCC2=O)cc1)C1CCCC1]<br>(from methyl 7-[(cyclopentyl{4-[(5-oxo-2-phenyl-5,6-dihydro-4H-1,3,4-oxadiazin-4-yl)methyl]phenyl}-acetyl)amino]heptanoate) | LC-MS (Method 2): $R_t$ = 2.10 min; m/z = 520 $(M + H)^+$. |
| 24 | 1-{4-[(4,4,4-trifluoro-3-methyl-2-{4-[(5-oxo-2-phenyl-5,6-dihydro-4H-1,3,4-oxadiazin-4-yl)methyl]-phenyl}-butanoyl)amino]butyl}cyclopropanecarboxylic acid<br>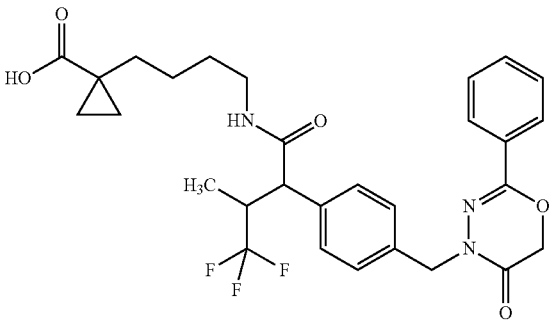 [SMILES: CC(C(C(=O)NCCCCC1(C(=O)O)CC1)c1ccc(CN2N=C(c3ccccc3)OCC2=O)cc1)C(F)(F)F]<br>(from tert-butyl 1-{4-[(4,4,4-trifluoro-3-methyl-2-{4-[(5-oxo-2-phenyl-5,6-dihydro-4H-1,3,4-oxadiazin-4-yl)methyl]phenyl}butanoyl)amino]butyl}cyclo-propanecarboxylate) | LC-MS (Method 3): $R_t$ = 1.31 min; m/z = 560 $(M + H)^+$.<br>$^1$H-NMR (400 MHz, DMSO-$d_6$, δ/ppm): 11.97 (1H, br. s), 8.09 (1H, t), 7.77 (2H, d), 7.41-7.54 (3H, m), 7.31 (4H, s), 4.92 (2H, s), 4.87 (2H, s), 3.55 (1H, d), 3.17-3.30 (1H, m), 2.97-3.08 (1H, m), 2.75-2.87 (1H, m), 1.31-1.41 (2H, m), 1.20-1.31 (4H, m), 0.91-1.00 (2H, m), 0.71 (3H, d), 0.51-0.61 (2H, m). |

Example 25

(+/−)-6-[(5,5,5-Trifluoro-2-{4-[(5-oxo-2-phenyl-5,6-dihydro-4H-1,3,4-oxadiazin-4-yl)methyl]-phenyl}pentanoyl)amino]hexanoic Acid

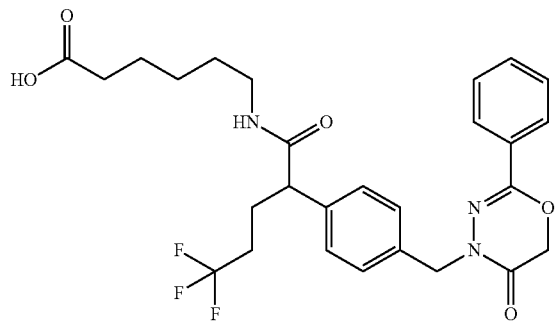 [SMILES: O=C(O)CCCCCNC(=O)C(CCC(F)(F)F)c1ccc(CN2N=C(c3ccccc3)OCC2=O)cc1]

33 mg (0.80 mmol) of lithium hydroxide monohydrate were added to a solution of 109 mg (0.20 mmol) of methyl 6-[(5,5,5-trifluoro-2-{4-[(5-oxo-2-phenyl-5,6-dihydro-4H-1,3,4-oxadiazin-4-yl)methyl]phenyl}pentanoyl)aminoThexanoate in 2 ml of THF and 1 ml of water, and the mixture was stirred at RT overnight. The mixture was then adjusted to pH 2 using 1 M hydrochloric acid and extracted twice with ethyl acetate. The combined organic phases were dried over magnesium sulfate and then concentrated to dryness under reduced pressure. The crude product was purified by preparative RP-HPLC. This gave 59 mg (0.11 mmol, 56% of theory) of the title compound as a colorless oil.

LC-MS (Method 2): $R_t$=2.00 min; m/z=534 (M+H)$^+$.

$^1$H-NMR (400 MHz, DMSO-d$_6$, δ/ppm): 12.20-11.75 (1H, br. s), 8.04 (1H, t), 7.77 (2H, d), 7.53-7.41 (3H, m), 7.34-7.25 (4H, m), 4.91 (2H, s), 4.85 (2H, s), 3.48 (1H, t), 3.09-2.98 (1H, m), 2.97-2.85 (1H, m), 2.18-2.00 (5H, m), 1.84-1.71 (1H, m), 1.47-1.36 (2H, m), 1.36-1.27 (2H, m), 1.21-1.10 (2H, m).

Example 26 and Example 27

6-[(5,5,5-Trifluoro-2-{4-[(5-oxo-2-phenyl-5,6-dihydro-4H-1,3,4-oxadiazin-4-yl)methyl]phenyl}-pentanoyl)amino]hexanoic Acid (Enantiomers 1 and 2)

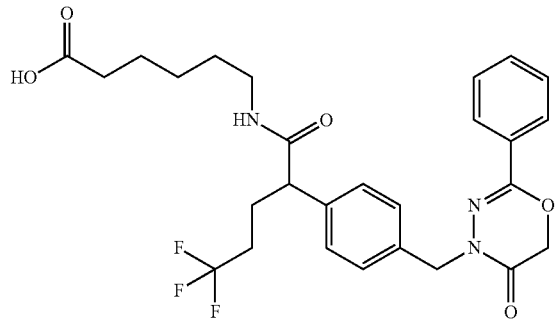 [SMILES: O=C(O)CCCCCNC(=O)C(CCC(F)(F)F)c1ccc(CN2N=C(c3ccccc3)OCC2=O)cc1]

52 mg (0.097 mmol) of the racemic (+/−)-6-[(5,5,5-trifluoro-2-{4-[(5-oxo-2-phenyl-5,6-dihydro-4H-1,3,4-oxadiazin-4-yl)methyl]phenyl}pentanoyl)amino]hexanoic acid obtained above were separated further by preparative HPLC on a chiral phase [column: Daicel Chiralpak AD-H, 5 μm, 250 mm×20 mm; mobile phase: isohexane/(isopropanol+0.2% trifluoroacetic acid+1% water) 75:25 (v/v); flow rate: 15 ml/min; UV detection: 220 nm; temperature: 30° C.]:

Example 26

Enantiomer 1

Yield: 10 mg $R_t$ 6.78 min; purity >99%; >99% ee

[column: Daicel Chiralpak AD-H, 5 μm, 250 mm×4.6 mm; mobile phase: isohexane/(isopropanol+0.2% trifluoroacetic acid+1% water) 75:25 (v/v); flow rate: 2 ml/min; UV detection: 220 nm; temperature: 25° C.]

$^1$H-NMR (400 MHz, DMSO-d$_6$, δ/ppm): 12.20-11.75 (1H, br. s), 8.04 (1H, t), 7.77 (2H, d), 7.53-7.41 (3H, m), 7.34-7.25 (4H, m), 4.91 (2H, s), 4.85 (2H, s), 3.48 (1H, t), 3.09-2.98 (1H, m), 2.97-2.85 (1H, m), 2.18-2.00 (5H, m), 1.84-1.71 (1H, m), 1.47-1.36 (2H, m), 1.36-1.27 (2H, m), 1.21-1.10 (2H, m).

Example 27

Enantiomer 2

Yield: 26 mg $R_t$ 7.41 min; purity >98%; >99% ee (analytical column see above)

LC-MS (Method 6): $R_t$=2.28 min; m/z=534 (M+H)$^+$.

B. ASSESSMENT OF THE PHARMACOLOGICAL ACTIVITY

The pharmacological effect of the compounds according to the invention can be shown in the following assays:

B-1. Vasorelaxant Effect In Vitro:

Rabbits are anesthetized and sacrificed by intravenous injection of thiopental sodium (about 50 mg/kg) and exsanguinated. The saphenous artery is removed and divided into rings 3 mm wide. The rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with carbogen and has the following composition: NaCl 119 mM; KCl 4.8 mM; CaCl$_2$×2 H$_2$O 1 mM; MgSO$_4$×7 H$_2$O 1.4 mM; KH$_2$PO$_4$ 1.2 mM; NaHCO$_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the level of the contraction achieved under the influence of the test substance is compared with the level of the contraction reached in the last preceding run. The concentration necessary to reduce the contraction reached in the preceding control by 50% is calculated from this (IC$_{50}$). The standard application volume is 5 μl. The proportion of DMSO in the bath solution corresponds to 0.1%.

Representative results for the compounds according to the invention are listed in Table 1:

TABLE 1

Vasorelaxant effect in vitro

| Example No. | $IC_{50}$ [nM] |
|---|---|
| 1 | 284 |
| 5 | 297 |
| 20 | 70 |

B-2. Stimulation of Recombinant Soluble Guanylate Cyclase (sGC) In Vitro:

Investigations on the stimulation of recombinant soluble guanylate cyclase (sGC) by the compounds according to the invention with and without sodium nitroprusside, and with and without the heme-dependent sGC inhibitor 1H-1,2,4-oxadiazolo-(4,3a)-quinoxalin-1-one (ODQ) are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. The heme-free guanylate cyclase is obtained by adding Tween 20 to the sample buffer (0.5% in the final concentration).

The activation of sGC by a test substance is reported as n-fold stimulation of the basal activity. The result for Example 1 is shown in Table 2:

TABLE 2

Stimulation (n-fold) of recombinant soluble guanylate cyclase (sGC) in vitro by Example 1

| Concentration | Heme-containing sGC | | | Heme-free sGC |
|---|---|---|---|---|
| Example 1 [µM] | Basal | +0.1 µM DEA/NO | +10 µM ODQ | Basal |
| 0 | 1.0 | 22.2 | 3.0 | 1.0 |
| 0.1 | 1.5 | 21.9 | 3.0 | 1.4 |
| 1 | 1.4 | 19.3 | 3.7 | 1.7 |
| 10 | 2.6 | 20.0 | 10.3 | 8.4 |
| 100 | 14.0 | 37.8 | 46.6 | 111.8 |

[DEA/NO = 2-(N,N-diethylamino)diazenolate 2-oxide; ODQ = 1H-1,2,4-oxadiazolo-(4,3a)-quinoxalin-1-one].

It is evident from Table 2 that stimulation both of the heme-containing and of the heme-free enzyme is achieved. Furthermore, combination of Example 1 and 2-(N,N-diethylamino)diazenolate 2-oxide (DEA/NO), an NO donor, shows no synergistic effect, i.e. the effect of DEA/NO is not potentiated as would be expected with an sGC activator acting via a heme-dependent mechanism. In addition, the effect of the sGC activator according to the invention is not blocked by the heme-dependent inhibitor of soluble guanylate cyclase ODQ, but is in fact increased. The results in Table 2 thus confirm the mechanism of action of the compounds according to the invention as activators of soluble guanylate cyclase.

B-3. Action at Recombinant Guanylate Cyclase Reporter Cell Lines

The cellular action of the compounds according to the invention is determined at a recombinant guanylate cyclase reporter cell line, as described in F. Wunder et al., *Anal. Biochem.* 339, 104-112 (2005).

Representative results for the compounds according to the invention are listed in Table 3:

TABLE 3 sGC-activating activity in the CHO reporter cell in vitro

| Example No. | MEC [nM] |
|---|---|
| 1 | 10 |
| 5 | 6.5 |
| 10 | 100 |
| 11 | 100 |
| 15 | 20 |
| 18 | 30 |
| 19 | 100 |
| 20 | 3 |
| 24 | 1 |

(MEC = minimum effective concentration).

B-4. Stimulation of Sgc Enzyme Activity

Soluble guanylate cyclase (sGC) converts on stimulation GTP into cGMP and pyrophosphate (PPi). PPi is detected with the aid of the assay described below. The signal produced in the assay increases as the reaction progresses and serves as a measure of the sGC enzyme activity under the given stimulation.

To carry out the assay, 29 µl of enzyme solution [0-10 nM soluble guanylate cyclase (prepared according to Honicka et al., *J. Mol. Med.* 77, 14-23 (1999)) in 50 mM TEA, 2 mM $MgCl_2$, 0.1% BSA (fraction V), 0.005% Brij®, pH 7.5] are initially introduced into a microplate, and 1 µl of the substance to be tested (as a serially diluted solution in DMSO) is added. The mixture is incubated at room temperature for 10 min. Then 20 µl of detection mix [1.2 nM Firefly Luciferase (Photinus pyralis luciferase, Promega), 29 µM dehydroluciferin (prepared according to Bitler & McElroy, *Arch. Biochem. Biophys.* 72, 358 (1957)), 122 µM luciferin (Promega), 153 µM ATP (Sigma) and 0.4 mM DTT (Sigma) in 50 mM TEA, 2 mM $MgCl_2$, 0.1% BSA (fraction V), 0.005% Brij®, pH 7.5] are added. The enzyme reaction is started by adding 20 µl of substrate solution [1.25 mM guanosine 5'-triphosphate (Sigma) in 50 mM TEA, 2 mM $MgCl_2$, 0.1% BSA (fraction V), 0.005% Brij®, pH 7.5] and measured continuously in a luminometer. The extent of the stimulation by the substance to be tested can be determined relative to the signal of the unstimulated reaction.

The activation of heme-free guanylate cyclase is examined by addition of 25 µM of 1H-1,2,4-oxadiazolo[4,3-a]quinoxalin-1-one (ODQ) to the enzyme solution and subsequent incubation for 30 minutes and compared to the stimulation of the native enzyme.

Representative results for the compounds according to the invention are listed in Table 4:

TABLE 4

Activating action at the sGC enzyme in vitro

| Example No. | MEC [nM] | $EC_{50}$ [nM] |
|---|---|---|
| 1 | 51 | n.d. |
| 5 | 58 | 1500 |

TABLE 4-continued

Activating action at the sGC enzyme in vitro

| Example No. | MEC [nM] | $EC_{50}$ [nM] |
|---|---|---|
| 20 | 13 | 650 |
| 24 | 5.5 | 184 |

(MEC = minimum effective concentration; $EC_{50}$ = concentration at 50% of maximum efficacy).

B-5. Radiotelemetric Measurement of Blood Pressure and Heart Rate on Conscious SH Rats A commercially available telemetry system from Data Sciences International DSI, USA, is employed for the measurements on conscious SH rats described below.

The system consists of 3 main components: (1) implantable transmitters, (2) receivers, which are linked via a multiplexer to a (3) data acquisition computer. The telemetry system makes it possible to continuously record the blood pressure and heart rate of conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 am and at 7.00 pm.

The telemetry transmitters (TAM PA-C40, DSI) as employed are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi, 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and layered closure of the wound is performed. An antibiotic (Tardomyocel COMP, Bayer, 1 ml/kg s.c.) is administered postoperatively for prophylaxis of infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated externally by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file created for this purpose and bearing the experiment number.

In the standard procedure, the following are measured for 10-second periods in each case: (1) systolic blood pressure (SBP), (2) diastolic blood pressure (DBP), (3) mean arterial pressure (MAP) and (4) heart rate (HR).

The acquisition of measured values is repeated under computer control at 5-minute intervals. The source data obtained as absolute value are corrected in the diagram with the currently measured barometric pressure and stored as individual data. Further technical details are given in the documentation from the manufacturing company (DSI).

The test substances are administered at 9.00 am on the day of the experiment. Following the administration, the parameters described above are measured over 24 hours. After the end of the experiment, the acquired individual data are sorted using the analysis software (Dataquest™ A.R.T. Analysis). The void value is assumed to be the time 2 hours before administration of the substance, so that the selected data set includes the period from 7.00 am on the day of the experiment to 9.00 am on the following day.

The data are smoothed over a presettable time by determination of the average (15-minute average, 30-minute average) and transferred as a text file to a storage medium. The measured values presorted and compressed in this way are transferred into Excel templates and tabulated.

C. EXEMPLARY EMBODIMENTS OF PHARMACEUTICAL COMPOSITIONS

The compounds according to the invention can be converted into pharmaceutical preparations in the following ways:

Tablet:
Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be administered orally:
Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:

500 mg of the compound according to the invention, 2.5 g of polysorbate and 97 g of polyethylene glycol 400.20 g of oral solution correspond to a single dose of 100 mg of the compound according to the invention.

Production:

The compound according to the invention is suspended in the mixture of polyethylene glycol and polysorbate with stir-

The invention claimed is:
1. A compound of the formula (I)

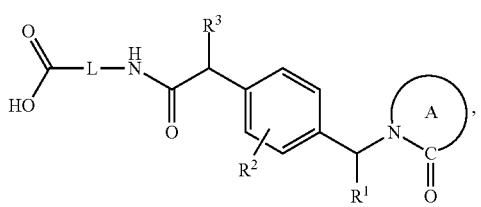

in which
ring A represents a 5- to 7-membered saturated or partially unsaturated oxo-substituted azaheterocycle attached via nitrogen,
  which (i) may contain one or two further heteroatoms from the group consisting of N, O and S as ring members,
  which (ii) is substituted by a radical selected from the group consisting of fluorine, chlorine, $(C_1\text{-}C_6)$-alkyl, trifluoromethyl, $(C_3\text{-}C_7)$-cycloalkyl, 4- to 7-membered monocyclic heterocyclyl having a total of 4 to 7 ring atoms, which contains one or two ring heteroatoms selected from the group consisting of N, O, and S, and phenyl or is benzo-fused,
    where the phenyl substituent and the fused phenyl ring for their part may be substituted up to two times by identical or different radicals selected from the group consisting of halogen, cyano, $(C_1\text{-}C_4)$-alkyl, $(C_2\text{-}C_4)$-alkenyl, trifluoromethyl, $(C_1\text{-}C_4)$-alkoxy and trifluoromethoxy,
  and
  which (iii) may additionally be substituted up to two times by identical or different further radicals selected from the group consisting of fluorine, chlorine, $(C_1\text{-}C_6)$-alkyl, trifluoromethyl, oxo, $(C_3\text{-}C_7)$-cycloalkyl, 4- to 7-membered heterocyclyl and phenyl,
    where phenyl for its part may be substituted up to two times by identical or different radicals selected from the group consisting of halogen, cyano, $(C_1\text{-}C_4)$-alkyl, $(C_2\text{-}C_4)$-alkenyl, trifluoromethyl, $(C_1\text{-}C_4)$-alkoxy and tri-fluoromethoxy,
$R^1$ represents hydrogen, $(C_1\text{-}C_4)$-alkyl or cyclopropyl,
$R^2$ represents hydrogen, halogen, cyano, $(C_1\text{-}C_4)$-alkyl or trifluoromethyl,
$R^3$ represents $(C_3\text{-}C_6)$-alkyl or $(C_3\text{-}C_6)$-alkenyl, each of which may be substituted by cyano, $(C_1\text{-}C_4)$-alkoxy or trifluoromethoxy and up to six times by fluorine,
  or
  represents $(C_3\text{-}C_7)$-cycloalkyl or $(C_3\text{-}C_7)$-cycloalkenyl, each of which may be substituted up to two times by identical or different radicals from the group consisting of $(C_1\text{-}C_4)$-alkyl, trifluoromethyl and $(C_1\text{-}C_4)$-alkoxy and also up to four times by fluorine,
  or
  represents oxetanyl, tetrahydrofuranyl or tetrahydropyranyl,
and
L represents straight-chain $(C_3\text{-}C_7)$-alkanediyl or $(C_3\text{-}C_7)$-alkenediyl, each of which may be substituted up to four times by identical or different radicals $R^4$ where
$R^4$ represents fluorine, trifluoromethyl or $(C_1\text{-}C_4)$-alkyl
  or
  two radicals $R^4$ attached to the same carbon atom are linked to each other and together with this carbon atom form a $(C_3\text{-}C_6)$-cycloalkane-1,1-diyl ring,
or a pharmaceutically acceptable salt thereof.
2. The compound of claim 1 in which
ring A represents an oxo-substituted azaheterocycle of the formula

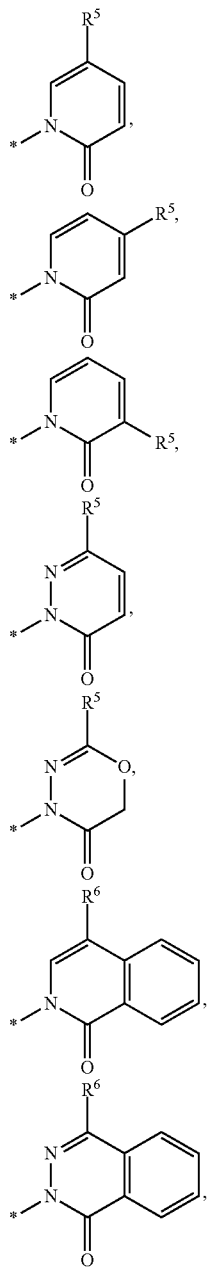

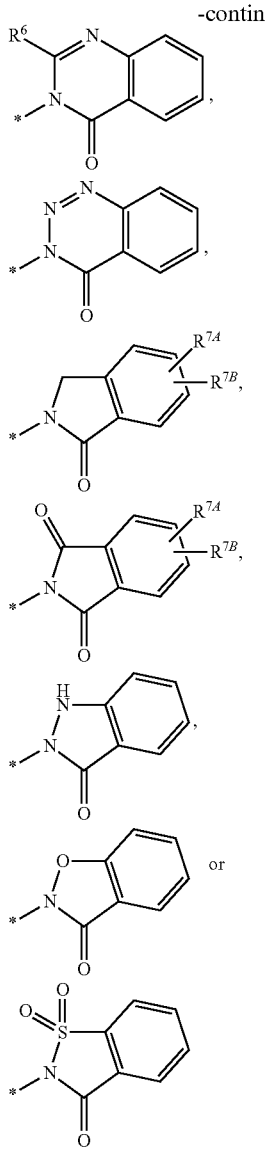

in which

* denotes the point of attachment to the remainder of the molecule, $R^5$ represents chlorine, $(C_1-C_6)$-alkyl, trifluoromethyl, $(C_3-C_6)$-cycloalkyl, 4- to 6-membered monocyclic heterocyclyl having a total of 4 to 6 ring atoms, which contains one or two ring heteroatoms selected from the group consisting of N, O, and S, or phenyl, where phenyl for its part may be substituted up to two times by identical or different radicals selected from the group consisting of fluorine, chlorine, bromine, cyano, $(C_1-C_4)$-alkyl, vinyl, trifluoromethyl, $(C_1-C_4)$-alkoxy and trifluoromethoxy, $R^6$ represents hydrogen or has the meaning of $R^5$ given above and $R^{7A}$ and $R^{7B}$ independently of one another represent hydrogen, fluorine or chlorine, or a pharmaceutically acceptable salt thereof.

3. The compound of claim 1 in which ring A represents an oxo-substituted azaheterocycle of the formula

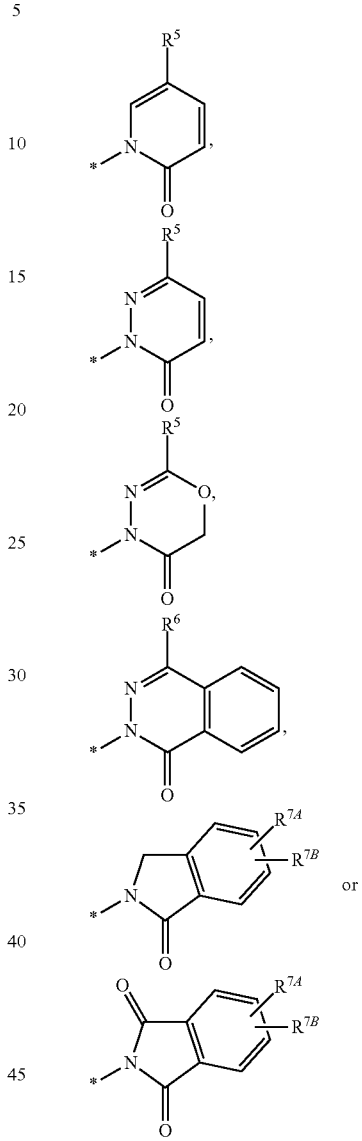

in which

* denotes the point of attachment to the remainder of the molecule, $R^5$ represents chlorine, $(C_1-C_6)$-alkyl, trifluoromethyl, $(C_3-C_6)$-cycloalkyl or phenyl, where phenyl for its part may be substituted up to two times by identical or different radicals selected from the group consisting of fluorine, chlorine, cyano, $(C_1-C_4)$-alkyl, trifluoromethyl, $(C_1-C_4)$-alkoxy and trifluoromethoxy, $R^6$ represents hydrogen or has the meaning of $R^5$ given above and $R^{7A}$ and $R^{7B}$ independently of one another represent hydrogen, fluorine or chlorine, $R^1$ represents hydrogen or $(C_1-C_4)$-alkyl, $R^2$ represents hydrogen, fluorine, chlorine or trifluoromethyl, R³ represents (C₃-C₆)-alkyl or (C₃-C₆)-alkenyl, each of which may be substituted by cyano, methoxy, ethoxy or trifluoromethoxy and up to six times by fluorine, or represents (C₃-C₆)-cycloalkyl or (C₄-C₆)-cycloalkenyl, each of which may be substituted up to two times by identical or different radicals from the group consisting of methyl, ethyl and trifluoromethyl and also up to four times by fluorine, or represents oxetanyl, and L represents straight-chain (C₃-C₆)-alkanediyl or (C₃-C₆)-alkenediyl, each of which may be substituted up to four times by identical or different radicals R⁴ where R⁴ represents fluorine, trifluoromethyl, methyl or ethyl or two radicals R⁴ attached to the same carbon atom are linked to each other and together with this carbon atom form a cyclopropane-1,1-diyl or cyclobutane-1,1-diyl ring, or a pharmaceutically acceptable salt thereof.

4. The compound of claim 1 in which ring A represents an oxo-substituted azaheterocycle of the formula

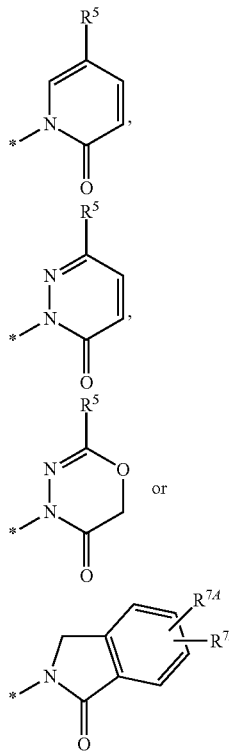

in which

* denotes the point of attachment to the remainder of the molecule,

R⁵ represents chlorine, trifluoromethyl or phenyl, where phenyl for its part may be substituted up to two times by identical or different radicals selected from the group consisting of fluorine, chlorine, methyl and tri-fluoromethyl, and R⁷ᴬ and R⁷ᴮ independently of one another represent hydrogen or fluorine, R¹ represents hydrogen, R² represents hydrogen, R³ represents propan-2-yl, butan-2-yl, pentan-2-yl, 3,3,3-trifluoropropan-1-yl, 1,1,1-trifluoropropan-2-yl, 1,1,1-trifluorobutan-2-yl, 4,4,4-trifluorobutan-2-yl, 4,4,4-trifluoro-2-methylbutan-1-yl, cyclopentyl or 3,3-difluorocyclopentyl, and L represents straight-chain (C₃-C₆)-alkanediyl or (C₃-C₆)-alkenediyl, each of which may be substituted up to four times by identical or different radicals R⁴ where R⁴ represents methyl or two radicals R⁴ attached to the same carbon atom are linked to each other and together with this carbon atom form a cyclopropane-1,1-diyl ring, or a pharmaceutically acceptable salt, solvate or solvate of a salt thereof.

5. A process for preparing a compound of claim 1 comprising either

[A] converting a compound of the formula (II)

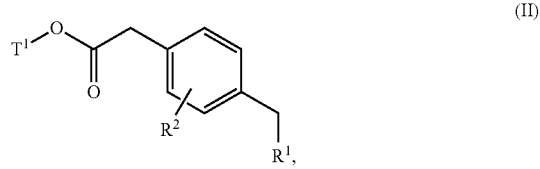

in which R¹ and R² have the meanings given in claim 1 and

T¹ represents (C₁-C₄)-alkyl, in an inert solvent in the presence of a base with a compound of the formula (III)

R³—X     (III), in which R³ has the meaning given in claim 1 and

X represents a leaving group, into a compound of the formula (IV)

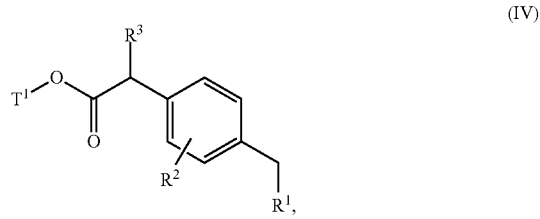

in which R¹, R², R³ and T¹ each have the meanings given above, or

[B] reacting a compound of the formula (V)

in which R³ has the meaning given in claim 1 and

T¹ represents (C₁-C₄)-alkyl, is, in an inert solvent, after deprotonation with a base, with a compound of the formula (VI)

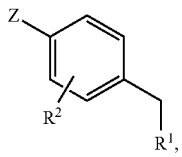
(VI)

in which $R^1$ and $R^2$ have the meanings given in claim 1 and

Z represents chlorine, bromine or iodine, in the presence of a suitable palladium catalyst to give a compound of the formula (IV)

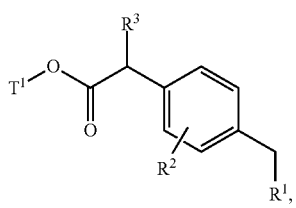
(IV)

in which $R^1$, $R^2$, $R^3$ and $T^1$ each have the meanings given above, brominating the compound of the formula (IV) in an inert solvent with elemental bromine or with N-bromosuccinimide to give a compound of the formula (VII)

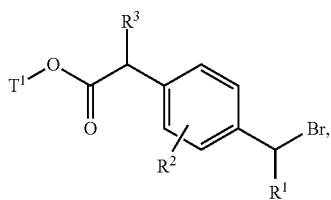
(VII)

in which $R^1$, $R^2$, $R^3$ and $T^1$ each have the meanings given above, and reacting the compound of formula (VII) in an inert solvent in the presence of a base with a compound of the formula (VIII)

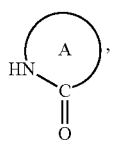
(VIII)

in which ring A represents an oxo-substituted azaheterocycle, as defined in claim 1, to give a compound of the formula (IX)

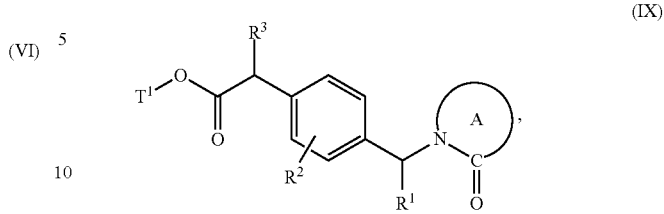
(IX)

in which ring A, $R^1$, $R^2$, $R^3$ and $T^1$ each have the meanings given above, removing the ester radical $T^1$ in (IX) under basic or acidic conditions, thereby producing a carboxylic acid of the formula (X)

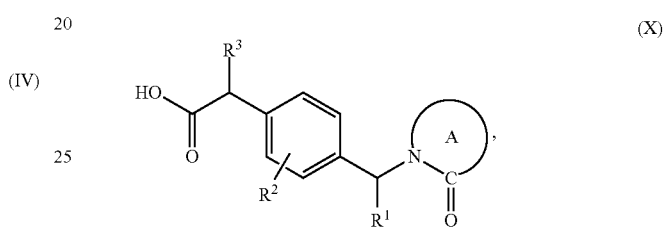
(X)

in which ring A, $R^1$, $R^2$ and $R^3$ each have the meanings given above, coupling the carboxylic acid of formula (X) in an inert solvent in the presence of a condensing agent or via the intermediate of the corresponding carbonyl chloride in the presence of a base with an amine of the formula (XI)

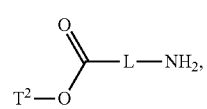
(XI)

in which L has the meaning given in claim 1 and $T^2$ represents $(C_1$-$C_4)$-alkyl, to give a compound of the formula (XII)

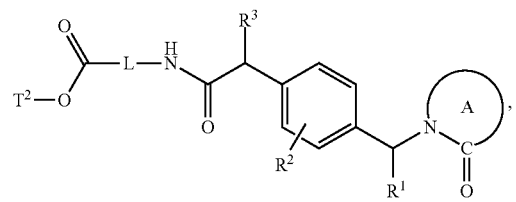
(XII)

in which ring A, $R^1$, $R^2$, $R^3$, L and $T^2$ each have the meanings given above, and the ester radical $T^2$ in (XII) is then removed by further basic or acidic solvolysis to give the carboxylic acid of the formula (I)

wherein the compounds of formula (I) are optionally separated by methods known to the skilled person into their enantiomers and/or diastereomers, and/or optionally reacted with the appropriate (i) solvent and/or (ii) base or acid to give a pharmaceutically acceptable salt thereof.

6. A pharmaceutical composition comprising a compound of claim 1 and at least one inert, non-toxic, pharmaceutically suitable excipient.

7. The pharmaceutical composition of claim 6, further comprising an active ingredient selected from the group consisting of an organic nitrate, an NO donor, a cGMP-PDE inhibitor, a stimulator of guanylate cyclase, an agent having antithrombotic activity, an agent lowering blood pressure, and an agent altering lipid metabolism.

8. A method for the treatment of heart failure, angina pectoris, hypertension, pulmonary hypertension, ischemias, vascular disorders, thromboembolic disorders and arteriosclerosis comprising administering to a human or animal an effective amount of a compound of claim 1.

9. The compound of claim 2, wherein ring A represents

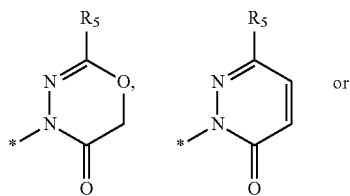

or

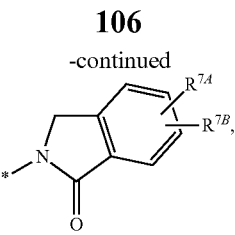

wherein,

* denotes the point of attachment to the remainder of the molecule, and $R^5$ has a meaning given in claim 2, and $R^{7A}$ and $R^{7B}$ each have a meaning given in claim 2.

10. The compound of claim 9, wherein $R^5$ is phenyl, and $R^{7A}$ and $R^{7B}$ are both hydrogen.

* * * * *

UNITED STATES PATENT AND TRADEMARK OFFICE
CERTIFICATE OF CORRECTION

PATENT NO. : 8,642,592 B2
APPLICATION NO. : 13/201924
DATED : February 4, 2014
INVENTOR(S) : Lampe et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 29 days.

Signed and Sealed this
Twelfth Day of May, 2015

Michelle K. Lee
*Director of the United States Patent and Trademark Office*